US012454728B2

(12) United States Patent
Darby et al.

(10) Patent No.: US 12,454,728 B2
(45) Date of Patent: Oct. 28, 2025

(54) COMPOSITIONS AND METHODS FOR AMPLIFYING, DETECTING OR QUANTIFYING HUMAN CYTOMEGALOVIRUS

(71) Applicant: Gen-Probe Incorporated, San Diego, CA (US)

(72) Inventors: Paul Darby, San Diego, CA (US); Siobhan Miick, San Diego, CA (US); Jo Ann Jackson, Lakeside, CA (US); Hee Cheol Kim, San Diego, CA (US); Amber Hillius, San Diego, CA (US); Ankur Shah, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 1232 days.

(21) Appl. No.: 17/269,775

(22) PCT Filed: Aug. 21, 2019

(86) PCT No.: PCT/US2019/047419

§ 371 (c)(1),
(2) Date: Feb. 19, 2021

(87) PCT Pub. No.: WO2020/041414

PCT Pub. Date: Feb. 27, 2020

(65) Prior Publication Data

US 2022/0074002 A1 Mar. 10, 2022

Related U.S. Application Data

(60) Provisional application No. 62/720,658, filed on Aug. 21, 2018.

(51) Int. Cl.
*C12P 19/34* (2006.01)
*C12Q 1/70* (2006.01)

(52) U.S. Cl.
CPC ....... *C12Q 1/705* (2013.01); *C12Q 2600/158* (2013.01)

(58) Field of Classification Search
CPC ...................................................... C12Q 1/701
See application file for complete search history.

(56) References Cited

U.S. PATENT DOCUMENTS

2014/0066326 A1* 3/2014 Nelson ................ C12Q 1/6865 435/5
2014/0193802 A1 7/2014 Lischka

OTHER PUBLICATIONS

Keyes, Characterization of the HCMV protein LUNA, and the cellular protein CyPA during latency/reactivation, Dissertation, 2011. (Year: 2011).*
Rychlik et el., Nucleic Acids Research 17(21), 8543-8551 (1989). (Year: 1989).*

* cited by examiner

*Primary Examiner* — Kenneth R Horlick
(74) *Attorney, Agent, or Firm* — Jeffrey E. Landes; Alston & Bird LLP

(57) ABSTRACT

Oligomer nucleotides, compositions, methods, kits, and uses are provided for detecting or quantifying a Human Cytomegalovirus virus 1 (CMV (human herpesvirus 5, HHV5) nucleic acid, e.g., using nucleic acid amplification and hybridization assays. Multiphase amplification of a CMV target sequence is also described. The oligomer nucleotides, compositions, methods, kits, and uses can be used to amplify and/or detect the UL56 gene of CMV.

17 Claims, No Drawings

Specification includes a Sequence Listing.

COMPOSITIONS AND METHODS FOR AMPLIFYING, DETECTING OR QUANTIFYING HUMAN CYTOMEGALOVIRUS

CROSS-REFERENCE TO RELATED APPLICATIONS

This application is a U.S. National Stage entry of International Application No. PCT/US2019/047419, filed Aug. 21, 2019, which claims the benefit of priority to U.S. Provisional Application No. 62/720,658, filed Aug. 21, 2018, which are herein incorporated by reference in their entirety for all purposes.

SEQUENCE LISTING

The Sequence Listing written in filed 535372_SeqListing_ST25.txt is 17 kilobytes in size, was created Aug. 21, 2019, and is hereby incorporated by reference.

BACKGROUND

Human Cytomegalovirus (CMV, also called human herpesvirus 5 (HHV5)) is part of a larger family of viruses that include Herpes simplex virus (HSV), Varicella-Zoster virus (VZV), and Epstein-Barr virus (EBV). CMV is an enveloped double-stranded DNA virus causing infections in humans. CMV is a common virus that can infect almost anyone. It is so common that almost all adults in developing countries and 50% to 85% of adults in the United States have been infected. CMV spreads from person to person through body fluids, such as blood, saliva, urine, semen, vaginal fluids, and breast milk. Similar to other herpes viruses, CMV establishes a lifelong latency that may reactivate intermittently. There is no cure. In the immunocompetent host, the CMV infection is generally asymptomatic and self-limited.

CMV infection is cause for concern in pregnant women, infants, and immunocompromised individuals. Active CMV infection during pregnancy can pass the virus to the baby. For people with compromised immunity, especially due to organ transplantation, CMV infection is an important cause of morbidity and mortality. However, medications can help treat newborns and people with weak immune systems.

In solid organ transplantation (SOT) recipients, CMV transmitted from the donor (D) organ to the recipient (R), may cause primary infection in CMV seronegative SOT recipients (R−) or re-infection in CMV seropositive SOT recipients (R+). In D−/R+ SOT recipients, the impaired CMV-specific immunity due to immunosuppression may result in re-activation of endogenous latent CMV. Since D+/R− SOT recipients lack the pre-existing host immunity, they are at high-risk for developing CMV disease, whereas R+ recipients constitute an intermediate-risk group (Razonable 2013). Once infected, CMV cannot be eradicated from the body due to its tendency for lifelong latency. Therefore, the goal of CMV therapy in SOT patients is to prevent the indirect effects of CMV infection on the transplant and/or the development of CMV disease, by suppression of viral replication. Viral load testing has become the main method to diagnose active disease due to CMV infections and a routine component in the care of transplant recipients (Rychert J., et. al 2014).

Testing is important in pregnant women and those with compromised or weakened immune systems. Current diagnostic tests look for anti-CMV antibodies. However, such testing requires multiple tests for accuracy and the person must be symptomatic. Additional diagnostic tests include culture, PCR, and the CMV pp65 antigenemia assay. The CMV pp65 antigenemia assay, which quantitates the number of CMV-infected leukocytes in peripheral blood, has been used in the detection and monitoring of CMV infection in immunocompromised patients.

There is a need for compositions and methods that allow sensitive and specific detection and quantification of CMV. This disclosure aims to meet these needs, provide other benefits, or at least provide the public with a useful choice.

SUMMARY

Described are amplification oligomers, nucleic acids, methods, compositions, and kits for detecting and/or quantifying human cytomegalovirus (CMV) in a sample, or to amplify a CMV UL56 gene sequence. The amplification oligomers include forward primers, reverse primers, promoter primers (e.g., T7 primers), non-promoter primers (e.g., NT7 primers), helper oligomers and displacer oligomers. Further described are probe oligomers and target capture oligomers (TCO) that facilitate detection of amplified sequence and isolation of CMV nucleotide sequence from a sample, respectively. The methods involve the amplification of viral nucleic acid to detect the CMV target sequence in the sample. The methods can advantageously provide for the sensitive detection CMV.

The amplification oligomers can be used in the amplification, detection, and/or quantification of a CMV sequence using any nucleic amplification method known in the art. The nucleic acid amplification methods can use thermal cycling, or they can be isothermal. Nucleic acid amplification methods known in the art include, but are not limited to, polymerase chain reaction (PCR), reverse transcriptase PCR (RT-PCR), nucleic acid sequence-based amplification (NASBA), replicase-mediated amplification (including Qβ-replicase-mediated amplification), ligase chain reaction (LCR), strand-displacement amplification (SDA), isothermal transcription-associated amplification and multi-phase isothermal transcription-associated amplification.

The described amplification oligomers can be used to amplify a CMV sequence. The amplified CMV sequence, the amplicon, includes all or a portion of SEQ ID NO: 1 and/or a complement thereof. The amplification oligomers are configured to amplify and optionally detect a CMV UL56 gene amplicon comprising all or a portion of SEQ ID NO: 1 and/or a complement thereof. In some embodiments, the amplicon comprises SEQ ID NO: 51 and/or a complement thereof and/or SEQ ID NO: 53 and/or a complement thereof. The amplicon may be DNA or RNA. Various methods in the art can be used to detect a CMV amplicon.

In some embodiments, a forward primer or non-promoter primer comprises 19-31 contiguous nucleobases having at least 80% identity to a nucleotide sequence present in SEQ ID NO: 2. In some embodiments, a non-promoter primer is an amplification oligonucleotide that binds specifically to its target sequence in a cDNA product of extension of the promoter primer, downstream from the promoter-primer end. The promoter primer is combined with non-promoter primer to form an amplification pair and together are configured to amplify a portion of the target nucleic acid. In some embodiments, a forward primer or non-promoter primer comprises the nucleotide sequence of SEQ ID NO: 10, SEQ ID NO: 11, or SEQ ID NO: 19. A forward primer or non-promoter primer is able to hybridize to SEQ ID NO:

79 and initiate DNA or RNA polymerization. Exemplary forward primers and non-promoter primers are provided in Table 1B.

In some embodiments, a reverse primer or promoter primer comprises 21-40 contiguous nucleobases having at least 80% identity to a nucleotide sequence present in SEQ ID NO: 3. In some embodiments, a reverse primer or promoter primer comprises the nucleotide sequence of SEQ ID NO: 23, SEQ ID NO: 24, SEQ ID NO: 25, or SEQ ID NO: 47. A reverse primer or promoter primer is able to hybridize to SEQ ID NO: 80 and initiate DNA or RNA polymerization. Exemplary reverse primers and promoter primers are provided in Table 1B.

An RNA polymerase promoter sequence can be added to any of the described forward and/or reverse primers to form a promoter primer. The RNA polymerase primer sequence is functionally linked to the 5' end of a described forward or reverse primer. In some embodiments, an RNA polymerase promoter sequence is linked to the 5' end of a reverse primer. An RNA polymerase promoter sequence can be, but is not limited to, a T7 RNA polymerase promoter sequence. A T7 RNA polymerase promoter sequence can contain the nucleotide sequence of SEQ ID NO: 78. Promoter primers having a T7 polymerase promoter sequence are referred to as T7 primers. In some embodiments, a promoter primer or T7 primer comprises the nucleotide sequence of: SEQ ID NO: 28, SEQ ID NO: 30, SEQ ID NO: 32, SEQ ID NO: 34, SEQ ID NO: 36, SEQ ID NO: 38, SEQ ID NO: 40 or SEQ ID NO: 46.

In some embodiments, a helper oligomer facilitates or enhances hybridization of a forward primer to a template nucleotide sequence. Similarly, in some embodiments, a displacer oligomer facilitates or enhances hybridization of a reverse primer to a template nucleic acid sequence. Exemplary helper and displacer oligomers are provided in Table 1B. Facilitating or enhancing hybridization of a primer to a template can facilitate or enhance amplification of the target nucleotide sequence. When used to facilitate hybridization of forward and/or reverse primers, helper oligomers and displacer oligomers may be blocked. When blocked, a helper or displacer oligomer is unable to prime polymerization from its 3' end. In some embodiments, helper and/or displacer oligomers can be forward primers or reverse primers. In some embodiments, a described helper and/or displacer oligomer can have an RNA polymerase promoter sequence linked to the 5' end of the helper or displacer oligomer to form a promoter primer. In some embodiments, a helper oligomer comprises SEQ ID NO: 10, SEQ ID NO: 14, SEQ ID NO: 15, SEQ ID NO: 17, SEQ ID NO: 18, or SEQ ID NO: 19. In some embodiments, a displacer oligomer comprises SEQ ID NO: 25, SEQ ID NO: 33, SEQ ID NO: 35, SEQ ID NO: 37, SEQ ID NO: 6, SEQ ID NO: 41, or SEQ ID NO: 12. Exemplary helper oligomers and displacer oligomers are provided in Table 1B.

The described probe oligomers (also termed detection oligomer) can be used to detect a CMV amplicon. In some embodiments, a probe oligomer comprises 24-35 contiguous nucleobases having at least 90% identity to a nucleotide sequence present in SEQ ID NO: 4. In some embodiments, a probe oligomer comprises 24-35 contiguous nucleobases that hybridize to SEQ ID NO: 81. In some embodiments, a probe oligomer comprises the nucleotide sequence of SEQ ID NO: 51, SEQ ID NO: 52, or SEQ ID NO: 57, wherein one or more uracil nucleotides can be substituted for thymine nucleotides. In some embodiments, a probe oligomer contains a hairpin. A hairpin can comprise 4-5 nucleobases at the 5' and 3' ends of the probe oligomer that are complementary to each other. Exemplary probe oligomers are provided in Table 1C. A probe oligomer can have one or more modified nucleotides. For any of the described probe oligomers, one or more nucleotides in the probe oligomer can be substituted for ribonucleotides, 2'-O-Methyl ribonucleotides, or a combination of ribonucleotides and 2'-O-Methyl ribonucleotides. In some embodiments, a probe oligomer can have 1, 2, 3, 4, 5, 6, 7, or more thymidines substituted for uridines. In some embodiments, all thymidines in a probe oligomer can be substituted for uridines. In some embodiments, a probe oligomer can have 1, 2, 3, 4, 5, 6, 7, or more uridines substituted for thymidines. In some embodiments, all uridines in a probe oligomer can be substituted for thymidines. In some embodiments, one or more of the uridines are 2'-O-Methyl ribonucleotides. In some embodiments, all of the uridines are 2'-O-Methyl ribonucleotides.

A probe oligomer can contain a one or more detectable markers or labels. A detectable marker can be, but is not limited to a fluorescent molecule. The fluorescent molecule can be attached to the 5' or 3' end of the probe oligomer or anywhere along the oligomer. In some embodiments a probe oligomer can be a molecular beacon or torch. A probe oligomer can contain a fluorescent molecule attached to the 5' end of the probe oligomer and a quencher attached to the 3' end of the probe oligomer or a fluorescent molecule can be attached to the 3' end of the probe oligomer and a quencher attached to the 5' end of the probe oligomer.

The described target capture oligomers (TCOs) can be used to capture or isolate the target CMV sequence from a sample. The CMV TCO comprises a target specific (TS) nucleotide sequence that hybridizes to (i.e., is complementary to) a region of a target nucleotide sequence in CMV. In some embodiments, the TCO TS sequence comprises a 10-35 nucleotide sequence having at least 90%, at least 95%, or 100% complementarity to a nucleotide sequence present in the target nucleic acid and hybridizes to a region in the target nucleic acid sequence (a TCO binding site). In some embodiments, the TCO TS sequence is 20-30 nucleotides in length. In some embodiments, the TCO TS sequence is 22-26 nucleotides in length and has at least 90% complementarity to a nucleotide sequence present in the target nucleic acid. The TCO TS and TCO binding site may be perfectly complementary or there may be one or more mismatches. The TCO includes an immobilized capture probe-binding region that binds to an immobilized capture probe (e.g., by specific binding pair interaction). Members of a specific binding pair (or binding partners) are moieties that specifically recognize and bind to each other. Members may be referred to as a first binding pair member (BPM1) and second binding pair member (BPM2), which represent a variety of moieties that specifically bind together. Specific binding pairs are exemplified by, e.g., a receptor and its ligand, enzyme and its substrate, cofactor or coenzyme, an antibody or Fab fragment and its antigen or ligand, a sugar and lectin, biotin and streptavidin or avidin, a ligand and chelating agent, a protein or amino acid and its specific binding metal such as histidine and nickel, substantially complementary polynucleotide sequences, which include completely or partially complementary sequences, and complementary homopolymeric sequences. Specific binding pairs may be naturally occurring (e.g., enzyme and substrate), synthetic (e.g., synthetic receptor and synthetic ligand), or a combination of a naturally occurring BPM and a synthetic BPM. In some embodiments, the TS sequence and the immobilized capture probe-binding region are both nucleic acid sequences. The TS sequence and the capture probe-binding region may be covalently joined to each other, or may be on different oligonucleotides joined by one or more linkers. In some embodiments, the capture probe-binding region comprises: a poly A sequence, a poly T sequence, or a polyT-polyA sequence. In some embodiments a polyT-polyA sequence comprises $(dT)_3(dA)_{30}$. One or more TCOs may be used in a target capture and/or amplification reaction. The one or more TCOs may bind to the same or difference target sequences. The target sequence may be from the same or different genes and/or from the same or different organisms. In some embodiments, a CMV TCO comprises the nucleotide sequence of SEQ ID NO: 6, SEQ ID NO: 8, SEQ ID NO: 43, or SEQ ID NO: 45 or a nucleic acid sequence having at least 90% identity to SEQ ID NO: 6, SEQ ID NO: 8, SEQ ID NO: 43, or SEQ ID NO: 45. In some embodiments, a CMV TCO containing a polyA sequence comprises SEQ ID NO: 7, SEQ ID NO: 9, SEQ ID NO: 42, or SEQ ID NO: 44 or a nucleic acid sequence having at least 90% identity to SEQ ID NO: 7, SEQ ID NO: 9, SEQ ID NO: 42, or SEQ ID NO: 44. Exemplary probe oligomers are provided in Table 1D. A TCO can have one or more modified nucleotides. For any of the described TCOs, one or more cytidines in the TCO can be substituted for 5'-methyl dCs. A TCO can have 1, 2, 3, 4, 5, 6, 7, or more cytidines substituted for 5'-methyl dCs. In some embodiments, all cytidines in a TCO can be substituted for 5'-methyl dCs.

In some embodiments, an amplification oligomer, detection oligomer, or TCO contains one or more modified nucleotides. An oligomer can have 1, 2, 3, 4, 5, 6, 7, 8, or more modified nucleotides. In some embodiments, more than 50%, more than 60%, more than 70%, more than 75%, more than 80%, more than 85%, more than 90%, more than 95%, or 100% of the nucleotides are modified. Modified nucleotides include nucleotides having modified nucleobases. Modified nucleobases include, but are not limited to, synthetic and natural nucleobases, 5-substituted pyrimidines, 5'-methyl cytosine, 6-azapyrimidines, N-2, N-6 and 0-6 substituted purines. Modified nucleotides also include nucleotides with a modified base, including, but not limited to, 2'-modified nucleotides (including, but not limited to 2'-O-methyl nucleotides and 2'-halogen nucleotides, such as 2'-fluoro nucleotides). Modified nucleotides also include nucleotides with modified linkages, such as, but not limited to, phosphorothioate linkages. In some embodiments, an amplification oligomer comprises two or more modified nucleotides. The two or more modified nucleotides may have the same or different modifications. In some embodiments, any of the described oligomers can contain one or more 5'-methyl cytosines. An oligomer can have 1, 2, 3, 4, 5, or more 5'-methyl cytosines. In some embodiments, all cytosine nucleotides in a described oligomer are 5'-methyl cytosine modified nucleotides. In some oligomers, 5'-methyl-2'deoxycytosine bases can be used to increase the stability of the duplex by raising the Tm by about 0.5°-1.3° C. for each 5'methyl-2'deoxycytosine incorporated in an oligomer, relative to the corresponding unmethylated oligomer.

The described amplification oligomers can be used to amplify a CMV UL56 sequence. In some embodiments, the described amplification oligomers can be used to amplify an CMV UL56 sequence using a thermal cycling reaction such as polymerase chain reaction (PCR). In some embodiments, the described amplification oligomers can be used to amplify a CMV UL56 sequence using an isothermal reaction such as transcription-mediated amplification (TMA). A transcription-mediated amplification can be single phase or multiphase (e.g., biphasic). Other nucleic acid amplification methods that can utilize the described amplification oligomers include, but are not limited to, nucleic acid sequence-based amplification (NASBA), replicase-mediated amplification, ligase chain reaction (LCR), strand-displacement amplification (SDA), and reverse transcriptase PCR (RT-PCR). A forward or helper oligomer is combined with a reverse or displacer oligomer to form an amplification pair. Any of the described forward or helper oligomers can be combined with any of the described reverse or displacer oligomers to form an amplification pair. In some embodiments, a first amplification oligomer (forward primer) and a second amplification oligomer (reverse primer) are configured to amplify a CMV UL56 amplicon of at least about 56, at least about 60, at least about 65, at least about 70, at least about 75, at least about 80, at least about 85, at least about 90, or at least about 95 nucleotides in length.

In some embodiments, the described oligomers can be used in single phase or multiphase (e.g., biphasic) transcription mediated amplification. In multi-phase amplification, at least a portion of a target nucleic acid sequence is subjected to a first phase amplification reaction under conditions that do not support exponential amplification of the target nucleic acid sequence. The first phase amplification reaction generates a first amplification product, which is subsequently subjected to a second phase amplification reaction under conditions allowing exponential amplification of the first amplification product, thereby generating a second amplification product. Multi-phase amplification yields improved sensitivity and precision at the low end of analyte concentration compared with the single-phase format. Multi-phase amplification can yield improved precision and shorten detection time.

In some embodiments, multi-phase amplification of a CMV target nucleic acid sequence comprises:

a) contacting a sample containing or suspected of containing CMV target nucleic acid sequence with a target capture mixture, wherein the target capture mixture comprises an RNA polymerase promoter-containing oligonucleotide (promoter primer), and optionally a target capture oligomer (TCO) and/or a displacer oligomer to form a pre-amplification hybrid;
b) isolating the pre-amplification hybrid;
c) contacting the pre-amplification hybrid with a first phase amplification mixture; wherein the first phase amplification mixture comprises: a non-RNA polymerase promoter-containing oligonucleotide (non-promoter primer), optionally a helper oligomer, a reverse transcriptase, an RNA polymerase, dNTPs, and NTPs, wherein the first phase amplification mixture is lacking in at least one component necessary for exponential amplification;
d) amplifying at least a portion of the target nucleic acid sequence of the pre-amplification hybrid in a substantially isothermal, transcription-associated amplification reaction under conditions that support linear amplification to form a first amplification product;
e) contacting the first amplification product with a second phase amplification mixture, wherein the second phase amplification mixture comprises the RNA polymerase promoter-containing oligonucleotide or the at least one component necessary for exponential amplification that is lacking in the first phase amplification mixture;
f) exponentially amplifying the first amplification product in a substantially isothermal transcription-associated amplification reaction to produce a second amplification product; and
g) detecting the second amplification product.

In some embodiments, the second phase amplification mixture contains a detection oligomer. In some embodiments, one or more of any of the oligomers, may be used in the reaction. For instance, one or more TCOs, one or more promoter primers, one or more non-promoter primers, one or more displacer oligomers, one or more helper oligomers, and/or one or more probe oligomers.

In some embodiments, the pre-amplification hybrid comprises the target nucleic acid hybridized to the promoter primer. In some embodiments, the pre-amplification hybrid comprises the target nucleic acid hybridized to one or more TCOs and a promoter primer. In some embodiments, the pre-amplification hybrid comprises the target nucleic acid hybridized to one or more TCOs, a promoter primer, and optionally a displacer oligomer. In some embodiments, isolating the pre-amplification hybrid comprises capturing the pre-amplification hybrid using a solid support. In some embodiments, the solid support includes an immobilized capture probe. The solid support can be, but is not limited to, magnetically attractable particles. In some embodiments, isolating the pre-amplification hybrid comprises removing promoter primer that is not hybridized to the target nucleic acid.

In some embodiments, during the first phase isothermal transcription-associated amplification reaction, the promoter primer, bound specifically to the target nucleic acid at its target sequence, is extended by reverse transcriptase (RT) to create a cDNA copy, using the target nucleic acid as a template. The non-promoter primer is then enzymatically extended to produce a double strand DNA, using the cDNA as template. Next, the double strand DNA serves as template for RNA transcription from the RNA polymerase promoter provided by the promoter primer. The non-promoter primer then binds to the RNA and is extended by reverse transcriptase to yield the first amplification product. In the absence of additional promoter primer, exponential amplification does not occur. The first amplification product is then contacted with the second phase amplification mixture to initiate the exponential second phase amplification.

In some embodiments, each of the first and second phase isothermal transcription-associated amplification reactions include an RNA polymerase and a reverse transcriptase. In some embodiments, the reverse transcriptase includes an endogenous RNase H activity.

In some embodiments, compositions suitable for use in a first phase amplification of a multi-phase amplification of CMV comprise: (a) an optional TCO, (b) a promoter primer hybridized to a first portion of a CMV target nucleic acid sequence; (c) optionally a displacer oligomer hybridized to a portion of a CMV target nucleic acid sequence; (d) a non-promoter primer; (e) optionally a helper oligomer; and (f) additional components necessary to amplify the target nucleic acid during a linear first phase amplification reaction, but lacking at least one component required for exponential amplification of the target nucleic acid sequence. In some embodiments, the lacking at least one component necessary for exponential amplification is additional (free) promoter primer. In some embodiments, the first phase amplification lacks promoter primer that is not hybridized to the target nucleic acid in the pre-amplification hybrid. The additional components can include one or more of: RNA-dependent DNA polymerase, RNA polymerase, dNTPs, NTPs, buffers, and salts.

In some embodiments, compositions suitable for use in a second or subsequent phase amplification of a multi-phase amplification of CMV comprise: (a) a first amplification product, (b) promoter primer, (c) non-promoter primer, (d) other necessary components necessary to amplify the target nucleic acid during an exponential second phase amplification reaction. The additional components can include one or more of: RNA-dependent DNA polymerase, RNA polymers, dNTPs, NTPs, buffers, and salts.

In some embodiments, methods are described for multi-phase amplification and/or detection of CMV, comprising:

(a) contacting a sample containing or suspected of containing a CMV target nucleic acid with a promoter primer specific for a first portion of the target nucleic acid sequence, under conditions allowing hybridization of the promoter primer to the first portion of the target nucleic acid sequence, thereby generating a pre-amplification hybrid that includes the promoter primer and the target nucleic acid sequence;

(b) isolating the pre-amplification hybrid by target capture onto a solid support followed by washing to remove any of the promoter primer that did not hybridize to the first portion of the target nucleic acid sequence in step (a);

(c) amplifying, in a first phase amplification reaction mixture, at least a portion of the target nucleic acid sequence of the pre-amplification hybrid isolated in step (b) in a first phase, substantially isothermal, transcription-associated amplification reaction under conditions that support linear amplification thereof, but do not support exponential amplification thereof (i.e., the first phase amplification reaction mixture lacks at least one component necessary for exponential amplification of the first amplification product), thereby resulting in a reaction mixture including a first amplification product;

(d) combining the reaction mixture including the first amplification product with the at least one component necessary for exponential amplification of the first amplification product, but that is lacking from the reaction mixture that includes the first amplification product, to produce a second phase amplification reaction mixture;

(e) exponentially amplifying the first amplification product in a second phase amplification mixture, in a substantially isothermal transcription-associated amplification reaction, to produce a second amplification product; and (f) optionally detecting the second amplification product.

In some embodiments, the at least one component necessary for exponential amplification of the first amplification product includes the primer promoter (e.g., promoter primer in addition to promoter primer hybridized with the target nucleic acid and isolated as part of the pre-amplification hybrid). In some embodiments, the first amplification product of step (c) is a cDNA molecule with the same polarity as the target nucleic acid sequence in the sample, and the second amplification product of step (e) is an RNA molecule. The second amplification product can be detected using a sequence-specific detection probe. The sequence-specific detection probe can be, but is not limited to, a conformation-sensitive probe that produces a detectable signal when hybridized to the second amplification product. In some embodiments, the sequence-specific detection probe in step (f) is a fluorescently labeled sequence-specific hybridization probe. Detecting can be performed at regular time intervals. In some embodiments, the detecting is performed in real time. In some embodiments, detecting the second amplification product comprises quantifying the target nucleic acid sequence in the sample using a linear calibration curve.

In some embodiments a Target Enhancer Reagent (TER) is added to the sample prior to addition of the TCO or target capture mixture. In some embodiments, the TER comprises 1.68 M lithium hydroxide (LiOH). The amount of TER to be combining with a sample can be determined empirically. TER can be added to provide a final LiOH concentration in the sample of 50-350 mM. The sample can be added to the TER or the TER can be the sample.

Described are compositions and kits for amplifying, detecting and/or quantifying CMV. In some embodiments, the described compositions and kits provide for the direct, rapid, specific and/or sensitive detection of CMV. The compositions and kits can comprise one or more of the described amplification oligomers, probe oligomers, and/or TCOs. In some embodiments, a composition or kit comprises at least one forward primer and at least one reverse primer. In some embodiments, a composition or kit comprises at least one NT7 primer and at least one T7 primer. A composition or kit may further comprise at least one probe oligomer. A composition or kit may further comprise at least one TCO. A composition or kit may further comprise one or more helper oligomers and/or displacer oligomers. A composition or kit may further comprise any one or more of: capture beads, Target Capture Reagent, Target Capture Wash Solution, Target Enhancer Reagent, Amplification Reagent (lyophilized pellet), Amplification Reagent Reconstitution Solution, Enzyme Reagent (lyophilized pellet), Enzyme Reagent Reconstitution Solution, Promoter Reagent (lyophilized pellet), Promoter Reagent Reconstitution Solution, Positive Calibrator, CMV positive control nucleic acid, negative control nucleic acid, nucleotide triphosphates, DNA polymerase, RNA polymerase, reverse transcriptase, Sample Transport Medium and instructions for use.

Described are methods for amplifying, detecting, and/or quantifying a target CMV sequence, the methods comprising the steps of contacting a sample containing or suspected of containing CMV, with at least two amplification oligomers for amplifying a target region of a CMV, wherein the at least two amplification oligomers comprise a forward primer and a reverse primer as described above that each hybridize to the UL56 gene of CMV. An in vitro nucleic acid amplification reaction is performed, wherein CMV target nucleic acid present in the sample is used as a template for generating an amplification product. In some embodiments, the forward and reverse primer each hybridize to SEQ ID NO: 1 or a complement thereof. In some embodiments, the forward and reverse primers amplify an amplicon comprising SEQ ID NO: 51 or a complement thereof.

In some embodiments, the methods further include detecting the presence or absence of the amplification product, thereby indicating the presence or absence of CMV in the sample. The amplification product is detected using a probe oligomer. A described probe oligomer can be used in amplification reactions to detect and/or quantify CMV in a sample.

In some embodiments, quantification of CMV in samples can be used to aid in the management of solid organ transplant recipients. In patients receiving anti-CMV therapy, serial CMV DNA measurements can be used to assess viral response to treatment. The viral load information may also be used to diagnose CMV disease in transplant patients.

In some embodiments, the described oligonucleotides, compositions, and methods are suitable for use in amplifying and/or detecting CMV in multiplex multi-phase reactions. The multiplex multi-phase reactions can be used to detect CMV and one or more other target sequences and/or organisms.

DETAILED DESCRIPTION

A. Definitions

Before describing the present teachings in detail, it is to be understood that the disclosure is not limited to specific compositions or process steps, as such may vary. It should be noted that, as used in this specification and the appended claims, the singular form “a,” “an,” and “the” include plural references unless the context clearly dictates otherwise. Thus, for example, reference to “an oligomer” includes a plurality of oligomers and the like. The conjunction “or” is to be interpreted in the inclusive sense, i.e., as equivalent to “and/or,” unless the inclusive sense would be unreasonable in the context.

All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

Unless otherwise apparent from the context, any element, embodiment, step, feature or aspect of the invention can be performed in combination with any other.

It will be appreciated that there is an implied “about” prior to the temperatures, concentrations, times, etc. discussed in the present disclosure, such that slight and insubstantial deviations are within the scope of the present teachings herein. In general, the term “about” indicates insubstantial variation in a quantity of a component of a composition not having any significant effect on the activity or stability of the composition. All ranges are to be interpreted as encompassing the endpoints in the absence of express exclusions such as “not including the endpoints”; thus, for example, “within 10-15” includes the values 10 and 15. Also, the use of “comprise,” “comprises,” “comprising,” “contain,” “contains,” “containing,” “include,” “includes,” and “including” are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Approximating language, throughout the specification and claims, may be applied to modify any quantitative or qualitative representation that could permissibly vary without resulting in a change in the basic function to which it is related. Accordingly, a value modified by a term such as “about” or “approximately” is not to be limited to the precise value specified, and may include values that differ from the specified value. In some embodiments, about or approximately indicates insignificant variation and/or variation of less than 5%.

Unless specifically noted, embodiments in the specification that recite “comprising” various components are also contemplated as “consisting of” or “consisting essentially of” the recited components; embodiments in the specification that recite “consisting of” various components are also contemplated as “comprising” or “consisting essentially of” the recited components; and embodiments in the specification that recite "consisting essentially of" various components are also contemplated as "consisting of" or "comprising" the recited components (this interchangeability does not apply to the use of these terms in the claims). "Consisting essentially of" means that additional component(s), composition(s) or method step(s) that do not materially change the basic and novel characteristics of the compositions and methods described herein may be included in those compositions or methods. Such characteristics include the ability to detect a CMV nucleic acid sequence present in a sample with specificity that distinguishes the CMV nucleic acid from other known pathogens, optionally at a sensitivity that can detect about 1-100 copies of the virus within about 45 min from the beginning of an amplification reaction that makes amplified viral sequences that are detected.

A "sample," "specimen," "biological sample," "biological specimen," "clinical sample," or "clinical specimen" is any sample containing or suspected of containing an analyte of interest, e.g., microbe, virus, nucleic acid such as a gene (e.g., target nucleic acid), or component thereof, which includes nucleic acid sequences in or derived from an analyte. A "sample" may contain or may be suspected of containing CMV or components thereof, such as nucleic acids or fragments of nucleic acids. Samples may be from any source, such as, but not limited to, biological specimens, clinical specimens, and environmental sources. A sample may be a complex mixture of components. Samples include "biological samples" which include any tissue or material derived from a living or dead mammal or organism, including, e.g., blood, plasma, serum, blood cells, saliva, and mucous, cerebrospinal fluid (to diagnose CMV infections of the central nervous system) and samples-such as biopsies—from or derived from genital lesions, anogenital lesions, oral lesions, mucocutaneous lesions, skin lesions and ocular lesions or combinations thereof. Biological samples also include, but are not limited to, respiratory tissue, exudates (e.g., bronchoalveolar lavage), sputum, tracheal aspirates, lymph node, gastrointestinal tissue, feces, urine, genitourinary fluid, and biopsy cells or tissue. Samples may also include samples of in vitro cell culture constituents including, e.g., conditioned media resulting from the growth of cells and tissues in culture medium. A sample may be treated to physically or mechanically disrupt tissue or cell structure to release intracellular nucleic acids into a solution which may contain enzymes, buffers, salts, detergents and the like, to prepare the sample for analysis. Examples of environmental samples include, but are not limited to, water, ice, soil, slurries, debris, biofilms, airborne particles, and aerosols. Samples may also include samples of in vitro cell culture constituents including, e.g., conditioned media resulting from the growth of cells and tissues in culture medium. Samples may be processed specimens or materials, such as obtained from treating a sample by using filtration, centrifugation, sedimentation, or adherence to a medium, such as matrix or support. Other processing of samples may include, but are not limited to, treatments to physically or mechanically disrupt tissue, cellular aggregates, or cells to release intracellular components that include nucleic acids into a solution which may contain other components, such as, but not limited to, enzymes, buffers, salts, detergents and the like.

The term "contacting" means bringing two or more components together. Contacting can be achieved by mixing all the components in a fluid or semi-fluid mixture. Contacting can also be achieved when one or more components are brought into physical contact with one or more other components on a solid surface such as a solid tissue section or a substrate.

"Nucleic acid" and "polynucleotide" refer to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid may be ribose, deoxyribose, or similar compounds with substitutions, e.g., 2' methoxy or 2' halide substitutions. Nitrogenous bases may be conventional bases (A, G, C, T, U), analogs thereof (e.g., inosine or others; see *The Biochemistry of the Nucleic Acids* 5-36, Adams et al., ed., $11^{th}$ ed., 1992), derivatives of purines or pyrimidines (e.g., $N^4$-methyl deoxyguanosine, deaza- or aza-purines, deaza- or aza-pyrimidines, pyrimidine bases with substituent groups at the 5 or 6 position, purine bases with a substituent at the 2, 6, or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT No. WO 93/13121). Nucleic acids may include one or more "abasic" residues where the backbone includes no nitrogenous base for position(s) of the polymer (U.S. Pat. No. 5,585,481). A nucleic acid may comprise only conventional RNA or DNA sugars, bases and linkages, or may include both conventional components and substitutions (e.g., conventional bases with 2' methoxy linkages, or polymers containing both conventional bases and one or more base analogs). Nucleic acid includes "locked nucleic acid" (LNA), an analog containing one or more LNA nucleotide monomers with a bicyclic furanose unit locked in an RNA mimicking sugar conformation, which enhance hybridization affinity toward complementary RNA and DNA sequences (Vester and Wengel, 2004, Biochemistry 43(42):13233-41). Nucleic acids may include modified bases that alter the function or behavior of the nucleic acid, e.g., addition of a 3-terminal dideoxyribonucleotide to block additional nucleotides from being added to the nucleic acid. Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates). It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24, and 25).

A "target nucleic acid" or "target" is a nucleic acid containing a target nucleic acid sequence. A "target nucleic acid sequence," "target sequence" or "target region" is a specific deoxyribonucleotide or ribonucleotide sequence comprising a nucleotide sequence of a target organism, such as CMV, to be amplified. A target sequence, or a complement thereof, contains sequences that hybridize to capture oligonucleotides, amplification oligomers, and/or detection oligomers used to amplify and/or detect the target nucleic acid. The target nucleic acid may include other sequences besides the target sequence which may not be amplified. Target nucleic acids may be DNA or RNA and may be either single-stranded or double-stranded. A target nucleic acid can be, but is not limited to, a genomic nucleic acid, a transcribed nucleic acid, such as an rRNA, or a nucleic acid derived from a genomic or transcribed nucleic acid.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated the window of comparison between two sequences is defined by the entire length of the shorter of the two sequences.

The term "complementarity" refers to the ability of a polynucleotide to form hydrogen bond(s) (hybridize) with another polynucleotide sequence by either traditional Watson-Crick or other non-traditional types. A percent complementarity indicates the percentage of bases, in a contiguous strand, in a first nucleic acid sequence which can form hydrogen bonds (e.g., Watson-Crick base pairing) with a second nucleic acid sequence (e, g., 5, 6, 7, 8, 9, 10 out of 10 being 50%, 60%, 70%, 80%, 90%, and 100% complementary). Percent complementarity is calculated in a similar manner to percent identify.

An exemplary portion of CMV sequence is provided in the Table 1A (for brevity, complete CMV genomes, which are known in the art, are not included). Unless otherwise indicated, "hybridizing to a CMV nucleic acid" includes hybridizing to either a sense or antisense strand of CMV nucleic acid or to an RNA transcribed from the genomic sequence.

In some embodiments, an amplification oligomer, probe oligomer or TCO can contain one or more modified nucleotides. An amplification oligomer can have 1, 2, 3, 4, 5, 6, or more modified nucleotides. Modified nucleotides include nucleotides having modified nucleobases. Modified nucleobases include, but are not limited to, synthetic and natural nucleobases, 5-substituted pyrimidines, 6-azapyrimidines, and N-2, N-6 and 0-6 substituted purines. Modified nucleotides also include nucleotides with a modified base, including, but not limited to, 2'-modified nucleotides (including, but not limited to 2'-O-methyl nucleotides and 2'-halogen nucleotides, such as 2'-fluoro nucleotides). "C residues" include methylated (5-methylcytosine) and unmethylated cytosines unless the context indicates otherwise.

By "RNA and DNA equivalents" is meant RNA and DNA molecules having essentially the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence. Unless otherwise indicated, reference to a CMV nucleic acid includes CMV RNA and DNA equivalents thereof.

An "oligomer", "oligonucleotide", or "oligo" is a polymer made up of two or more nucleoside subunits or nucleobase subunits coupled together. The oligonucleotide may be DNA and/or RNA and analogs thereof. In some embodiments, the oligomers are in a size range having a 5 to 15 nt lower limit and a 50 to 500 nt upper limit. In some embodiments, the oligomers are in a size range of 10-100 nucleobases, 10-90 nucleobases, 10-80 nucleobases, 10-70 nucleobases, or 10-60 nucleobases. In some embodiments, oligomers are in a size range with a lower limit of about 5 to 15, 16, 17, 18, 19, or 20 nucleobases and an upper limit of about 50 to 100 nucleobases. In some embodiments, oligomers are in a size range with a lower limit of about 10 to 21 nucleobases and an upper limit of about 22 to 100 nucleobases. An oligomer does not consist of wild-type chromosomal DNA or the in vivo transcription products thereof. Oligomers can made synthetically by using any well-known in vitro chemical or enzymatic method, and may be purified after synthesis by using standard methods, e.g., high-performance liquid chromatography (HPLC). Described are oligomers that include RNA polymerase promoter-containing oligomers (also termed promoter primers; e.g., T7 primers), non-RNA polymerase promoter-containing oligomers (also termed non-T7 primers, NT7 primers, or non-promoter primers), probe oligomers (also termed detection oligomers or detection probes, probes, or Torches), target capture oligomers (TCOs), forward primers, reverse primers, helper oligomers, and displacer oligomers.

An "immobilized capture probe" provides a means for joining a TCO to a solid support. In some embodiments, an immobilized capture probe contains a base sequence recognition molecule joined to the solid support, which facilitates separation of bound target polynucleotide from unbound material. Any known solid support may be used, such as matrices and particles free in solution. For example, solid supports may be nitrocellulose, nylon, glass, polyacrylate, mixed polymers, polystyrene, silane polypropylene and magnetically attractable particles. In some embodiments, the supports include magnetic spheres that are monodisperse (i.e., uniform in size ±about 5%). The immobilized capture probe may be joined directly (e.g., via a covalent linkage or ionic interaction), or indirectly to the solid support. Common examples of useful solid supports include magnetic particles or beads.

The term "target capture" refers to selectively separating or isolating a target nucleic acid from other components of a sample mixture, such as cellular fragments, organelles, proteins, lipids, carbohydrates, or other nucleic acids. A target capture system may be specific and selectively separate a predetermined target nucleic acid from other sample components (e.g., by using a sequence specific to the intended target nucleic acid, such as a TCO TS sequence), or it may be nonspecific and selectively separate a target nucleic acid from other sample components by using other characteristics of the target (e.g., a physical trait of the target nucleic acid that distinguishes it from other sample components which do not exhibit that physical characteristic). Target capture methods and compositions have been previously described in detail (U.S. Pat. Nos. 6,110,678 and 6,534,273; and US Pub. No. 2008/0286775 A1). In some embodiments, target capture utilizes a TCO in solution phase and an immobilized capture probe attached to a support to form a complex with the target nucleic acid and separate the captured target from other components.

The term "separating," "isolating," or "purifying" generally refers to removal of one or more components of a mixture, such as a sample, from one or more other components in the mixture. Sample components include nucleic acids in a generally aqueous solution phase, which may include cellular fragments, proteins, carbohydrates, lipids, and other compounds. In some embodiments, at least 70%, at least 75%, at least 80%, at least 85%, at least 90%, or at least 95%, of the target nucleic acid is separated or removed from other components in the mixture.

"Nucleic acid amplification" or "amplification" refers to any in vitro procedure that produces multiple copies of a target nucleic acid sequence, or its complementary sequence, or fragments thereof (i.e., an amplified sequence containing less than the complete target nucleic acid). Examples of nucleic acid amplification procedures include transcription associated methods, such as transcription-mediated amplification (TMA), nucleic acid sequence-based amplification (NASBA) and others (e.g., U.S. Pat. Nos. 5,399,491, 5,554,516, 5,437,990, 5,130,238, 4,868,105, and 5,124,246), replicase-mediated amplification (e.g., U.S. Pat. No. 4,786,600), the polymerase chain reaction (PCR) (e.g., U.S. Pat. Nos. 4,683,195, 4,683,202, and 4,800,159), ligase chain reaction (LCR) (e.g., EP Pat. App. 0320308), and strand-displacement amplification (SDA) (e.g., U.S. Pat. No. 5,422,252). Replicase-mediated amplification uses self-replicating RNA molecules, and a replicase such as Qβ-replicase. PCR amplification uses DNA polymerase, primers, and thermal cycling steps to synthesize multiple copies of the two complementary strands of DNA or cDNA. LCR amplification uses at least four separate oligonucleotides to amplify a target and its complementary strand by using multiple cycles of hybridization, ligation, and denaturation. SDA uses a primer that contains a recognition site for a restriction endonuclease that will nick one strand of a hemi-modified DNA duplex that includes the target sequence, followed by amplification in a series of primer extension and strand displacement steps. Particular embodiments use PCR or TMA, but it will be apparent to persons of ordinary skill in the art that oligomers disclosed herein may be readily used as primers in other amplification methods.

Transcription-associated amplification uses a DNA polymerase, an RNA polymerase, deoxyribonucleoside triphosphates, ribonucleoside triphosphates, a promoter-containing oligonucleotide, and optionally may include other oligonucleotides, to ultimately produce multiple RNA transcripts from a nucleic acid template (described in detail in U.S. Pat. Nos. 5,399,491 and 5,554,516, Kacian et al., U.S. Pat. No. 5,437,990, Burg et al., PCT Nos. WO 88/01302 and WO 88/10315, Gingeras et al., U.S. Pat. No. 5,130,238, Malek et al., U.S. Pat. Nos. 4,868,105 and 5,124,246, Urdea et al., PCT No. WO 94/03472, McDonough et al., PCT No. WO 95/03430, and Ryder et al., each of which is incorporated herein by reference). Methods that use TMA are described in detail previously (U.S. Pat. Nos. 5,399,491 and 5,554,516, each of which is incorporated herein by reference).

The term "substantially isothermal amplification" refers to an amplification reaction that is conducted at a substantially constant temperature. The isothermal portion of the reaction may be preceded or followed by one or more steps at a variable temperature, for example, a first denaturation step and a final heat inactivation step or cooling step. It will be understood that this definition does not exclude small variations in temperature but is rather used to differentiate the isothermal amplification techniques from other amplification techniques known in the art that basically rely on "cycling temperatures" in order to generate the amplified products. Isothermal amplification differs from PCR, for example, in that the latter relies on cycles of denaturation by heating followed by primer hybridization and polymerization at a lower temperature.

An "amplicon" or "amplification product" is a nucleic acid molecule generated in a nucleic acid amplification reaction and which is derived from a target nucleic acid. An amplicon or amplification product contains a target nucleic acid sequence that may be of the same or opposite sense as a target nucleic acid.

An "amplification oligomer" refers to an oligonucleotide that hybridizes to a target nucleic acid, or its complement, and participates in a nucleic acid amplification reaction. An amplification oligomer can be a primer, forward primer, reverse primer, promoter-primer, non-promoter primer, helper oligomer, or displacer oligomer. In some embodiments, amplification oligomers contain at least about 10 contiguous bases, and optionally at least 11, 12, 13, 14, 15, 16, 17, 18, 19, 20, or 21 contiguous bases, that are complementary to a region of the target nucleic acid sequence or its complementary strand. The contiguous bases may be at least about 80%, at least about 90%, at least 95%, or completely complementary to the target sequence to which the amplification oligomer binds. In some embodiments, an amplification oligomer contains 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 contiguous bases that are at least 80%, at least 90%,at least 95%, or 100% complementary to a region of the target nucleic acid sequence or its complementary strand. In some embodiments, an amplification oligomer contains additional 3' or 5' sequences that are not complementary to the target nucleic acid sequence. One skilled in the art will understand that the recited ranges include all whole and rational numbers within the range (e.g., 92% or 98.377%). Particular amplification oligomers are about 10 to about 60 bases long and optionally may include modified nucleotides. In some embodiments, a primer can contain at least one methylated cytosine and/or at least one 2'-modified nucleotide.

"Single phase amplification" refers for nucleic amplification reactions in which all components required for nucleic acid amplification are present in the reaction mixture when amplification is started.

"Linear amplification" refers to an amplification mechanism that is designed to produce an increase in the target nucleic acid linearly proportional to the amount of target nucleic acid in the reaction. For instance, multiple RNA copies can be made from a DNA target using a transcription-associated reaction, where the increase in the number of copies can be described by a linear factor (e.g., starting copies of template×n). In some embodiments, a first phase linear amplification in a multiphase amplification procedure increases the starting number of target nucleic acid strands or the complements thereof by at least 10-fold, at least 100-fold, or at least 1,000-fold before the second phase amplification reaction is initiated. An example of a linear amplification system is "T7-based Linear Amplification of DNA" (TLAD; see Liu et al., BMC Genomics, 4: Art. No. 19, May 9, 2003). Other methods are disclosed herein. Accordingly, the term "linear amplification" refers to an amplification reaction which does not result in the exponential amplification of a target nucleic acid sequence. The term "linear amplification" does not refer to a method that simply makes a single copy of a nucleic acid strand, such as the transcription of an RNA molecule into a single cDNA molecule as in the case of reverse transcription.

"Exponential amplification" refers to nucleic acid amplification that is designed to produce an increase in the target nucleic acid geometrically proportional to the amount of target nucleic acid in the reaction. For example, PCR produces one DNA strand for every original target strand and for every synthesized strand present. Similarly, transcription-associated amplification produces multiple RNA transcripts for every original target strand and for every subsequently synthesized strand. The amplification is exponential because the synthesized strands are used as templates in subsequent rounds of amplification. An amplification reaction need not actually produce exponentially increasing amounts of nucleic acid to be considered exponential amplification, so long as the amplification reaction is designed to produce such increases.

A "primer" refers to an oligomer that hybridizes to a template nucleic acid and has a 3' end that is extended by polymerization. A primer may be optionally modified, e.g., by including a 5' region that is non-complementary to the target sequence. Such modification can include functional additions, such as tags, promoters, or other sequences used or useful for manipulating or amplifying the primer or target oligonucleotide. Within the context of transcription mediated amplification, a primer modified with a 5' promoter sequence may be referred to as a "promoter-primer." A person of ordinary skill in the art of molecular biology or biochemistry will understand that an oligomer that can function as a primer can be modified to include a 5' promoter sequence and then function as a promoter-primer, and, similarly, any promoter-primer can serve as a primer with or without its 5' promoter sequence.

In cyclic amplification methods that detect amplicons in real-time, the term "Threshold cycle" (Ct) is a measure of the emergence time of a signal associated with amplification of target, and is generally 10× standard deviation of the normalized reporter signal. Once an amplification reaches the "threshold cycle," generally there is considered to be a positive amplification product of a sequence to which the probe binds. The identity of the amplification product can then be determined through methods known to one of skill in the art, such as gel electrophoresis, nucleic acid sequencing, and other such well known methods.

As used herein, the term "relative fluorescence unit" ("RFU") is a unit of measurement of fluorescence intensity. RFU varies with the characteristics of the detection means used for the measurement, and can be used as a measurement to compare relative intensities between samples and controls. The analytical sensitivity (limit of detection or LoD) is determined from the median tissue culture infective dose ($TCID_{50}$/ml). The $TCID_{50}$/ml is that amount of a pathogenic agent that will produce pathological change in 50% of cell cultures inoculated.

"Detection probe" or "probe" refers to an oligomer that hybridizes specifically to a target sequence, including an amplified sequence, under conditions that promote nucleic acid hybridization, for detection of the target nucleic acid. Detection may either be direct (i.e., probe hybridized directly to the target) or indirect (i.e., a probe hybridized to an intermediate structure that links the probe to the target). A probe's target sequence generally refers to a specific sequence within a larger sequence which the probe hybridizes specifically. A detection probe may include complementary (target-specific) sequence and a non-complementary (non-target-complementary) sequence. Such non-target-complementary sequences can include sequences which will confer a desired secondary or tertiary structure, such as a hairpin structure, which can be used to facilitate detection and/or amplification. (e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1). The complementary and non-complementary sequences can be contiguous or joined by a linker. In some embodiments, the linker is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ linker. In some embodiments, the linker is a $C_9$ linker. A detection oligomer can be RNA, DNA, contain one or more modified nucleotides, or a combination thereof. In some embodiments, a detection oligomer contains one or more 2' methoxy nucleotides. In some embodiments, a detection oligomer contains all 2' methoxy ribonucleotides. Probes of a defined sequence may be produced by techniques known to those of ordinary skill in the art, such as by chemical synthesis, and by in vitro or in vivo expression from recombinant nucleic acid molecules.

Detection can be achieved using single-stranded nucleic acid torches that are present during target amplification and hybridize to the amplicon in real time. Each torch has a fluorophore and a quencher. The torches contain complementary regions at each end. These complementary regions bind to each other and form a "closed" torch. In the closed configuration, the fluorophore and quencher are in close proximity and the fluorophore signal is quenched. That is, it does not emit a detectable signal when excited by light. However, when the torch binds to the complementary target, the complementary regions within the torch are forced apart to form an "open" torch. In the open form, the fluorophore and quencher are not in close proximity and the fluorophore signal is detectable when excited (i.e., no longer quenched). Amplicon-torch binding results in the separation of the quencher from the fluorophore; which allows fluorophore excitation in response to light stimulus and signal emission at a specific wavelength. The torches can be present during amplification and bind to the complementary amplicon as it is generated in real time. As more amplicon is created, more torch is bound, and more signal is created. The signal eventually reaches a level that it can be detected above the background and ultimately reaches a point where all available torch is bound to amplicon and the signal reaches a maximum. At the start of amplification, and low copy number of the amplified sequence, most of the probe oligomer is closed (the 3' and 5' ends are base paired, and the fluorescent signal is quenched. During amplification, more probe oligomer binds to target sequence, thus separating the 3' and 5' ends of the probe oligo, leading to increases fluorescence (decreased quenching of fluorescence). After further amplification, the fluorescent signal approaches a maximum.

"Label" or "detectable label" refers to a moiety or compound joined directly or indirectly to a probe that is detected or leads to a detectable signal. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal. Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent, or chemiluminescent compound), and fluorescent compound (i.e., fluorophore). Fluorophores include those that absorb light in the range of about 495 to 650 nm and emit light in the range of about 520 to 670 nm, which include, but are not limited to, those known as FAM™, TET™, CAL FLUOR™ (Orange or Red), QUASAR™, fluorescein, hexochloro-Fluorescein (HEX), rhodamine, Carboxy-X-Rhodamine (ROX), tetramethylrhodamine, IAEDANS, EDANS, DABCYL, coumarin, BODIPY FL, lucifer yellow, eosine, erythrosine, Texas Red, ROX, CY dyes (such as CY5),Cyanine 5.5 (Cy5.5) and fluorescein/QSY7 dye compounds. Fluorophores may be used in combination with a quencher molecule that absorbs light when in close proximity to the fluorophore to diminish background fluorescence. Such quenchers are well known in the art and include, but are not limited to, BLACK HOLE QUENCHER™ (or BHQ™, including, but not limited to, Black Hole Quencher-2 (BHQ2)) or TAMRA™ compounds. Particular embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 5,283,174, 5,656,207, and 5,658,737). Particular homogeneous detectable labels include chemiluminescent compounds, including acridinium ester ("AE") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are well known (e.g., Sambrook et al., *Molecular Cloning, A Laboratory Manual,* 2nd ed. (Cold Spring Harbor Laboratory Press, Cold Spring Harbor, NY, 1989) at Chapt. 10, and U.S. Pat. Nos. 5,658,737, 5,656,207, 5,547,842, 5,283,174, and 4,581,333, and EP Pat. App. 0 747 706). Particular methods of linking an AE compound to a nucleic acid are known (e.g., U.S. Pat. Nos. 5,585,481 and 5,639,604, see column 10, line 6 to column 11, line 3, and Example 8). Particular AE labeling positions are a probe's central region and near a region of A/T base pairs, at a probe's 3' or 5' terminus, or at or near a mismatch site with a known sequence that is the probe should not detect compared to the desired target sequence. Other detectably labeled probes include TaqMan™ probes, molecular torches, and molecular beacons. TaqMan™ probes include a donor and acceptor label wherein fluorescence is detected upon enzymatically degrading the probe during amplification in order to release the fluorophore from the presence of the quencher. Molecular torches and beacons exist in open and closed configurations wherein the closed configuration quenches the fluorophore and the open position separates the fluorophore from the quencher to allow fluorescence. Hybridization to target opens the otherwise closed probes.

By "hybridization" or "hybridize" is meant the ability of two completely or partially complementary nucleic acid strands to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., R. L. P. Adams et al., *The Biochemistry of the Nucleic Acids* (11th ed. 1992).)

By "preferentially hybridize" is meant that under stringent hybridization conditions, an amplification or detection probe oligomer can hybridize to its target nucleic acid to form stable oligomer:target hybrid, but not form a sufficient number of stable oligomer:non-target hybrids. Amplification and detection oligomers that preferentially hybridize to a target nucleic acid are useful to amplify and detect target nucleic acids, but not non-targeted nucleic acids, especially in phylogenetically closely related organisms. Thus, the oligomer hybridizes to target nucleic acid to a sufficiently greater extent than to non-target nucleic acid to enable one having ordinary skill in the art to accurately amplify and/or detect the presence (or absence) of nucleic acid derived from the specified influenza viruses as appropriate. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. In some embodiments, there is at least a 10-fold difference between target and non-target hybridization signals in a test sample, at least a 20-fold difference, at least a 50-fold difference, at least a 100-fold difference, at least a 200-fold difference, at least a 500-fold difference, or at least a 1,000-fold difference. In some embodiments, non-target hybridization signals in a test sample are no more than the background signal level.

By "stringent hybridization conditions," or "stringent conditions" is meant conditions permitting an oligomer to preferentially hybridize to a target nucleic acid (such as a CMV nucleic acid) and not to nucleic acid derived from a closely related non-target nucleic acids. While the definition of stringent hybridization conditions does not vary, the actual reaction environment that can be used for stringent hybridization may vary depending upon factors including the GC content and length of the oligomer, the degree of similarity between the oligomer sequence and sequences of non-target nucleic acids that may be present in the test sample, and the target sequence. Hybridization conditions include the temperature and the composition of the hybridization reagents or solutions. Exemplary hybridization assay conditions for amplifying and/or detecting target nucleic acids derived from one or more strains of CMV with the oligomers of the present disclosure correspond to a temperature of about 60° C. when the salt concentration is in the range of about 0.6-0.9 M. Specific hybridization assay conditions are set forth infra in the Examples section. Other acceptable stringent hybridization conditions could be easily ascertained by those having ordinary skill in the art.

By "competes for hybridization to a CMV nucleic acid under stringent conditions" with a referenced oligomer is meant that an oligomer substantially reduces the binding of the referenced oligomer to its target CMV sequence under stringent conditions, the competing oligomer when supplied in excess can reduce binding of the referenced oligomer at a sub-saturating concentration by about 20%, 30%, 40%, 50%, or more, or the Tm of the competing oligomer is higher than or within about 5, 4, 3, 2, or 1° C. of the Tm of the referenced oligomer to the target. Suitable oligonucleotide competition assay conditions and procedures are known in the art.

By "assay conditions" is meant conditions permitting stable hybridization of an oligonucleotide to a target nucleic acid. Assay conditions do not require preferential hybridization of the oligonucleotide to the target nucleic acid.

Sequences are "sufficiently complementary" if they allow stable hybridization of two nucleic acid sequences, e.g., stable hybrids of probe and target sequences, although the sequences need not be completely complementary. That is, a "sufficiently complementary" sequence that hybridizes to another sequence by hydrogen bonding between a subset series of complementary nucleotides by using standard base pairing (e.g., G:C, A:T, or A:U), although the two sequences may contain one or more residues (including abasic positions) that are not complementary so long as the entire sequences in appropriate hybridization conditions to form a stable hybridization complex. Sufficiently complementary sequences may be at least about 80%, at least about 90%, or completely complementary in the sequences that hybridize together. Appropriate hybridization conditions are well known to those skilled in the art, can be predicted based on sequence composition, or can be determined empirically by using routine testing (e.g., Sambrook et al., *Molecular Cloning, A Laboratory Manual*, 2nd ed. at §§ 1.90-1.91, 7.37-7.57, 9.47-9.51 and 11.47-11.57, particularly §§ 9.50-9.51, 11.12-11.13, 11.45-11.47 and 11.55-11.57).

In some embodiments, an oligomer, such as a helper oligomer or a displacer oligomer is blocked. A blocked, or "non-extendable" oligomer includes a blocking moiety at or near its 3'-terminus that prevents extension of a nascent nucleic acid chain by a polymerase (i.e., the oligomer is blocked). A blocking group near the 3' end is, in some embodiments, within five residues of the 3' end and is sufficiently large to limit binding of a polymerase to the oligomer. In some embodiments a blocking group is covalently attached to the 3' terminus. Many different chemical groups may be used to block the 3' end, e.g., alkyl groups, non-nucleotide linkers, alkane-diol dideoxyribonucleotide residues, and cordycepin. Further examples of blocking moieties include a 3'-deoxy nucleotide (e.g., a 2',3'-dideoxy nucleotide); a 3'-phosphorylated nucleotide; a fluorophore, quencher, or other label that interferes with extension; an inverted nucleotide (e.g., linked to the preceding nucleotide through a 3'-to-3' phosphodiester, optionally with an exposed 5'-OH or phosphate); or a protein or peptide joined to the oligonucleotide so as to prevent further extension of a nascent nucleic acid chain by a polymerase. A non-extendable oligonucleotide of the present disclosure may be at least 10 bases in length, and may be up to 15, 20, 25, 30, 35, 40, 50 or more nucleotides in length. Non-extendable oligonucleotides that comprise a detectable label can be used as probes. In some embodiments a helper oligomer or displacer oligomer is blocked (i.e., is non-extendable or contains a blocking moiety).

References, particularly in the claims, to "the sequence of SEQ ID NO: X" refer to the base sequence of the corresponding sequence listing entry and do not require identity of the backbone (e.g., RNA, 2'-O-Me RNA, or DNA) or base modifications (e.g., methylation of cytosine residues) unless otherwise indicated.

A "degenerate" position in an oligomer refers to a position where more than one base pairs are present in a population of the oligomer. For example, a nucleotide can be presented as Y, which represents C or T/U. Oligomers with degenerate positions can be synthesized by providing a mixture of nucleotide precursors corresponding to the desired degenerate combination at the step of the synthesis where incorporation of a degenerate position is desired.

A "non-Watson Crick" (NWC) position in an oligomer refers to a position where the oligomer is configured to hybridize to at least one CMV target sequence with a non-Watson Crick pairing, such as G-U, G-T, or G-A (either the G or the U/T/A can be the base in the oligomer). In some embodiments, the NWC position is configured to hybridize via a wobble (G-U or G-T) or purine-purine (G-A) pair.

Unless defined otherwise, all scientific and technical terms used herein have the same meaning as commonly understood by those skilled in the relevant art. General definitions may be found in technical books relevant to the art of molecular biology, e.g., "Dictionary of Microbiology and Molecular Biology, 2nd ed." (Singleton et al., 1994, John Wiley & Sons, New York, NY) or "The Harper Collins Dictionary of Biology" (Hale & Marham, 1991, Harper Perennial, New York, NY).

B. Oligomers

The CMV Target region, which contains the region to be amplified, is shown in Table 1A. Amplification oligomers suitable for amplification of the CMV target region can be found in Table 1B. The amplification oligomers contain nucleotide sequences present in the forward (Fwd) primer/helper region, reverse (Rev) primer region, and/or displacer region, and hybridize to the forward (Fwd) primer/helper, reverse (Rev) primer, and displacer complementary (Compl.) regions shown in Table 1A. The probe oligomers contain nucleotide sequence present in the probe region, and hybridize to the primer complementary (Compl.) region regions shown in Table 1A. Probe oligomers suitable for detection of a CMV amplicon can be found in Table 1C. TCOs suitable for capture of a CMV nucleic acid can be found in Table 1D. An exemplary T7 Promoter sequence can be found in Table 1E.

TABLE 1A

CMV UL56 gene target region sequence, Amplification oligomer regions, probe region.

| Oligomer name | Sequence | SEQ ID NO. |
|---|---|---|
| CMV Target Region | gtatcctcgtgcagcgccttcagcagcatctccagatagagagtcagcagcgaactctgcgtacgattctgcg ccaccacctccgggtagatcttccggtacagatacactatagccgccgcgtttctcttgaacggcgtggactcc gccagtaacacgttcggatcgcagtactttagacactccagctccatggcgtattcgttgcatttcgaacacact acgcatagtttctgtaacaaattcatctccatgactcgactcgctcacgtacgagacgctgtcgtccggtctggc gccggccagagacat | 1 |
| Fwd Primer/Helper Region | gaactctgcgtacgattctgcgccaccacctccgggtagatcttccggtacagatacactatagccgccgcgtt t | 2 |
| Fwd Primer/Helper Compl. Region | aaacgcggcggctatagtgtatctgtaccggaagatctacccggaggtggtggcgcagaatcgtacgcaga gttc | 79 |

TABLE 1A-continued

CMV UL56 gene target region sequence, Amplification oligomer regions, probe region.

| Oligomer name | Sequence | SEQ ID NO. |
|---|---|---|
| Rev Primer Region | tcgtacgtgagcgagtcgagtcatggagatgaatttgttacagaaactatgcgtagtgtgttcgaaatgcaacg aatacgccatggagctggagtgtctaaagta | 3 |
| Rev Primer Compl. Region | tactttagacactccagctccatggcgtattcgttgcatttcgaacacactacgcatagtttctgtaacaaattcatc tccatgactcgactcgctcacgtacga | 80 |
| Displacer Region | tcgtacgtgagcgagtcgagtcatggagatgaatttgttacagaaactatgcgtagtgtgt | 5 |
| Displacer Compl. Region | acacactacgcatagtttctgtaacaaattcatctccatgactcgactcgctcacgtacga | 82 |
| Probe Region | gaacggcgtggactccgccagtaacacgttcggatcgcag | 4 |
| Probe Compl. Region | ctgcgatccgaacgtgttactggcggagtccacgccgtt | 81 |

TABLE 1B

Amplification Oligomer sequences.

| Oligomer name | Sequence | SEQ ID NO. |
|---|---|---|
| | Forward Primers (e.g., non-promoter primers or NT7 Primers) | |
| Fwd seq 1 | gtacgattctgcgcca | 10 |
| Fwd seq 2 | cagatacactatagccgccg | 11 |
| SEQ ID NO: 11 | cagatacactatagccgccg | 11 |
| SEQ ID NO: 13 | gtacagatacactatagccgccg | 13 |
| SEQ ID NO: 14 | cacctccgggtagatcttc | 14 |
| SEQ ID NO: 15 | gtacgattctgcgccaccacct | 15 |
| SEQ ID NO: 16 | actctgcgtacgattctgcgcca | 16 |
| SEQ ID NO: 17 | gaactctgcgtacgattctgcgcca | 17 |
| SEQ ID NO: 18 | gaactctgcgtacgattctgcgccaccacct | 18 |
| SEQ ID NO: 19 | ggtacagatacactatagccgccgcgttt | 19 |
| | Helper Oligomers | |
| Helper Seq 1 | gtacgattctgcgcca | 10 |
| Helper Seq 2 | ggtacagatacactatagccgccgcgttt | 19 |
| SEQ ID NO: 14 | cacctccgggtagatcttc | 14 |
| SEQ ID NO: 15 | gtacgattctgcgccaccacct | 15 |
| SEQ ID NO: 17 | gaactctgcgtacgattctgcgcca | 17 |
| SEQ ID NO: 18 | gaactctgcgtacgattctgcgccaccacct | 18 |
| SEQ ID NO: 19 | ggtacagatacactatagccgccgcgttt | 19 |
| | Reverse Primers | |
| Rev Seq 1 | ccatggagctggagtgtctaaag | 23 |
| Rev Seq 2 | aatgcaacgaatacg | 24 |
| Rev Seq 3 | gtacgtgagcgagtcgagtcat | 25 |
| SEQ ID NO: 23 | ccatggagctggagtgtctaaag | 23 |
| SEQ ID NO: 27 | tgtgttcgaaatgcaacgaatacg | 27 |
| SEQ ID NO: 29 | aatgcaacgaatacgccatggagctggagtgtctaaagta | 29 |
| SEQ ID NO: 31 | aatgcaacgaatacgccatggagctggagtgtctaaagt | 31 |
| SEQ ID NO: 33 | tcgtacgtgagcgagtcgagtcatg | 33 |
| SEQ ID NO: 35 | tcgtacgtgagcgagtcgagtcat | 35 |
| SEQ ID NO: 37 | cgtacgtgagcgagtcgagtcatg | 37 |
| SEQ ID NO: 6 | gtacgtgagcgagtcgagtcatg | 6 |
| SEQ ID NO: 41 | cagaaactatgcgtactgtgt | 41 |
| SEQ ID NO: 47 | gcaacgaatacgccatggagctggagtgtctaaag | 47 |
| | Promoter Primers (T7 Primers) | |
| SEQ ID NO: 28 | aatttaatacgactcactatagggagaaatgcaacgaatacgccatggagctggagtgtctaaagta | 28 |
| SEQ ID NO: 30 | aatttaatacgactcactatagggagaaatgcaacgaatacgccatggagctggagtgtctaaagt | 30 |
| SEQ ID NO: 32 | aatttaatacgactcactatagggagatcgtacgtgagcgagtcgagtcatg | 32 |
| SEQ ID NO: 34 | aatttaatacgactcactatagggagatcgtacgtgagcgagtcgagtcat | 34 |
| SEQ ID NO: 36 | aatttaatacgactcactatagggagacgtacgtgagcgagtcgagtcatg | 36 |
| SEQ ID NO: 38 | aatttaatacgactcactatagggagagtacgtgagcgagtcgagtcatg | 38 |

TABLE 1B-continued

Amplification Oligomer sequences.

| Oligomer name | Sequence | SEQ ID NO. |
|---|---|---|
| SEQ ID NO: 40 | aatttaatacgactcactatagggagacagaaactatgcgtactgtgt | 40 |
| SEQ ID NO: 46 | aatttaatacgactcactatagggagagcaacgaatacgccatggagctggagtgtctaaag | 46 |
| | Displacer Oligomers | |
| Displacer Seq 1 | gtacgtgagcgagtcgagtcat | 25 |
| SEQ ID NO: 33 | tcgtacgtgagcgagtcgagtcatg | 33 |
| SEQ ID NO: 35 | tcgtacgtgagcgagtcgagtcat | 35 |
| SEQ ID NO: 37 | cgtacgtgagcgagtcgagtcatg | 37 |
| SEQ ID NO: 6 | gtacgtgagcgagtcgagtcatg | 6 |
| SEQ ID NO: 41 | cagaaactatgcgtactgtgt | 41 |
| SEQ ID NO: 12 | gttacagaaactatgcgta | 12 |
| SEQ ID NO: 72 | atgaatttgttacagaaactatgcg | 72 |
| SEQ ID NO: 73 | atgaatttgttacagaaactatgcgta | 73 |
| SEQ ID NO: 74 | gaatttgttacagaaactatgcgta | 74 |
| SEQ ID NO: 75 | gaatttgttacagaaactatgcg | 75 |
| SEQ ID NO: 76 | tgttacagaaactatgcgta | 76 |
| SEQ ID NO: 77 | gttacagaaactatgcgtactgtg | 77 |
| SEQ ID NO: 86 | cagaaactatgcgtactgtg | 86 |
| SEQ ID NO: 87 | agaaactatgcgtactgtgttc | 87 |

TABLE 1C

Probe Oligomer sequences.

| Oligomer name | Sequence Probe oligomers (including Torches) | SEQ ID NO. |
|---|---|---|
| Probe Seq 1 | ggactccgccagtaac | 51 |
| Probe Seq 2 | ggactccgccagtaacacgttcg | 52 |
| SEQ ID NO: 53 | cgtggactccgccagtaacacgtt | 53 |
| SEQ ID NO: 54 | gaacggcguggacuccgccaguaacgcguucgcguuc | 54 |
| SEQ ID NO: 55 | gaacggcguggacuccgccaguaacgcguucg | 55 |
| SEQ ID NO: 56 | ccguggacuccgccaguaacacguucgcacgg | 56 |
| SEQ ID NO: 57 | ccguggacuccgccaguaacacguucg | 57 |
| SEQ ID NO: 58 | cguggacuccgccaguaacacguucgccacg | 58 |
| SEQ ID NO: 59 | cguggacuccgccaguaacacguucg | 59 |
| SEQ ID NO: 60 | cggacuccgccaguaacacguucggaccg | 60 |
| SEQ ID NO: 61 | cggacuccgccaguaacacguucg | 61 |
| SEQ ID NO: 62 | cggacuccgccaguaacacguucgggucccg | 62 |
| SEQ ID NO: 64 | ccguggacuccgccaguaacacguucggcacgg | 64 |
| SEQ ID NO: 65 | ccguggacuccgccaguaacacguucgg | 65 |
| SEQ ID NO: 66 | ccguggacuccgccaguaacacguucggagcacgg | 66 |
| SEQ ID NO: 67 | ccguggacuccgccaguaacacguucggag | 67 |
| SEQ ID NO: 68 | ccguggacuccgccaguaacacguucggaucgcagcacgg | 68 |
| SEQ ID NO: 69 | ccguggacuccgccaguaacacguucggaucgcag | 69 |
| SEQ ID NO: 70 | cggacuccgccaguaacacguucggaucgcaggaccg | 70 |
| SEQ ID NO: 71 | cggacuccgccaguaacacguucggaucgcag | 71 |
| SEQ ID NO: 20 | ggacuccgccaguaacacguucggaucgcaguacagucc | 20 |
| SEQ ID NO: 21 | ggacuccgccaguaacacguucggaucgcaguac | 21 |

TABLE 1C-continued

| Probe Oligomer sequences. | | |
|---|---|---|
| Oligomer name | Sequence Probe oligomers (including Torches) | SEQ ID NO. |
| SEQ ID NO: 22 | gaacggcguggacuccgccaguaacacguucgcguuc | 22 |
| SEQ ID NO: 26 | gaacggcguggacuccgccaguaacacguucg | 26 |
| SEQ ID NO: 39 | cggacuccgccaguaacacguucgg | 39 |

TABLE 1D

| Target Capture Oligomer sequences | | |
|---|---|---|
| Oligomer name | Sequence Target Capture Oligomers | SEQ ID NO. |
| SEQ ID NO: 6 | gtacgtgagcgagtcgagtcatg | 6 |
| SEQ ID NO: 7 | gtacgtgagcgagtcgagtcatgtttaaaaaaaaaaaaaaaaaaaaaaaaaaaaaa | 7 |
| SEQ ID NO: 8 | tgtcacttccttgagtatatag | 8 |
| SEQ ID NO: 9 | tgtcacttccttgagtatatagtttaaaaaaaaaaaaaaaaaaaaaaaaaaaaaa | 9 |
| SEQ ID NO: 42 | gtggtggcgcagaatcgtacgcagagttcgtttaaaaaaaaaaaaaaaaaaaaaaaaaaaaaa | 42 |
| SEQ ID NO: 43 | gtggtggcgcagaatcgtacgcagagttcg | 43 |
| SEQ ID NO: 44 | gtcagtcggcatagcgagcggcctttaaaaaaaaaaaaaaaaaaaaaaaaaaaaaa | 44 |
| SEQ ID NO: 45 | gtcagtcggcatagcgagcggcc | 45 |

TABLE 1E

| T7 Promoter sequence. | | |
|---|---|---|
| Oligomer name | Sequence T7 Promoter Oligomer | SEQ ID NO. |
| T7 Sequence | aatttaatacgactcactatagggaga | 78 |

The described amplification oligomers are configured to hybridize specifically to a CMV UL56 gene nucleic acid. In some embodiments, the amplification oligomers have target-hybridizing regions from about 19-40 bases in length or about 19, 20, 21, 22, 23, 24, 25, 26, 27, 28, 29, 30, 31, 32, 33, 34, 35, 36, 37, 38, 39, or 40 bases in length. In some embodiments, an oligomer comprises a second region of sequence in addition to the target-hybridizing region, such as a T7 RNA polymerase promoter, which can be located 5' of the target-hybridizing region. In some embodiments, an oligomer does not comprise a second region of sequence.

In some embodiments, an amplification oligomer comprises of any of the sequences of Table 1B. In some embodiments, and amplification oligomer consists of any of the sequences of Table 1B. In some embodiments, an amplification oligomer comprises an oligomer that competes with any of the sequences in Table 1B for binding to a CMV target nucleic acid under stringent conditions. The CMV target nucleic acid can be, but is not limited to, SEQ ID NO. 1 or a complement thereof. Any of the described forward primers or non-promoter primers may be combined with any the described reverse primers or promoter primers to form an amplification oligomer pair, (amplification oligomer combination). Similarly, any of the helper oligomers, displacer oligomers, or probe oligomers can be combined with any amplification oligomer pair. In some embodiments, a first amplification oligomer (e.g., forward primer) and a second amplification oligomer (e.g., reverse primer) are configured to amplify a CMV UL56 amplicon of at least about 56, at least about 60, at least about 65, at least about 70, at least about 75, at least about 80, at least about 85, at least about 90, or at least about 95 nucleotides in length. In some embodiments, a first amplification oligomer (e.g., forward primer) and a second amplification oligomer (e.g., reverse primer) are configured to amplify a CMV UL56 amplicon of 56-340, 56-312, 56-252, or 56-227, 95-340, 95-312, 95-252, or 95-227 nucleotides in length. In some embodiments, a first amplification oligomer (e.g., forward primer) and a second amplification oligomer (e.g., reverse primer) are configured to amplify a CMV UL56 amplicon of 90, 91, 92, 93, 94, 95, 96, 97, 98, 99, or 100 nucleotides in length.

In some embodiments, a forward primer or non-promoter primer comprises 19, 20, 21, 22, 23, 24, 25, 26, 27, 28, 29, 30, 31, or 19-31 contiguous nucleobases having at least 80% or at least 90% identity to a 19, 20, 21, 22, 23, 24, 25, 26, 27, 28, 29, 30, 31, or 19-31 nucleotide sequence present it SEQ ID NO: 2. In some embodiments, a forward primer or non-promoter primer comprises 19, 20, 21, 22, 23, 24, 25, 26, 27, 28, 29, 30, 31, or 19-31 contiguous nucleobases having a nucleotide sequence present in SEQ ID NO: 2. In some embodiments, a forward primer or non-promoter primer comprises the nucleotide sequence of SEQ ID NO: 10 or SEQ ID NO: 11. In some embodiments, a forward primer or non-promoter primer comprises or consists of a nucleotide sequence selected from the group consisting of: SEQ ID NO: 11, SEQ ID NO: 13, SEQ ID NO: 14, SEQ ID NO: 15, SEQ ID NO: 16, SEQ ID NO: 17, SEQ ID NO: 18, and SEQ ID NO: 19. In some embodiments, a forward primer or non-promoter primer comprises a nucleotide sequence having 90% identity to SEQ ID NO: 11, SEQ ID NO: 13, SEQ ID NO: 14, SEQ ID NO: 15, SEQ ID NO: 16, SEQ ID NO: 17, SEQ ID NO: 18, or SEQ ID NO: 19. In some embodiments, a forward primer or non-promoter primer hybridizes to SEQ ID NO: 79 and is capable of initiating DNA or RNA polymerization. In some embodiments, a forward primer or non-promoter primer comprises an oligomer capable of competing with any of SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, or SEQ ID NO: 19 for hybridizing to SEQ ID NO. 79.

In some embodiments, a reverse primer or promoter primer comprises 21, 22, 23, 24, 25, 26, 27, 28, 29, 30, 31, 32, 33, 34, 35, 36, 37, 38, 39, 40, or 21-40 contiguous nucleobases having at least 80% or at least 90% identity to a 21, 22, 23, 24, 25, 26, 27, 28, 29, 30, 31, 32, 33, 34, 35, 36, 37, 38, 39, 40, or 21-40 nucleotide sequence present in SEQ ID NO: 3. In some embodiments, a reverse primer or promoter primer comprises 21, 22, 23, 24, 25, 26, 27, 28, 29, 30, 31, 32, 33, 34, 35, 36, 37, 38, 39, 40, or 21-40 contiguous nucleobases having a nucleotide sequence present in SEQ ID NO: 3. In some embodiments, a reverse primer or promoter primer comprises the nucleotide sequence of SEQ ID NO: 23, SEQ ID NO: 24, or SEQ ID NO: 25. In some embodiments, a reverse primer or promoter primer comprises or consists of a nucleotide sequence selected from the group consisting of: SEQ ID NO: 6, SEQ ID NO: 27, SEQ ID NO: 29, SEQ ID NO: 31, SEQ ID NO: 33, SEQ ID NO: 35, SEQ ID NO: 37, SEQ ID NO: 41, or SEQ ID NO: 47. In some embodiments, a reverse primer or promoter primer comprises a nucleotide sequence having 90% identity to SEQ IN NO: 6, SEQ ID NO: 27, SEQ ID NO: 29, SEQ ID NO: 31, SEQ ID NO: 33, SEQ ID NO: 35, SEQ ID NO: 37, SEQ ID NO: 41, or SEQ ID NO: 47. In some embodiments, a reverse primer or promoter primer hybridizes to SEQ ID NO: 80 and is capable of initiating DNA or RNA polymerization. In some embodiments, a reverse primer or promoter primer comprises an oligomer capable of competing with any of SEQ ID NO: 6, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 41, or SEQ ID NO: 47 for hybridizing to SEQ ID NO. 80.

In some embodiments, an RNA polymerase promoter sequence can be added to any of the described forward and/or reverse primers to form a promoter primer. The RNA polymerase primer sequence is functionally linked to the 5' end of the forward or reverse primer. An RNA polymerase promoter sequence can be, but is not limited to, a T7, a T3, or a SP6 RNA polymerase promoter sequence. A T7 RNA polymerase promoter sequence can contain the nucleotide sequence of SEQ ID NO: 78. In some embodiments, a promoter primer comprises or consists of the nucleotide sequence of: SEQ ID NO: 28, SEQ ID NO: 30, SEQ ID NO: 32, SEQ ID NO: 34, SEQ ID NO: 36, SEQ ID NO: 38, SEQ ID NO: 40 or SEQ ID NO: 46.

In some embodiments, a helper oligomer facilitates or enhances hybridization of a forward primer to a template nucleotide sequence. In some embodiments, a displacer oligomer facilitates or enhances hybridization of a reverse primer to a template nucleic acid sequence. Facilitating or enhancing hybridization of a primer to a template can facilitate or enhance amplification of the target nucleotide sequence. In some embodiments, helper oligomers and/or displacer oligomers may be blocked (i.e., non-extendable). When blocked, the helper and/or displacer oligomers are unable to prime polymerization from the 3' end. For example, the helper/displacer oligomer can be rendered non-extendable by 3'-phosphorylation, having a 3'-terminal 3'-deoxynucleotide (e.g., a terminal 2',3'-dideoxynucleotide), having a 3'-terminal inverted nucleotide (e.g., in which the last nucleotide is inverted such that it is joined to the penultimate nucleotide by a 3' to 3' phosphodiester linkage or analog thereof, such as a phosphorothioate), or having an attached fluorophore, quencher, or other label that interferes with extension (possibly but not necessarily attached via the 3' position of the terminal nucleotide). For any of the described helper oligomers, one or more nucleotides in the helper oligomer can be modified. In some embodiments, a helper oligomer contains a 3' inverted (reverse polarity) nucleotide. In some embodiments, the inverted nucleotide is an inverted dC.

In some embodiments, a helper oligomer comprises 19, 20, 21, 22, 23, 24, 25, 26, 27, 28, 29, 30, 31, or 19-31 contiguous nucleobases having at least 80% or at least 90% identity to a 19, 20, 21, 22, 23, 24, 25, 26, 27, 28, 29, 30, 31, or 19-31 nucleotide sequence present it SEQ ID NO: 2. In some embodiments, a helper oligomer comprises 19, 20, 21, 22, 23, 24, 25, 26, 27, 28, 29, 30, 31, or 19-31 contiguous nucleobases having a nucleotide sequence present in SEQ ID NO: 2. In some embodiments, a helper oligomer comprises the nucleotide sequence of SEQ ID NO: 10 or SEQ ID NO 19. In some embodiments, a helper oligomer comprises or consists of a nucleotide sequence selected from the group consisting of: SEQ ID NO: 14, SEQ ID NO: 15, SEQ ID NO: 17, SEQ ID NO: 18, and SEQ ID NO: 19. In some embodiments, an helper oligomer comprises a nucleotide sequence having 90% identity to SEQ ID NO: 14, SEQ ID NO: 15, SEQ ID NO: 17, SEQ ID NO: 18, or SEQ ID NO: 19. In some embodiments, a helper oligomer comprises an oligomer capable of competing with any of SEQ ID NO: 14, SEQ ID NO: 15, SEQ ID NO: 17, SEQ ID NO: 18, or SEQ ID NO: 19 for hybridizing to SEQ ID NO. 79.

In some embodiments, a displacer oligomer comprises 21, 22, 23, 24, 25, or 21-27 contiguous nucleobases having at least 90% identity to a 21, 22, 23, 24, 25, 26, 27 or 21-27 nucleotide sequence present it SEQ ID NO: 5. In some embodiments, a displacer oligomer comprises 21, 22, 23, 24, 25, 26, 27, or 21-27 contiguous nucleobases having a nucleotide sequence present in SEQ ID NO: 5. In some embodiments, a displacer oligomer comprises the nucleotide sequence of SEQ ID NO: 25, SEQ ID NO: 12, or SEQ ID NO: 41. In some embodiments, a displacer oligomer comprises or consists of a nucleotide sequence selected from the group consisting of: SEQ ID NO: 25, SEQ ID NO: 33, SEQ ID NO: 35, SEQ ID NO: 37, SEQ ID NO: 6, SEQ ID NO: 41 and SEQ ID NO: 12. In some embodiments, an displacer oligomer comprises a nucleotide sequence having 90% identity to SEQ ID NO: 25, SEQ ID NO: 33, SEQ ID NO: 35, SEQ ID NO: 37, SEQ ID NO: 6, SEQ ID NO: 41, or SEQ ID NO: 12. In some embodiments, a displacer oligomer comprises an oligomer capable of competing with any of SEQ ID NO: 25, SEQ ID NO: 33, SEQ ID NO: 35, SEQ ID NO: 37, SEQ ID NO: 6, SEQ ID NO: 41, or SEQ ID NO: 12 for hybridizing to SEQ ID NO. 82. For any of the described displacer oligomers, one or more nucleotides in the displacer oligomer can be modified. In some embodiments, a displacer oligomer contains a 3' inverted (reverse polarity) nucleotide. In some embodiments, the inverted nucleotide is an inverted dC.

In some embodiments, a helper or displacer oligomer can be a forward primer or reverse primer. In some embodiments, a described helper oligomer or displacer oligomer can have an RNA polymerase promoter sequence linked to the 5' end of the helper/displacer oligomer to form a promoter primer.

In some embodiments, oligomers are provided that comprise detectable labels (label). Such oligomers can be used as probes (probe oligomers). A probe oligomer is used to detect the presence or absence of a CMV amplification product made using the described amplification oligomers.

A probe oligomer can be used to detect a CMV amplicon, i.e., the probe oligomer hybridizes to the CMV amplicon. The CMV amplicon can be generated using any of the described amplification oligomers. In some embodiments, a probe oligomer comprises 24, 25, 26, 27, 28, 29, 30, 31, 32, 33, 34, or 24-35 contiguous nucleobases having at least 90% identity to a 24, 25, 26, 27, 28, 29, 30, 31, 32, 33, 34, or 24-35 nucleotide sequence present in SEQ ID NO: 4. In some embodiments, a probe oligomer comprises 24-35 contiguous nucleobases having a nucleotide sequence present in SEQ ID NO: 4. In some embodiments, a probe oligomer comprises 24-35 contiguous nucleobases that hybridize to SEQ ID NO: 81. In some embodiments, a probe oligomer comprises the nucleotide sequence of SEQ ID NO: 51 or SEQ ID NO: 52, wherein one or more uracil nucleotides can be substituted for thymine nucleotides. In some embodiments, a probe oligomer comprises a nucleotide sequence selected from the group consisting of: SEQ ID NO: 53, SEQ ID NO: 55, SEQ ID NO: 57, SEQ ID NO: 59, SEQ ID NO: 61, SEQ ID NO: 65, SEQ ID NO: 67, SEQ ID NO: 69, SEQ ID NO: 71, SEQ ID NO: 21, SEQ ID NO: 26, or SEQ ID NO: 39. In some embodiments, a probe oligomer contains a hairpin. In some embodiments, 4-5 nucleobases at the 5' and 3' ends of the probe oligomer are complementary to each other. In some embodiments, a probe oligomer comprises a nucleobase sequence selected from the group consisting of: SEQ ID NO: 20, SEQ ID NO: 22, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and SEQ ID NO: 70. In some embodiments, a probe oligomer comprises a nucleobase sequence having at least 90% identity to SEQ ID NO: 20, SEQ ID NO: 22, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, or SEQ ID NO: 70.

In some embodiments, the detectable label is a non-nucleotide label. Suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see. e.g., U.S. Pat. Nos. 6,180,340 and 6,350,579, each incorporated by reference herein). Labels may be attached to a probe by various means including covalent linkages, chelation, and ionic interactions, but in some embodiments the label is covalently attached. For example, in some embodiments, a detection probe has an attached chemiluminescent label such as, e.g., an acridinium ester (AE) compound (see. e.g., U.S. Pat. Nos. 5,185,439; 5,639,604; 5,585,481; and 5,656,744). A label, such as a fluorescent or chemiluminescent label, can be attached to the probe by a non-nucleotide linker (see. e.g., U.S. Pat. Nos. 5,585,481; 5,656,744; and 5,639,604). In some embodiments, a detection oligomer comprises a base spacer between the 5' end of the oligonucleotide and the label.

In some embodiments, a probe (e.g., comprising a fluorescent label) further comprises a second label that interacts with the first label. For example, the second label can be a quencher. Such probes can be used, e.g., in TaqMan™ assays, where hybridization of the probe to a target or amplicon followed by nucleolysis by a polymerase comprising 5'-3' exonuclease activity results in liberation of the fluorescent label and thereby increased fluorescence, or fluorescence independent of the interaction with the second label.

In some applications, one or more probes exhibiting at least some degree of self-complementarity are used to facilitate detection of probe:target duplexes in a test sample without first requiring the removal of unhybridized probe prior to detection. Some embodiments of such detection probes include, for example, probes that form conformations held by intramolecular hybridization, such as conformations generally referred to as hairpins. Suitable hairpin probes include a "molecular torch" (also termed Torch) (see. e.g., U.S. Pat. Nos. 6,849,412; 6,835,542; 6,534,274; and 6,361,945) and a "molecular beacon" (see. e.g., U.S. Pat. Nos. 5,118,801 and 5,312,728). The spacer (or linker) can be an alkyl group. In some embodiments, a torch contains a 5-6 nucleotide sequence at the 3' end that is complementary to and can hybridize with a 5-6 nucleotide sequence at the 5' end. In some embodiments, the 5-6 nucleotide sequence at the 3' end that is complementary to and can hybridize with 5-6 nucleotide at the 5' end linked to the torch via a linker. In some embodiments, the linker is a C1-16 linker. In some embodiments, the linker is a C9 linker. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. In some embodiments, a torch contains a fluorescent molecule attached to the 5' end and a quencher attached to the 3' end. Alternatively, a fluorescent molecule can be attached to the 3' end of the torch and a quencher attached to the 5' end of the detection oligomer.

Examples of interacting donor/acceptor label pairs that may be used in connection with the disclosure, making no attempt to distinguish FRET from non-FRET pairs, include, but are not limited to, fluorescein/tetramethylrhodamine, IAEDANS/fluorescein, EDANS/DABCYL, coumarin/DABCYL, fluorescein/fluorescein, BODIPY FL/BODIPY FL, fluorescein/DABCYL, CalRed-610/BHQ-2, lucifer yellow/DABCYL, Quasar 750/BHQ-2, BODIPY/DABCYL, eosine/DABCYL, erythrosine/DABCYL, tetramethyl-rhodamine/DABCYL, Texas Red/DABCYL, CY5/BHQ1, CY5/BHQ2, CY3/BHQ1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. Non-fluorescent acceptors such as DABCYL and the QSY7 dyes advantageously eliminate the potential problem of background fluorescence resulting from direct (i.e., non-sensitized) acceptor excitation. Exemplary fluorophore moieties that can be used as one member of a donor-acceptor pair include fluorescein, ROX, and the CY dyes (such as CY5). Exemplary quencher moieties that can be used as another member of a donor-acceptor pair include DABCYL, Blackberry, and the BLACK HOLE QUENCHER moieties which are available from Glen Research, (Sterling, VA), Berry & Associates, Inc., (Dexter, Mich), and Biosearch Technologies, Inc., (Novato, Calif.).

In some embodiments, a labeled oligomer (e.g., probe) is non-extendable (i.e., it is blocked). For example, the labeled oligomer can be rendered non-extendable by 3'-phosphorylation, having a 3'-terminal 3'-deoxynucleotide (e.g., a terminal 2',3'-dideoxynucleotide), having a 3'-terminal inverted nucleotide (e.g., in which the last nucleotide is inverted such that it is joined to the penultimate nucleotide by a 3' to 3' phosphodiester linkage or analog thereof, such as a phosphorothioate), or having an attached fluorophore, quencher, or other label that interferes with extension (possibly but not necessarily attached via the 3' position of the terminal nucleotide). In some embodiments, the 3'-terminal nucleotide is not methylated.

In some embodiments, it may be desirable to isolate the target nucleic acid sequence prior to the first phase amplification. To this end, the sample may be contacted with a target capture oligomer (TCO) under conditions allowing hybridization of the TCO to a portion of the target nucleic acid sequence (TCO binding site). In some embodiments, the target nucleic acid is captured onto a solid support directly, for example by interaction with an immobilized capture probe. In some embodiments, the target nucleic acid is captured onto the solid support as a member of a molecule complex (pre-amplification hybrid), with the TCO bridging the target nucleic acid and the immobilized capture probe. In some embodiments, the solid support comprises a plurality of magnetic or magnetizable particles or beads that can be manipulated using a magnetic field. The step of isolating the target nucleic acid sequence can include washing the TCO: target nucleic acid sequence hybrid to remove undesired components that may interfere with subsequent amplification. The step of isolating the target nucleic acid sequence can also include washing the TCO:target nucleic acid sequence hybrid to substantially remove excess promoter primer that is not hybridized to the target nucleic acid.

In some embodiments, the step of isolating the target nucleic acid sequence includes contacting the sample with a promoter primer and a TCO under conditions allowing hybridization of the promoter primer and TCO to the target nucleic acid sequence. The portion of the target sequence targeted by the promoter primer may be different (e.g. non-overlapping) from the portion targeted by the TCO. The portion of the target sequence targeted by the promoter primer may fully or partially overlaps with, or even be identical to, the portion targeted by the TCO.

In some embodiments, one or more TCOs, one or more promoter primers, and optionally one or more displacer oligomers are provided in a target capture reagent (TCR mixture). The one or more promoter primers and optionally one or more displacer oligomers can be hybridized to one or more target nucleic acid sequences to form pre-amplification hybrids (along with the TCO(s)) and isolated along with the one or more target nucleic acid sequences during the target capture step. One advantage of this method is that by hybridizing the promoter primer(s) to the target nucleic acid sequence(s) during target capture, the captured nucleic acids can be washed to remove sample components, including unhybridized oligomers. In a multiphase amplification reaction, removing unhybridized promoter primers allows the first phase amplification to occur without interference from the excess promoter primers, thereby substantially reducing or eliminating problems common to multiplex reactions. In single phase multiplex amplification reactions, the primers can interfere with one another. Excess primers more readily misprime (hybridize to non-target nucleic acids) in uniplex and in multiplex reactions. In a multiplex reaction, where the various organisms each have their own rRNA and oligonucleotides, mispriming is a bigger concern. Multiphase amplification addresses these problems by hybridizing the promoter primer to its intended target under stringent conditions, then washing away the excess promoter primer. The resulting 1:1 primer/target ratio present in the first phase amplification reaction of a multiphase amplification can boost the population of target nucleic acids to a level that allows for the subsequence addition of excess primer while reducing the level of mispriming or the effects of any mispriming on amplification.

Any of the described oligomers can contain at least one modified nucleotide. The modified nucleotide can be, but is not limited to, 2'-O-methyl modified nucleotide, 2'-fluoro modified nucleotide, or a 5'-methyl cytosine. In some embodiments, the 2'-O-methyl modified nucleotide is a 2'-OMe ribonucleotide. In some embodiments, an oligomer comprises two or more modified nucleotides. In some embodiments, all of the nucleotides in an oligomer are modified. The two or more modified nucleotides may be the same or different. In some embodiments, any of the described oligomers can contain one or more 5'-methyl cytosine. An oligomer can have 1, 2, 3, 4, 5, 6, 7, or more 5'-methyl cytosines. In some embodiments, all cytosine nucleotides in an oligomer are 5'-methyl cytosine modified nucleotides. An oligomer can have 1, 2, 3, 4, 5, 6, 7, or more 2'-OMe ribonucleotides. In some embodiments, all nucleotides in an oligomer are 2'-OMe ribonucleotides. In some embodiments, thymidine nucleotides can be substituted for uridine nucleotides. In some embodiments, all thymidine nucleotides can be substituted for uridine nucleotides. In some oligomers, 5'-methyl-2'-deoxycytosine bases can be used to increase the stability of the duplex by raising the Tm by about 0.5°-1.3° C. for each 5'methyl-2'deoxycytosine incorporated in an oligonucleotide (relative to the corresponding unmethylated oligomer).

C. Multiphase Amplification

Disclosed are methods that use aspects of isothermal amplification systems that are generally referred to as "transcription-associated amplification", which amplify a target sequence by producing multiple transcripts from a nucleic acid template. Such methods generally use one or more amplification oligonucleotides, of which one provides an RNA polymerase promoter sequence, deoxyribonucleoside triphosphates (dNTPs), ribonucleoside triphosphates (NTPs), and enzymes with RNA polymerase and DNA polymerase activities to generate a functional promoter sequence near the target sequence and then transcribe the target sequence from the promoter (e.g., U.S. Pat. Nos. 4,868,105, 5,124,246, 5,130,238, 5,399,491, 5,437,990, 5,554,516 and 7,374,885; and PCT Pub. Nos. WO 1988/001302, WO 1988/010315 and WO 1995/003430). Examples include Transcription-Mediated Amplification (TMA), nucleic acid sequence based amplification (NASBA) and Self-Sustained Sequence Replication (3SR).

To aid in understanding of some of the embodiments disclosed herein, the TMA method that has been described in detail previously (e.g., U.S. Pat. Nos. 5,399,491, 5,554,516 and 5,824,518) is briefly summarized. In TMA, a target nucleic acid that contains the sequence to be amplified is provided as single stranded nucleic acid (e.g., ssRNA or ssDNA). Any conventional method of converting a double stranded nucleic acid (e.g., dsDNA) to a single-stranded nucleic acid may be used. A promoter primer (e.g., T7 primer) binds specifically to the target nucleic acid at its target sequence and a reverse transcriptase (RT) extends the 3' end of the promoter primer using the target strand as a template to create a cDNA copy, resulting in a RNA:cDNA duplex. RNase activity (e.g., RNase H of RT enzyme) digests the RNA of the RNA:cDNA duplex. A second primer (e.g., non-promoter primer or NT7 primer) binds specifically to its target sequence in the cDNA, downstream from the promoter-primer end. Then RT synthesizes a new DNA strand by extending the 3' end of the second primer using the cDNA as a template to create a dsDNA that contains a functional promoter sequence. RNA polymerase specific for the functional promoter initiates transcription to produce multiple (e.g., 100 to 1000) RNA transcripts (amplified copies or amplicons) complementary to the initial target strand. The second primer binds specifically to its target sequence in each amplicon and RT creates a cDNA from the amplicon RNA template to produce a RNA:cDNA duplex. RNase digests the amplicon RNA from the RNA:cDNA duplex and the target-specific sequence of the promoter primer binds to its complementary sequence in the newly synthesized DNA and RT extends the 3' end of the promoter primer as well as the 3' end of the cDNA to create a dsDNA that contains a functional promoter to which the RNA polymerase binds and transcribes additional amplicons that are complementary to the target strand. Autocatalytic cycles that use these steps repeatedly during the reaction produce amplification of the initial target sequence. Amplicons may be detected during amplification (real-time detection) or at an end point of the reaction (end-point detection) by using a probe that binds specifically to a sequence contained in the amplicons. Detection of a signal resulting from the bound probes indicates the presence of the target nucleic acid in the sample.

Described are methods of amplifying and/or detecting CMV using a multiphase amplification procedure. The methods comprise amplifying CMV target nucleic acid sequence in a sample including the following steps. Initially, the target nucleic acid sequence is subjected to a first phase amplification reaction under conditions that do not support exponential amplification of the target nucleic acid sequence. The first phase amplification reaction generates a first amplification product, which is subsequently subjected to a second phase amplification reaction under conditions allowing exponential amplification of the first amplification product, thereby generating a second amplification product.

In some embodiments, the portion of the target sequence targeted by the promoter primer (promoter primer binding site) may be different (e.g., non-overlapping) from the portion targeted by the TCO (if used). A promoter primer binding site may fully or partially overlap with, or be identical to, the TCO binding site. In some embodiments, the amplified region of the target sequence partially or completely overlaps the target capture binding site. In some embodiments, the amplified region of the target sequence does not overlap the target capture binding site.

In some embodiments, before the first amplification step, the sample is contacted with one or more promoter primers under conditions allowing hybridization of the promoter primer to a portion of the target nucleic acid sequence in the sample. The RNA polymerase promoter sequence of the promoter primer is recognized by an RNA polymerase, such as T7 RNA polymerase. The one or more promoter primers can target the same or different target nucleic acid sequences. The different target nucleic acid sequence can be from the same or different organisms.

The first phase amplification reaction is carried out under conditions that do not support exponential amplification of the target nucleic acid sequence. In some embodiments, the first phase amplification reaction is a linear amplification reaction. The first phase amplification reaction will typically produce from about 2-fold to about 10,000-fold amplification. In some embodiments, the first phase amplification reaction will produce about 10-fold to about 10,000-fold amplification of the target nucleic acid sequence. In some embodiments, the first phase amplification reaction is substantially isothermal, i.e., it does not involve thermal cycling characteristic of PCR and other popular amplification techniques. The first phase amplification reaction can be performed at 43±2° C., 43±1° C., 42±1° C., 42±0.5° C., 43±0.5° C., 44±0.5° C., 41-45° C., or 42-44° C.

In some embodiments, the first phase amplification reaction involves contacting the target nucleic acid sequence with a first phase amplification reaction mixture (e.g., AMP or AMP1 mixture) that supports linear amplification of the target nucleic acid sequence and lacks at least one component that is required for its exponential amplification. In some embodiments, at least one component that is required for its exponential amplification is additional or excess promoter primer. In some embodiments, the AMP or AMP1 reaction mixture comprises one or more amplification enzymes. The one or more amplification enzymes can be, but are not limited to: a DNA polymerase, an RNA polymerase, or a combination thereof. The DNA polymerase can be, but is not limited to, an RNA-dependent DNA polymerase (reverse transcriptase), a DNA-dependent DNA polymerase, or a combination thereof. In some embodiments, the AMP or AMP1 mixture comprises a ribonuclease (RNase), such as an RNase H or a reverse transcriptase with an RNase H activity. In some embodiments, the AMP or AMP1 mixture includes a reverse transcriptase with an RNase H activity and an RNA polymerase. The RNA polymerase can be, but is not limited to, a T7 RNA polymerase. In some embodiments, the AMP or AMP1 mixture contains one or more non-RNA polymerase promoter-containing amplification oligonucleotides (e.g., non-promoter primers (i.e., NT7 primers)). The one or more non-promoter primers can target the same or different target nucleic acid sequences. The different target nucleic acid sequence can be from the same or different organisms. In some embodiments, the AMP or AMP1 mixture comprises: one or more non-promoter primer(s), an RNA polymerase, ribonucleotide triphosphates (NTPs), and deoxyribonucleotide triphosphates (dNTPs). The AMP or AMP1 mixture may additionally contain other components, including, but not limited to, buffers, dNTPs, NTPs, and salts.

In some embodiments, the first phase amplification reaction is unable to support an exponential amplification reaction because one or more components required for exponential amplification are lacking, an agent is present which inhibits exponential amplification, and/or the temperature of the reaction mixture is not conducive to exponential amplification. Without limitation, the lacking one or more components required for exponential amplification and/or inhibitor and/or reaction condition can be selected from any of: an amplification oligonucleotide (e.g., a promoter primer, a non-promoter primer, or a combination thereof), an enzyme (e.g., a polymerase, such as an RNA polymerase), a nuclease (e.g., an exonuclease, an endonuclease, a cleavase, an RNase, a phosphorylase, a glycosylase, etc.), an enzyme co-factor, a chelator (e.g., EDTA or EGTA), ribonucleotide triphosphates (NTPs), deoxyribonucleotide triphosphates (dNTPs), Mg2+, a salt, a buffer, an enzyme inhibitor, a blocking oligonucleotide, pH, temperature, salt concentration, and any combination thereof. In some cases, the lacking component may be involved indirectly, such as an agent that reverses the effects of an inhibitor of exponential amplification which is present in the first phase reaction. In some embodiments, the lacking one or more components is a promoter primer (additional promoter primer in excess of the promoter primer hybridized to the target nucleic acid as part of the pre-amplification hybrid).

The second phase (or later phase, if there are more than 2 phases) amplification reaction is carried out under conditions that allow exponential amplification of the target nucleic acid sequence. In some embodiments, the second phase amplification reaction is an exponential amplification reaction. In some embodiments, the second phase amplification reaction is a substantially isothermal reaction, such as, for example, a transcription-associated amplification reaction or a strand displacement amplification reaction. In some embodiments, the second phase amplification reaction is a Transcription-Mediated Amplification (TMA) reaction. In some embodiments, the second phase amplification reaction is performed at 43±2° C., 43±1° C., 42±1° C., 42±0.5° C., 43±0.5° C., 44±0.5° C., 41-45° C., or 42-44° C.

In some embodiments, the second (or later) phase amplification comprises contacting the first amplification product with a second phase amplification reaction mixture (e.g., PRO or AMP2 mixture) which, in combination with the first phase amplification reaction mixture, supports exponential amplification of the target nucleic acid sequence. Thus, the second phase amplification reaction mixture typically includes, at a minimum, the one or more component(s) required for exponential amplification lacking in the first phase amplification reaction mixture. In some embodiments, the second phase amplification reaction mixture comprises one or more components selected from: an amplification oligonucleotide (such as a promoter primer), a reverse transcriptase, a polymerase, a nuclease, a phosphorylase, an enzyme co-factor, a chelator, ribonucleotide triphosphates (NTPs), deoxyribonucleotide triphosphates (dNTPs), Mg2+, an optimal pH, an optimal temperature, a salt and a combination thereof. The polymerase can be, but is not limited to, an RNA-dependent DNA polymerase (e.g., reverse transcriptase), a DNA-dependent DNA polymerase, a DNA-dependent RNA polymerase, and a combination thereof. In some embodiments, the second phase amplification reaction mixture comprises an RNase, such as an RNase H or a reverse transcriptase with an RNase H activity. In some embodiments, the second phase amplification reaction mixture includes a promoter primer, a reverse transcriptase with an RNase H activity, and/or an RNA polymerase. In some embodiments, the second phase amplification reaction mixture further comprises a detection oligo. The detection oligomer can be, but is not limited to, a Torch or molecular beacon.

In some embodiments, the Target Capture Reagent (TCR) contains one or more TCOs, one or more T7 promoter primers, and optionally one or more displacer oligomers; the AR (AMP or AMP1) reagent contains buffer, dNTP, NTP, salt, one or more nonT7 primers and optionally one or more helper oligomers; the promoter (PR or AMP2) reagent contains buffer, dNTP, NTP, salt, surfactant, one or more T7 promoter primers and one or more torch oligonucleotides, and the Enzyme (ENZ) reagent contains buffer, detergent, chelators, reverse transcriptase and DNA polymerase.

In some embodiments, the described methods further include a step of contacting the second amplification product with a bolus of one or more amplification components selected from, but not limited to, an amplification oligonucleotide (promoter primer or non-promoter primer), a reverse transcriptase (e.g., a reverse transcriptase with an RNase H activity), a polymerase (e.g., an RNA polymerase), a nuclease, a phosphorylase, an enzyme co-factor, a chelator, ribonucleotide triphosphates (NTPs), deoxyribonucleotide triphosphates (dNTPs), Mg2+, a salt and a combination thereof. This additional step can provide a boost to the second phase amplification reaction as some of the amplification reaction components may become depleted.

The present methods can be used to detect and/or quantify a CMV target nucleic acid sequence in a biological sample. The second phase amplification reaction can be a quantitative amplification reaction. Also described are methods for detecting the second amplification product. Detecting and/or quantifying the second amplification products may be done using a variety of detection techniques known in the art. Detection and/or quantifying can be accomplished by using, for instance, a detection probe, a sequencing reaction, electrophoresis, mass spectroscopy, melt curve analysis, or a combination thereof. In some embodiments, the second amplification product is detected and/or quantified using a detection probe. The detection probe can be, but is not limited to, a molecular torch (Torch, as described in U.S. Pat. No. 6,534,274), a molecular beacon, a hybridization switch probe, or a combination thereof. In some embodiments, the detection and/or quantification may be performed in real time. The detection probe may be included in the first and/or second phase amplification reactions with substantially equal degrees of success. The detection probe may be supplied in the first and/or second phase amplification reaction mixture (e.g., AMP or AMP1 mixture and/or PRO or AMP2 mixture). In some embodiments, the PRO mixture contains a detection probe. The detection probe can comprise a Torch.

D. Compositions and Kits

The present disclosure provides oligomers, compositions, and kits, useful for amplifying, detecting, and/or quantifying CMV in a sample. The oligomers, compositions, and kits can be used in thermal cycling and isothermal amplification methods, and single phase and/or multiphase amplification methods. In some embodiments, any oligomer combination described herein can be provided in a kit.

Reaction mixtures for determining the presence or absence of a CMV target nucleic acid or quantifying the amount thereof in a sample are described.

In some embodiments, a reaction mixture in accordance with the present disclosure comprises at least one or more of the following: an oligomer combination (amplification pair) and optionally a helper oligomer and/or displacer oligomer as described herein for amplification of a CMV UL56 gene target nucleic acid and a detection probe oligomer as described herein for determining the presence or absence of a CMV amplification product. In some embodiments, various reaction mixtures include one or more of: Target capture (TCR) mixture, Amplification (AR or AMP1) mixture, promoter (PR or AMP2) mixture, and enzyme (ENZ) mixture.

A reaction mixture may independently comprise one or more of: promoter primer (e.g., T7 primer), non-promoter primer (NT7 oligonucleotide), helper oligomer, displacer oligomer, TCO, detection oligomer, reverse transcriptase, RNA polymerase, dNTPs, NTPs, buffers, salts, and combinations thereof, as described herein for amplification and/or detection of a CMV target nucleic acid in a sample. A kit can comprise, for example, one or more or a TER, a TCR, an AMP1 (AR) mix, and/or an AMP2 (PR) mix, each as describe herein.

In some embodiments, a kit includes one or more control oligonucleotides, including, but not limited to, control TCO, control promoter primer, control non-promoter primer, control detection oligomer, and combinations thereof. A kit may include oligonucleotides for amplification and detection of CMV, or it may oligonucleotides for amplification and detection CMV and one or more other organisms A composition, kit and/or reaction mixture may further include a number of optional components such as, for example, target capture probes, (including, but not limited to poly-(K) capture probes as described in US 2013/0209992, which is incorporated herein by reference and poly(A)-containing capture probes). In some embodiments, a kit, composition, or reaction mixture(s) additionally contains one or more of: enzyme(s) (e.g., a thermostable DNA polymerase, reverse transcriptase and/or RNA polymerase), positive control nucleic acid, negative control nucleic acid, control nucleic acid, dNTPs (e.g. dATP, dTTP, dGTP, and dCTP), NTPs (e.g. ATP, UTP, GTP, and CTP), Cl, MgCl2, potassium acetate, buffer, BSA, sucrose, trehalose, DMSO, betaine, formamide, glycerol, polyethylene glycol, non-ionic detergents, ammonium ions, EDTA, and other reagents or buffers suitable for isothermal amplification and/or detection. The DNA polymerase can be, but is not limited to, reverse transcriptase. The buffer can be, but is not limited to, Tris-HCl and Tris-acetate. The nonionic detergent can be, but is not limited to, Tween-20 and Triton X-100. A reaction mixture may include amplification oligomers for only one target region of a CMV genome, or it may include amplification oligomers for multiple CMV target regions. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

In some embodiments, the reaction mixture comprises KCl. In some embodiments, the KCl concentration is about 50 mM. In some embodiments, the KCl concentration is greater than about 50 mM, e.g., about 60-150 mM, about 75-125 mM, about 80-120 mM, about 85-115 mM, or about 90-110 mM. In some embodiments, the KCl concentration is 55-65, 65-75, 75-85, 85-95, 95-105, 105-115, 115-125, 125-135, or 135-145, wherein each of the foregoing is in mM and is optionally modified by "about". In some embodiments, a composition according to the disclosure comprises KCl, e.g., at any of the foregoing concentrations. In some embodiments, a method according to the disclosure comprises performing an amplification reaction in the presence of KCl, e.g., at any of the foregoing concentrations.

In some embodiments, the described oligomers for amplification and/or detection CMV have a shelf-life of at least 3 months, at least 6 months, at least 9 months, at least 12 months, at least 15 months, at least 18 months, or at least 24 months from date of manufacture.

In some embodiments, oligomers are provided, e.g., in a kit or composition. Oligomers generally comprise a target-hybridizing region, e.g., configured to hybridize specifically to a CMV nucleic acid. While oligomers of different lengths and base composition may be used for amplifying CMV nucleic acids, in some embodiments oligomers in this disclosure have target-hybridizing regions from about 19-40 bases in length or about 19, 20, 21, 22, 23, 24, 25, 26, 27, 28, 29, 30, 31, 32, 33, 34, 35, 36, 37, 38, 39, or 40 bases in length. In some embodiments, an oligomer comprises a second region of sequence in addition to the target-hybridizing region, such as a T7 RNA polymerase promoter, which can be located 5' of the target-hybridizing region. In some embodiments, an oligomer does not comprise a second region of sequence.

In some embodiments, a pair of oligomers is provided wherein one oligomer is configured to hybridize to a sense strand of a CMV nucleic acid and the other is configured to hybridize to an anti-sense strand of a CMV nucleic acid. Such oligomers include primer pairs for PCR, transcription-mediated amplification, or other forms of amplification known in the art.

In some embodiments, one or more oligomers, such as a primer pair or a primer pair and a third oligomer which is optionally labeled (e.g., for use as a probe), are configured to hybridize to a CMV UL56 gene. In some embodiments, one or more oligomers, such as a primer pair or a primer pair and a third oligomer which is optionally labeled (e.g., for use as a probe), are configured to hybridize to a CMV sequence represented by SEQ ID NO: 1 and/or a complement thereof. In some embodiments, one or more internal control probe oligomers are also provided.

In some embodiments, one or more oligomers comprise a degenerate position. In some embodiments, a described oligomer comprises a degenerate position. In some embodiments, one or more oligomers comprise a non-Watson Crick (NWC) position. In some embodiments, an oligomer comprises an NWC position. Exemplary NWC positions include U residues in various exemplary oligomers in the Table 1A-E.

In some embodiments, one or more oligomers in a set, kit, composition, or reaction mixture comprise a methylated cytosine (e.g., 5-methylcytosine). In some embodiments, an oligomer contains 1, 2, 3, 4, 5 or more methylated cytosines. In some embodiments, at least about half of the cytosines in an oligomer are methylated. In some embodiments, all or substantially all (e.g., all but one or two) of the cytosines in an oligomer are methylated. In some embodiments, a cytosine at the 3' end or within 2, 3, 4, or 5 bases of the 3' end is unmethylated.

In some embodiments, a composition or kit comprises a probe oligomer that comprises torch or beacon. Each torch has a fluorophore and a quencher: for example, 6'-carboxy-X-rhodamine (ROX) with Acridine Quencher for the IC torch, and Fluorescein (FAM) with dabcyl quencher for CMV. The fluorophores associated with the CMV and IC targets emit light at different wavelengths, thus allowing these targets to be distinguished from one another.

Additional components or reaction mixtures, compositions, and/or kits include, but are not limited to, capture beads, Target Capture Reagent, Target Capture Wash Solution, Target Enhancer Reagent, Amplification Reagent (lyophilized cake), Amplification Reagent Reconstitution Solution, Enzyme Reagent (lyophilized cake), Enzyme Reagent Reconstitution Solution, Promoter Reagent (lyophilized cake), Promoter Reagent Reconstitution Solution, Positive Calibrator, CMV positive control nucleic acid, negative control nucleic acid, and/or Sample Transport Medium. In certain embodiments, a kit further includes a set of instructions for practicing methods in accordance with the present disclosure, where the instructions may be associated with a package insert and/or the packaging of the kit or the components thereof.

Any method disclosed herein is also to be understood as a disclosure of corresponding uses of materials involved in the method directed to the purpose of the method. Any of the oligomers comprising CMV sequence and any combinations (e.g., kits and compositions) comprising such an oligomer are to be understood as also disclosed for use in detecting and/or quantifying CMV or in amplifying a CMV UL56 gene sequence, and for use in the preparation of a composition for detecting and/or quantifying CMV, or in amplifying a CMV UL56 gene sequence.

E. Methods of Amplifying, Detecting and or Quantifying CMV

Described of methods of detecting and/or quantifying CMV or in amplifying a CMV UL56 gene sequence using one or more of the oligomers, compositions, or kits as described above.

Broadly speaking, the methods can comprise one or more of the following components: target capture, in which CMV nucleic acid (e.g., from a sample, such as a clinical sample) is annealed to a TCO; isolation, e.g., washing, to remove material not associated with a capture oligomer; amplification; and amplicon detection, e.g., amplicon quantification, which may be performed in real time with amplification. Certain embodiments involve each of the foregoing steps. Certain embodiments involve exponential amplification, optionally with a preceding linear amplification step. Certain embodiments involve exponential amplification and amplicon detection. Certain embodiments involve any two of the components listed above. Certain embodiments involve any two components listed adjacently above, e.g., washing and amplification, or amplification and detection.

In some embodiments, amplification comprises contacting the sample with at least two oligomers for amplifying a CMV nucleic acid target region corresponding to a CMV target UL56 gene nucleic acid, wherein the oligomers include at least two amplification oligomers as described above (e.g., one or more primers oriented in the sense direction and one or more primers oriented in the antisense direction for exponential amplification); (2) performing an in vitro nucleic acid amplification reaction, where any CMV target nucleic acid present in the sample is used as a template for generating an amplification product; and (3) detecting the presence or absence of the amplification product, thereby determining the presence or absence of CMV in the sample, or quantifying the amount of CMV nucleic acid in the sample.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the CMV target nucleic acid from other components in the sample, e.g., before an amplification, such as before a capture step. Such purification may include methods of separating and/or concentrating organisms contained in a sample from other sample components, or removing or degrading non-nucleic acid sample components, e.g., protein, carbohydrate, salt, lipid, etc. In some embodiments, DNA in the sample is degraded, e.g., with DNase, and optionally removing or inactivating the DNase or removing degraded DNA.

In some embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains CMV nucleic acid and other sample components.

Target capture typically occurs in a solution phase mixture that contains one or more TCOs that hybridize to the CMV target sequence under hybridizing conditions. For embodiments comprising a TCO, the CMV-target:TCO complex is captured by adjusting the hybridization conditions so that the TCO tail hybridizes to an immobilized probe. Certain embodiments use a particulate solid support, such as paramagnetic beads. In some embodiments, a promoter primer is present during capture. Hybridization conditions are adjusted to allow for isolation and purification of a pre-amplification hybrid.

Isolation can follow capture, wherein the complex on the solid support is separated from other sample components. Isolation can be accomplished by any appropriate technique, e.g., washing a support associated with the CMV-target-sequence one or more times (e.g., 2 or 3 times) to remove other sample components and/or unbound oligomer. In embodiments using a particulate solid support, such as paramagnetic beads, particles associated with the CMV target may be suspended in a washing solution and retrieved from the washing solution by magnetic attraction. To limit the number of handling steps, the CMV target nucleic acid may be amplified by simply mixing the CMV target sequence in the complex on the support with amplification oligomers and proceeding with amplification steps.

Exponentially amplifying a CMV target sequence utilizes an in vitro amplification reaction using at least two amplification oligomers that flank a target region to be amplified. In some embodiments, at least first (forward) and second (reverse) oligomers as described above are used to amplify the target sequence. The amplification reaction can be thermal cycled or isothermal. Suitable amplification methods include, but are not limited to, replicase-mediated amplification, polymerase chain reaction (PCR), ligase chain reaction (LCR), strand-displacement amplification (SDA), and transcription-mediated or transcription-associated amplification (TMA).

A detection step may be performed using any of a variety of known techniques to detect a signal specifically associated with the amplified target sequence, such as, e.g., by hybridizing the amplification product with a labeled detection probe and detecting a signal resulting from the labeled probe (including from label released from the probe following hybridization in some embodiments). In some embodiments, the labeled probe comprises a second moiety, such as a quencher or other moiety that interacts with the first label, as discussed above. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In some embodiments, the detection step allows homogeneous detection, e.g., detection of the hybridized probe without removal of unhybridized probe from the mixture (see. e.g., U.S. Pat. Nos. 5,639,604 and 5,283,174). In some embodiments, the nucleic acids are associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the CMV UL56 gene, and a probe will bind directly or indirectly to a sequence contained in the amplified product to indicate the presence of CMV nucleic acid in the tested sample.

In some embodiments that detect the amplified product near or at the end of the amplification step, a linear detection probe may be used to provide a signal to indicate hybridization of the probe to the amplified product. One example of such detection uses a luminescentally labeled probe that hybridizes to target nucleic acid. Luminescent label is then hydrolyzed from non-hybridized probe. Detection is performed by chemiluminescence using a luminometer (see, e.g., International Patent Application Pub. No. WO 89/002476). In some embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences.

In some embodiments, detection is performed at time intervals. Detection can be done by measuring fluorescence at regular time intervals. Time intervals can be, but are not limited to: 1-60 sec, 1-120 sec, 1-180 sec, 1-240 sec, or 1-300 sec. In some embodiments, the time interval is 5, 10, 15, 20, 25, 30, 35, 40, 45, 50, 55, or 60 sec. For detection performed at regular time intervals, each interval is referred to as a cycle. Detection can be performed for 20-240 cycles, 30-210 cycles, 40-180 cycles, 50-150 cycles, or 60-120 cycles. For example, detection every 30 sec for 60 minutes constitutes 120 cycles. Detection may occur at the beginning or end of a cycle. Detection can also be performed continuously.

Embodiments of the compositions and methods described herein may be further understood by the examples that follow. Method steps used in the examples have been described herein and the following information describes typical reagents and conditions used in the methods with more particularity. Other reagents and conditions may be used that will not substantially affecting the process or results so long as guidance provided in the description above is followed. Moreover, the disclosed methods and compositions may be performed manually or in a system that performs one or more steps (e.g., pipetting, mixing, incubation, and the like) in an automated device or used in any type of known device (e.g., test tubes, multi-tube unit devices, multi-well devices such as 96-well microtiter plates, and the like).

F. Listing of Embodiments

1. A kit for amplifying a target region of nucleic acid derived from a human cytomegalovirus (CMV) UL56 gene sequence comprising: (a) a forward primer comprising 19-31 contiguous nucleobases having at least 90% identity to a 19-31 nucleotide sequence present in SEQ ID NO: 2; and (b) a reverse primer comprising 21-40 contiguous nucleobases having at least 90% identity to a 21-40 nucleotide sequence present in SEQ ID NO: 3.

2. The kit of embodiment 1 wherein the forward primer, the reverse primer, or both the forward primer and the reverse primer comprise at least one modified nucleotide.

3. The kit of embodiment 2, wherein the modified nucleotide comprises a 2'-O-methyl modified nucleotide, a 2'-Fluoro modified nucleotide, or a 5'-methyl cytosine.

4. The kit of any one of embodiments 1-3 wherein the forward primer comprises the nucleobase sequence of SEQ ID NO: 10, SEQ ID NO: 11, or SEQ ID NO: 19.

5. The kit of any embodiment 4, wherein the forward primer is a non-promoter primer comprising the nucleobase sequence of SEQ ID NO: 11, SEQ ID NO: 13, SEQ ID NO: 14, SEQ ID NO: 15, SEQ ID NO: 17, SEQ ID NO: 18, or SEQ ID NO: 19.

6. The kit of any one of embodiments 1-5, wherein the reverse primer comprises the nucleobase sequence of SEQ ID NO: 23, SEQ ID NO: 24, or SEQ ID NO: 25.

7. The kit of embodiment 6 wherein the reverse primer comprises the nucleobase sequence of SEQ ID NO: 6, SEQ ID NO: 23, SEQ ID NO: 27, SEQ ID NO: 29, SEQ ID NO: 31, SEQ ID NO: 33, SEQ ID NO: 35, SEQ ID NO: 37, SEQ ID NO: 41, SEQ ID NO: 47.

8. The kit of any one of embodiment 1-4 or 6-7, wherein an RNA polymerase promoter sequence is linked to the 5' end of the forward primer or the reverse primer.

9. The kit of embodiment 8, wherein the RNA polymerase promoter sequence is a T7 RNA polymerase promoter sequence.

10. The kit of embodiment 9, wherein the T7 RNA polymerase promoter sequence comprises the nucleotide sequence of SEQ ID NO: 78.

11. The kit of embodiments 10 wherein the reverse primer comprises the nucleobase sequence of SEQ ID NO: 28, SEQ ID NO: 30, SEQ ID NO: 32, SEQ ID NO: 34, SEQ ID NO: 36, SEQ ID NO: 38, SEQ ID NO: 40 or SEQ ID NO: 46.

12. The kit of any one of embodiments 1-10 wherein the forward primer comprises SEQ ID NO: 11 and the reverse primer comprises SEQ ID NO: 23.

13. The kit of any one of embodiments 1-12, further comprising a probe oligomer.

14. The kit of embodiment 13, wherein the probe oligomer comprises (a) a nucleobase sequence of SEQ ID NO: 51 or SEQ ID NO: 52, wherein one or more uracil nucleotides can be substituted for thymine nucleotides or (b) a nucleotide sequence comprising 24-35 contiguous nucleobases that hybridizes to SEQ ID NO: 81.

15. The kit of embodiment 14, wherein the probe oligomer comprises at least one modified nucleotide.

16. The probe oligomer of embodiment 15, wherein the modified nucleotide comprises a 2'-O-methyl modified nucleotide, a 2'-Fluoro modified nucleotide, or a 5'-methyl cytosine.

17. The kit of any one of embodiments 14-16, wherein the probe oligomer comprises a nucleobase sequence of SEQ ID NO: 21, SEQ ID NO: 26, SEQ ID NO: 39, SEQ ID NO: 53, SEQ ID NO: 55, SEQ ID NO: 57, SEQ ID NO: 59, SEQ ID NO: 61, SEQ ID NO: 65, SEQ ID NO: 67, SEQ ID NO: 69, or SEQ ID NO: 71.

18. The kit of any one of embodiments 14-17, wherein the probe oligomer contains a detectable label.

19. The kit of embodiment 18, wherein the detectable label comprises a fluorescent molecule.

20. The kit of embodiment 19, wherein the fluorescent molecule is attached to the 5' or 3' end of the probe oligomer.

21. The kit of any one of embodiments 14-20, wherein the probe oligomer contains 4-5 nucleobases at the 3' end of the probe oligomer that are complementary to 4-5 nucleobase at the 5' end of the probe oligomer.

22. The kit of embodiment 21, wherein a fluorescent molecule is attached to the 5' end of the probe oligomer and a quencher is attached to the 3' end of the probe oligomer or a fluorescent molecule is attached to the 3' end of the probe oligomer and a quencher is attached to the 5' end of the probe oligomer.

23. The kit of embodiment 22, wherein the probe oligomer comprises the nucleobase sequence of SEQ ID NO: 20, SEQ ID NO: 22, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, or SEQ ID NO: 70.

24. The kit of any one of embodiments 14-22, wherein the forward primer comprises SEQ ID NO: 11, the reverse primer comprises SEQ ID NO: 23, and the probe oligonucleotide comprises SEQ ID NO: 53.

25. The kit of any one of embodiments 1-24, further comprising: a helper oligomer comprising 19-31 contiguous nucleobases having at least 90% identity to a 19-31 nucleotide sequence present in SEQ ID NO: 2.

26. The kit of embodiment 25, wherein the helper oligomer is blocked.

27. The kit of embodiment 25 or 26, wherein the helper oligomer comprises the nucleotide sequence of SEQ ID NO: 10 or SEQ ID NO: 19.

28. The kit of embodiment 27, wherein the helper oligomer comprises a nucleotide sequence selected from the group consisting of: SEQ ID NO: 14, SEQ ID NO: 15, SEQ ID NO: 17, SEQ ID NO: 18, SEQ ID NO: 19.

29. The kit of any one of embodiments 1-28, further comprising a displacer oligomer comprising 21-27 contiguous nucleobases having at least 90% identity to a 21-25 nucleotide sequence present in SEQ ID NO: 5.

30. The kit of embodiment 29, wherein the displacer oligomer comprises the nucleotide sequence of SEQ ID NO: 12, SEQ ID NO: 25, or SEQ ID NO: 41.

31. The kit of embodiment 30, wherein the displacer oligomer comprises a nucleotide sequence selected from the group consisting of: SEQ ID NO: 6, SEQ ID NO: 12, SEQ ID NO: 33, SEQ ID NO: 35, SEQ ID NO: 37, SEQ ID NO: 41, SEQ ID NO: 72, SEQ ID NO: 73, SEQ ID NO: 74, SEQ ID NO: 75, SEQ ID NO: 76, SEQ ID NO: 77, SEQ ID NO: 86, SEQ ID NO: 87, and SEQ ID NO: 88.

32. The kit of any one of embodiments 1-31, further comprising a target capture oligomer (TCO) comprising the nucleotide sequence of SEQ ID NO: 6, SEQ ID NO: 8, SEQ ID NO: 43, or SEQ ID NO: 45.

33. The kit of embodiment 32, wherein the TCO contains a moiety that enables isolation of the TCO.

34. The kit of embodiment 33, wherein the moiety comprises a polyA nucleotide sequence.

35. The kit of embodiment 33, wherein the moiety comprises (dT)3(dA)30.

36. The kit of embodiment 35 wherein the TCO comprises the nucleotide sequence of SEQ ID NO: 7, SEQ ID NO: 9, SEQ ID NO: 42, or SEQ ID NO:44.

37. The kit of any one of embodiments 32-36, wherein the kit comprises a first TCO comprising the nucleotide sequence of SEQ ID NO: 42 and a second TCO comprising the nucleotide sequence SEQ ID NO: 44.

38. The kit of any one of embodiments 1-37, further comprising one or more of: Target Capture Reagent, Target Capture Wash Solution, Target Enhancer Reagent, Amplification Reagent, Enzyme Reagent, Promoter Reagent, CMV positive control nucleic acid, negative control nucleic acid, Sample Transport Medium, a reverse transcriptase, an RNA polymerase, dNTPs, NTPs, buffer, and positive and/or negative control samples.

39. A method for amplifying a target region of nucleic acid derived from a human cytomegalovirus (CMV) UL56 gene sequence present in a sample, the method comprising:

(a) contacting the sample with a forward primer and a reverse primer configured to amplify a CMV UL56 amplicon, wherein the forward primer comprises 19-31 contiguous nucleobases having at least 90% identity to a 19-31 nucleotide sequence present in SEQ ID NO: 2, and the reverse primer comprises 21-40 contiguous nucleobases having at least 90% identity to a 21-40 nucleotide sequence present in SEQ ID NO: 3; and, (b) exposing the sample to conditions sufficient to amplify the target region thereby producing an amplification product.

40. The method of embodiment 39, wherein the forward primer and/or the reverse primer comprises at least one modified nucleotide.

41. The method of embodiment 40, wherein the at least one modified nucleotide comprises a 2'-O-methyl modified nucleotide, a 2'-Fluoro modified nucleotide, or a 5'-methyl cytosine.

42. The method of any one of embodiments 39-41, wherein the forward primer comprises the nucleobase sequence of SEQ ID NO: 10, SEQ ID NO: 11, or SEQ ID NO: 19; and the reverse primer comprises the nucleobase sequence of SEQ ID NO: 23, SEQ ID NO: 24, SEQ ID NO: 25, or SEQ ID NO: 47.

43. The method of embodiment 42, wherein the forward primer comprises the nucleobase sequence of SEQ ID NO: 11, SEQ ID NO: 13, SEQ ID NO: 14, SEQ ID NO: 15, SEQ ID NO: 17, SEQ ID NO: 18, or SEQ ID NO: 19, and the reverse primer comprises the nucleobase sequence of SEQ ID NO: 6, SEQ ID NO: 23, SEQ ID NO: 27, SEQ ID NO: 29, SEQ ID NO: 31, SEQ ID NO: 33, SEQ ID NO: 35, SEQ ID NO: 37, SEQ ID NO: 41, SEQ ID NO: 47.

44. The method of embodiment 43, wherein a T7 RNA polymerase promoter sequence is linked to the 5' end of the reverse primer.

45. The method of embodiment 44, wherein the reverse primer comprises the nucleobase sequence of SEQ ID NO: 28, SEQ ID NO: 30, SEQ ID NO: 32, SEQ ID NO: 34, SEQ ID NO: 36, SEQ ID NO: 38, SEQ ID NO: 40 or SEQ ID NO: 46.

46. The method of any one of embodiments 39-43, wherein the forward primer comprises SEQ ID NO: 11 and the reverse primer comprises SEQ ID NO: 23.

47. The method of any one of embodiments 39-46, further comprising detecting the presence or absence of the amplification product.

48. The method of embodiment 47, wherein detecting the presence of absence of the amplification product utilizes a probe oligomer that specifically hybridizes to the amplification product.

49. The method of embodiment 48, wherein the probe oligomer comprises the nucleobase sequence of SEQ ID NO: 51 or SEQ ID NO: 52, wherein one or more uracil nucleotides can be substituted for thymine nucleotides or (b) a nucleotide sequence comprising 24-35 contiguous nucleobases that hybridizes to SEQ ID NO: 81.

50. The method of embodiment 49, wherein the probe oligomer comprises the nucleobase sequence of SEQ ID NO: 21, SEQ ID NO: 26, SEQ ID NO: 39, SEQ ID NO: 53, SEQ ID NO: 55, SEQ ID NO: 57, SEQ ID NO: 59, SEQ ID NO: 61, SEQ ID NO: 65, SEQ ID NO: 67, SEQ ID NO: 69, or SEQ ID NO: 71.

51. The method of any one of embodiments 48-50, wherein the probe oligomer contains 4-5 nucleobases at the 3' end of the probe oligomer that are complementary to 4-5 nucleobase at the 5' end of the probe oligomer.

52. The method of embodiment 51, wherein a fluorescent molecule is attached to the 5' end of the probe oligomer and a quencher is attached to the 3' end of the probe oligomer or a fluorescent molecule is attached to the 3' end of the probe oligomer and a quencher is attached to the 5' end of the probe oligomer.

53. The method of embodiment 52, wherein the probe oligomer comprises the nucleobase sequence of SEQ ID NO: 20, SEQ ID NO: 22, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, or SEQ ID NO: 70.

54. The method of any one of embodiments 39-44 and 46-53, wherein the forward primer comprises SEQ ID NO: 11, the reverse primer comprises SEQ ID NO: 23, and the probe oligonucleotide comprises SEQ ID NO: 53.

55. The method of any one of embodiments 39-54, wherein the amplifying comprises a thermal cycling reaction.

56. The method of embodiment 55, wherein the thermal cycling reaction comprises a polymerase chain reaction (PCR).

57. The method of any one of embodiments 39-54, wherein amplifying comprises an isothermal nucleic acid amplification reaction.

58. The method of embodiment 57, wherein the isothermal nucleic acid amplification reaction comprises transcription-mediated amplification (TMA).

59. The method of any one of embodiments 39-54, wherein the amplifying comprises nucleic acid sequence-based amplification, replicase-mediated amplification, QP-replicase-mediated amplification, ligase chain reaction (LCR), or strand-displacement amplification (SDA).

60. The method of any one of embodiments 47-59, wherein detecting the presence or absence of the amplified CMV UL56 amplicon further comprises quantifying the amplified CMV UL56 amplicon.

61. The method of embodiment 60, wherein quantifying the amplified CMV UL56 amplicon comprises monitoring production of the CMV amplicon.

62. The method of any one of embodiments 47-61, wherein detecting and/or quantifying is analyzed in real time.

63. A method of quantifying a human cytomegalovirus (CMV) UL56 gene target nucleic acid sequence in a sample comprising:

(a) contacting the sample with at least one target capture oligomer (TCO) comprising the nucleobase sequence of SEQ ID NO: 43 or SEQ ID NO: 45 and a first promoter primer comprising the nucleobase sequence of SEQ ID NO: 47 under conditions allowing hybridization of the at least one TCO and first promoter primer to the CMV UL56 gene target nucleic acid sequence, thereby generating a pre-amplification hybrid comprising target nucleic acid sequence hybridized to each of the at least one TCO and the first promoter primer;

(b) isolating the pre-amplification hybrid by target capture onto a solid support followed by washing to remove any of the first promoter primer that did not hybridize to the CMV UL56 gene target nucleic acid sequence in step (a);

(c) amplifying, in a first phase amplification reaction mixture comprising a non-promoter primer comprising the nucleobase sequence of SEQ ID NO: 19, at least a portion of the CMV UL56 gene target nucleic acid sequence of the pre-amplification hybrid isolated in step (b) in a first phase, substantially isothermal, transcription-associated amplification reaction under conditions that support linear amplification thereof, but do not support exponential amplification thereof, thereby resulting in a reaction mixture comprising a first amplification product, wherein the first amplification product is not a template for nucleic acid synthesis during the first phase, substantially isothermal, transcription-associated amplification reaction;

(d) combining the first amplification product with a second phase amplification reaction mixture comprising a second promoter primer comprising the nucleobase sequence of SEQ ID NO: 47 and a probe oligomer comprising the nucleobase sequence of SEQ ID NO: 57; and performing, in a second phase, substantially isothermal, transcription-associated amplification reaction in the second phase amplification reaction mixture, an exponential amplification of the first amplification product, thereby synthesizing a second amplification product;

(f) detecting, with the probe oligomer at regular time intervals, synthesis of the second amplification product in the second phase amplification reaction mixture; and (g) quantifying the target nucleic acid sequence in the sample using results from step (f).

64. The method of embodiment 63 wherein the at least one TCO comprises a first TCO comprising the nucleobase sequence of SEQ ID NO: 43 and a second TCO comprising the nucleobase sequence of SEQ ID NO: 45.

65. The method of embodiment 63 or 64, wherein the first and second promoter primers each comprise a 5' promoter sequence for an RNA polymerase.

66. The method of embodiment 65, wherein the RNA polymerase is T7 RNA polymerase.

67. The method of any one of embodiments 63-67, wherein the solid support comprises an immobilized capture probe.

68. The method of embodiment 67, wherein the solid support comprises magnetically attractable particles.

69. The method of any one of embodiments 63-68, wherein the each of the first and second phase isothermal transcription-associated amplification reactions comprises an RNA polymerase and a reverse transcriptase, and wherein the reverse transcriptase comprises an endogenous RNaseH activity.

70. The method of any one of embodiments 63-69, wherein the first amplification product of step (c) is a cDNA molecule with the same polarity as the target nucleic acid sequence in the sample, and the second amplification product of step (d) is an RNA molecule.

71. The method of any one of embodiments 63-70, wherein the probe oligomer in step (d) is a conformation-sensitive probe that produces a detectable signal when hybridized to the second amplification product.

72. The method of any one of embodiments 63-71, wherein the probe oligomer in step (d) is a fluorescently labeled sequence-specific hybridization probe.

73. The method of any one of embodiments 64-72, wherein the first TCO comprises the nucleobase sequence of SEQ ID NO: 42, the second TCO comprises the nucleobase sequence of SEQ ID NO: 44, the first and second promoter primers each comprise the nucleobase sequence of SEQ ID NO: 46, and the probe oligomer comprises the nucleobase sequence of SEQ ID NO: 56.

74. The method of any one of embodiments 63-73, wherein the first phase amplification reaction mixture and/or second phase amplification reaction mixture further comprises a helper oligomer and/or a displacer oligomer.

75. The method of embodiment 74, wherein the helper oligomer is 19-31 nucleobases in length and comprises the nucleobase sequence of SEQ ID NO: 14 and the displacer oligomer is 21-27 nucleobases in length and comprises the nucleobase sequence if SEQ ID NO: 41.

76. The method of embodiment 74 or 75, wherein the helper oligomer, the displacer oligomer or both the helper oligomer and the displacer oligomer are blocked.

EXAMPLES

Example 1. CMV Amplification

Various concentration combinations of salts and oligomers for CMV were evaluated to determine the suitable conditions amplification. PPR (primer probe containing recon buffer) mixes were made by mixing primers, probes, KCl, and $MgCl_2$ mixes. The following mixes were made to be used for the CMV DOE:

TABLE 1-1

| Primer Mixes | | | |
|---|---|---|---|
| | LOW | MID | HIGH |
| Concentration of Primer (μM) O4 | 0.4 | 0.7 | 1 |
| 1.25 × concentration of primer (LAM) | 0.5 | 0.875 | 125 |
| # of conditions (PPR) with that primer on | 4 | 5 | 4 |
| # of reps needed 48 | 48 | 84 | 48 |
| Overage Factor | 1.1 | 1.1 | 1.1 |
| reps needed * overage | 52.8 | 92 | 52.8 |
| Total reps needed (Rounded Number of Reps) | 53 | 93 | 53 |
| Volume of PPR per test (μL) | 45.83 | 45.83 | 45.83 |
| Volume of Component (μL) | 10 | 10 | 10 |
| Total Volume Needed (μL) | 530 | 930 | 530 |

TABLE 1-2

| Oligomers | | | | | | |
|---|---|---|---|---|---|---|
| Primers mix | SEQ ID NO. | Stock conc. (μM) | Volume (μL) | Volume (μL) | Volume (μL) | Total Needed (μL) |
| primer | 11 | 100.0 | 12.14 | 37.29 | 30.36 | 79.80 |
| primer | 23 | 100.0 | 12.14 | 37.29 | 30.36 | 79.80 |
| primer | 83 | 187.5 | 6.48 | 19.89 | 16.19 | 42.56 |
| primer | 84 | 194.2 | 6.25 | 19.21 | 15.64 | 41.10 |
| Water | | | 492.98 | 816.32 | 437.45 | 1746.74 |
| Total vol needed (μL) | | | 530.00 | 930.00 | 530.00 | |

TABLE 1-3

| Probe mixes | | | |
|---|---|---|---|
| | LOW | MID | HIGH |
| Concentration of Probe (μM) | 0.2 | 0.5 | 0.8 |
| 1.25 × concentration of probe (μM) | 0.25 | 0.625 | 1 |
| # of conditions (PPR) with that probe conc. | 4 | 5 | 4 |
| Number of reps needed | 48 | 84 | 48 |
| Overage Factor | 1.1 | 1.1 | 1.1 |
| # of Reps needed *overage | 52.8 | 92.40 | 52.8 |
| Total reps needed (Rounded Number of Reps) | 53 | 93.00 | 53 |
| Volume of PPR per test (μL) | 45.83 | 45.83 | 45.83 |
| Volume of Component (μL) | 5 | 5 | 5 |
| Total Volume Needed (μL) | 265 | 465 | 265 |

TABLE 1-4

| | SEQ ID NO. | Stock conc. (μM) | Volume (μL) | Volume (μL) | Volume (μL) | Total Needed (μL) |
|---|---|---|---|---|---|---|
| probe | 53 | 146.6 | 4.14 | 18.17 | 16.57 | 38.88 |
| probe | 85 | 147.4 | 4.12 | 18.07 | 16.48 | 38.67 |
| Water | | 256.74 | 428.76 | 231.95 | 917.45 | |
| Total Vol needed (μL) | | 265 | 465 | 265 | | |

TABLE 1-5

| $MgCl_2$ mixes | | | |
|---|---|---|---|
| | LOW | MID | HIGH |
| $MgCl_2$ conc, final in PCR (mM) | 2 | 4 | 6 |
| Concentration of MgCl2 (mM) in PCR from PPR | 1.92 | 3.92 | 5.92 |
| 1.25 × concentration of MgCl2 (mM) | 2.4 | 4.9 | 7.4 |
| # of conditions (PPR) with that primer conc | 4 | 5 | 4 |
| # of reps needed | 48 | 84 | 48 |
| Overage Factor | 1.1 | 1.1 | 1.1 |
| # of reps needed * overage | 52.8 | 92.4 | 52.8 |
| Total reps needed (Rounded Number of Reps) | 53 | 93 | 53 |
| Volume of PPR per test (μL) | 45.83 | 45.83 | 45.83 |
| Volume of Component (μL) | 2 | 2 | 2 |
| Total Volume Needed (μL) | 106 | 186 | 106 |

TABLE 1-6

| Components | Concentration (mM) | Volume (μL) | Volume (μL) | Volume (μL) |
|---|---|---|---|---|
| $MgCl_2$ mixes | 1000.00 | 5.8 | 20.9 | 18.0 |
| Water | | 100.2 | 165.1 | 88.0 |
| Total volume needed (μL) | 106 | 186 | 106 | |

TABLE 1-7

| KCl/Water mix | | | | | | |
|---|---|---|---|---|---|---|
| Component | [initial] | Units | [final] | Recon (1.25×) | 1× (μL) | 198 |
| KCI | 2000 | mM | 65 | 81.25 | 1.86 | 368.7 |
| Water | | | | | 26.97 | 5340.3 |
| Total Component Volume: | | | | | 28.83 | 5709.0 |
| Total PPR Volume per reaction | | | | | 45.83 | |

TABLE 1-8

| PPR final mixes: | | | | | | | | | | | | | | | | |
|---|---|---|---|---|---|---|---|---|---|---|---|---|---|---|---|---|
| Conditions/ | Mixes | Mixes | # reps per | Primer (μL) | | | Probe Mix (μL) | | | MgCl mix (μL) | | | KCl | Total μL in PPR | Vol per test PCR |
| PPR# | (Prl/Pro/Mg)* | (Prl/Pro/Mg) | PPR | H | M | L | H | M | L | H | M | L | Mix | tube | (μL) |
| PPR 01 | + + 0 | HHM | 12 | 120 | | | 60 | | | | 24 | | 346.0 | 550 | 45.83 |
| PPR 02 | + 0 − | HML | 12 | 120 | | | | 60 | | | | 24 | 346.0 | 550 | 45.83 |
| PPR 03 | + − 0 | HLM | 12 | 120 | | | | | 60 | | 24 | | 346.0 | 550 | 45.83 |
| PPR 04 | − + 0 | LHM | M | | | 120 | 60 | | | | 24 | | 346.0 | 550 | 45.83 |
| PPR 05 | + 0 + | HMH | 12 | 120 | | | | 60 | | 24 | | | 346.0 | 550 | 45.83 |
| PPR 06 | 0 − − | MLL | 12 | | 120 | | | | 60 | | | 24 | 346.0 | 550 | 45.83 |
| PPR 07 | − 0 − | LML | 12 | | | 120 | | 60 | | | | 24 | 346.0 | 550 | 45.83 |
| PPR 08 | − − 0 | LLM | 12 | | | 120 | | | 60 | | 24 | | 346.0 | 550 | 45.83 |
| PPR 09 | 0 + − | MHL | 12 | | 120 | | 60 | | | | | 24 | 346.0 | 550 | 45.83 |
| PPR 10 | 0 − + | MLH | 12 | | 120 | | | | 60 | 24 | | | 346.0 | 550 | 45.83 |
| PPR 11 | − 0 + | LMH | 12 | | | 120 | | 60 | | 24 | | | 346.0 | 550 | 45.83 |
| PPR 12 | 0 + + | MHH | 12 | | 120 | | 60 | | | 24 | | | 346.0 | 550 | 45.83 |
| PPR 13 | 0 0 0 | MMM | 36 | | 360 | | | 180 | | | 72 | | 1038.0 | 1650 | 45.83 |
| Total volumes needed (μL) | | | 180 | 480 | 840 | 480 | 240 | 420 | 240 | 96 | 168 | 96 | 5190 | 8250 | |

*Prl = Primer, Pro = probe, Mg = $MgCl_2$

PPR mixes 1-12 were vortexed, spun down, 250 μL of oil added to the top, and spun down again before loading onto the instrument. PPR mix 13 was also spun down, but with 400 μL of oil top instead of 250 μL.

A CMV Plasmid was diluted to 1000 cp/rxn to be tested with PPR mixes in Section 1. The CMV Plasmid was diluted to 1000 cp/rxn in STM by doing the following:

TABLE 1-9

| Concentration Needed (Calculation) | |
|---|---|
| start conc. (cp/uL) | $1.00 \times 10^4$ |
| testing amount (cp) per 5 μL rxn | 1000 |
| cp/μL in sample tube | 27.78 |
| start vol (μL) | 116.7 |
| μL of STM | 41883.3 |
| final vol (μL) | 42000.00 |

34 ml was aliquoted into 30 tubes. All 30 tubes were processed on a Panther Fusion system (Hologic, Inc., San Diego, CA) with 2 ext and 3 reps each extraction for each tube (n=12 for PPR 1-12 and n=36 for PPR 13). Data was analyzed on using a DevTool (4.9.8.0) having the following parameters:

TABLE 1-10

| Channel | CrossTalk Correction | Convergence Cycle | End Cycle Cutoff | Positivity/CT Threshold |
|---|---|---|---|---|
| FAM. | N/A | 10 | 75 | 1000 |
| HEX | N/A | N/A | N/A | N/A |
| ROX | N/A | N/A | N/A | N/A |
| RED647 | N/A | N/A | N/A | N/A |
| RED677 | N/A | 10 | 25 | 500 |

TABLE 1-11

| | SEQ ID NO. | Sequence 5' → 3' | Modifications | MW w/o modifications |
|---|---|---|---|---|
| CMV | | | | |
| primer | 11 | CAGATACACTATAGCCGCCG | None | 6070.95 |
| primer | 23 | CCATGGAGCTGGAGTGTCTAAAG | None | 7128.63 |
| probe | 53 | CGTGGACTCCGCCAGTAACACGTT | 5' Fluorescein, 8 mdCs, 3'BHQ1 | 7313.72 |
| IC | | | | |
| primer | 83 | ATGGTCAATTAGAGACAAAG | None | 6198.08 |
| primer | 84 | CGTTCACTATTGGTCTCTGC | None | 6049.88 |
| probe | 85 | CGGAATCACAAGTCAATCATCGCG CA | 5' Q705 and 3' BHQ2 | 7933.16 |

TABLE 1-12

| For RFU, Lack of Fit | | | | |
|---|---|---|---|---|
| Source | LF | Sum of Squares | Mean Square | F Ratio |
| Lack of Fit | 3 | 91858924.1 | 30619641 | 2.8092 |
| Pure Error | 167 | 1820287087 | 10899923 | Prob > F |
| Total Error | 170 | 1912146012 | | 0.0412* |
| | | | | Max RSq |
| | | | | 0.9075 |

TABLE 1-13

| For Ct, Lack of Fit | | | | |
|---|---|---|---|---|
| Source | LF | Sum of Squares | Mean Square | F Ratio |
| Lack of Fit | 3 | 0.428995 | 0.142998 | 0.6612 |
| Pure Error | 167 | 36.116560 | 0.216267 | Prob > F |
| Total Error | 170 | 36.545554 | | 0.5570 |
| | | | | Max RSq |
| | | | | 0.5984 |

TABLE 1-14

| For Baseline, Lack of Fit | | | | |
|---|---|---|---|---|
| Source | LF | Sum of Squares | Mean Square | F Ratio |
| Lack of Fit | 3 | 8800858 | 29336619 | 1.8490 |
| Pure Error | 167 | 264966454 | 1586625 | Prob > F |
| Total Error | 170 | 273767313 | | 0.1406 |
| | | | | Max RSq |
| | | | | 0.9440 |

Signal to noise remains highest with high salts and high oligomers. A decrease in oligomers only slightly affects signal to noise. In some embodiments, the salts were >4 mM.

Conclusion: Ct and Baseline show significance with Primer+Mg and Primer+Probe, RFU Primer+Mg and Probe+Mg. All show Lack of Fit greater than 0.0001, with RFU showing the lowest of 0.0412. The most desirable option is 1 μM primer, 0.8 μM probe, and 6 mM MgCl. However, lower MgCl also shows very nice results. It is probable that JPM estimates 6 mM as the optimal solely based on background, because lower salts increases RFU and also increases background. The lower the primer and probe, though, show a similar Ct but results in a 20% drop in RFU with each 0.2 μM difference. Data suggests that Ct is too similar across all conditions because it only accounts for 57% variability, while RFU and Baseline are 90% and 94%.

Example 2: CMV Plasmid Limit of Detection

CMV plasmid was evaluated in serum to determine the Limit of Detection (LoD). Sample lysis was performed using 360 μL sample combined with 450 μL target capture reagent and 126 μL target enhancer reagent. After incubation the mixture was washed with target capture wash reagent and eluted in 50 μL final volume. CMV PPR was made to determine LoD of Plasmid in serum.

TABLE 2-1

| PPR mix | | | | | | |
|---|---|---|---|---|---|---|
| | SEQ ID NO. | Units | Stock Conc | Final Conc | ×1.25 | μL |
| primer | 11 | μM | 100.00 | 1.00 | 1.25 | 26.1 |
| primer | 23 | μM | 100.00 | 1.00 | 1.25 | 26.1 |
| probe | 53 | μM | 146.30 | 0.80 | 1.00 | 14.3 |
| primer | 83 | μM | 187.50 | 0.60 | 0.75 | 8.4 |
| primer | 84 | μM | 194.20 | 0.60 | 0.75 | 8.1 |
| probe | 85 | μM | 147.40 | 0.40 | 0.50 | 7.1 |
| $MgCl_2$ | | mM | 1000.00 | 5.00 | 6.25 | 13.1 |
| KCl | | mM | 2000.00 | 65.00 | 81.25 | 84.9 |
| | | | | | Water: | 1902.0 |
| | | | | | Total: | 2090.0 |

Two tubes were prepared. One with 1200 μL of PPR mix in recon tube and 400 μL of oil added to the top. The other with 850 μL of PPR mix added to a recon tube and 350 μL of oil added to the top. All tubes were spun down again before loading onto the instrument. CMV plasmid was diluted to three concentrations in Serum and tested with the PPR mixes in Section 1. CMV plasmid was diluted to 100, 10, and 1 cp/rxn in pooled serum by doing the following:

TABLE 2-2

| CMV plasmid dilution, CMV Calibrator 6 in Plasma/Serum (1:1 with STM) | | | | |
|---|---|---|---|---|
| Stock conc (cp/μL) | final conc (cp/μL) | Stock vol (μL) | μL of water (μL) | final vol needed (μL) |
| 1.00E+04 | 1.00E+03 | 50 | 450 | 500 |

TABLE 2-3

| CMV plasmid dilution, Concentration needed. | | | | | | |
|---|---|---|---|---|---|---|
| start conc (cp/μL) | testing amount (cp) per 5 μL rxn | cp/μL in sample tube | Final cp/ml in lysed sample tube | start vol (μL) | μL of Serum | final vol (μL) |
| 1.00E+03 | 100 | 5.56 | 2777.78 | 37.8 | 6762.2 | 6800.00 |
| 5.56 | 10 | 0.56 | 277.78 | 600.0 | 5400.0 | 6000.00 |
| 0.56 | 1 | 0.06 | 27.78 | 520.0 | 4680.0 | 5200.00 |

Pooled serum samples consisted of serum 051-056 of 3 ml each. An STM with 1 mg/ml proteinase K was prepared by adding 400 μL 20 mg/mL stock ProK solution to 7600 μL STM.

1230 μL of each concentration of CMV plasmid was added to 2 tubes containing 1230 μL of the STM:ProK (Solution Transport Media: Proteinase K) mixture in 2.2. Remaining volume was not lysed and was stored at −70° C. if needed. Each tube was processed with 10 PCR reps (4 extractions with 3 PCR reps for 3 ext and 1 PCR rep for the 4th) at n=20 each concentration. A negative control was made consisting of 390ul of the STM:ProK mixture and 390 μL of the serum pool. One extraction was processed with three PCR reps per extraction. All samples were processed, and data was analyzed using a DevTool (4.9.8.0) having the following parameters:

TABLE 2-4

| DevTool 4.9.8.0 using the following parameters | | | | |
|---|---|---|---|---|
| Channel | CrossTalk Correction | Convergence Cycle | End Cycle Cutoff | Positivity/CT Threshold |
| FAM | N/A | 10 | 100 | 1000 |
| HEX | N/A | N/A | N/A | N/A |

TABLE 2-4-continued

| DevTool 4.9.8.0 using the following parameters | | | | |
|---|---|---|---|---|
| Channel | CrossTalk Correction | Convergence Cycle | End Cycle Cutoff | Positivity/CT Threshold |
| ROX | N/A | N/A | N/A | N/A |
| RED647 | N/A | N/A | N/A | N/A |
| RED677 | N/A | 10 | 25 | 500 |

Conclusion: LoD of CMV plasmid in pooled serum is 10 cp/rxn, or 277.78 cp/ml in lysed sample tube at 95%. Plasmid has not been tested in serum for the TMA CMV team.

TABLE 2-5

| Oligo info - description | | | | |
|---|---|---|---|---|
| Oligo name | SEQ ID NO | Sequence 5' → 3' | Modifications | MW without Modifications |
| CMV | | | | |
| primer | 11 | CAGATACACTATAGCCGCCG | None | 6070.95 |
| primer | 23 | CCATGGAGCTGGAGTGTCTAAAG | None | 7128.63 |
| probe | 53 | CGTGGACTCCGCCAGTAACACGTT | 5' Fluorescein, 8 mdCs, 3' BHQ1 | 7313.72 |
| IC | | | | |
| primer | 83 | ATGGTCAATTAGAGACAAAG | None | 6198.08 |
| primer | 84 | CGTTCACTATTGGTCTCTGC | None | 6049.88 |
| probe | 85 | CGGAATCACAAGTCAATCATCGCGCA | 5' Q705 and 3' BHQ2 | 7933.16 |

TABLE 2-6

| Results | | | | | | | | | | | | |
|---|---|---|---|---|---|---|---|---|---|---|---|---|
| Conc. (cp/rxn) | Concentration of Initial Specimen (cp/ml) | Channel | Reactivity | Reactivity (%) | Average of Ct | StdDev of Ct | Average of RFU | StdDev of RFU | Avg T-Slope | Avg Background | Total RFU | Signal to Noise |
| CMV | | | | | | | | | | | | |
| 100 | 5555.56 | FAM | 20/20 | 100% | 33.71 | 0.37 | 32984.79 | 4518.03 | 668.86 | 14125.31 | 47110.09 | 3.34 |
| 10 | 555.56 | | 19/20 | 95% | 37.32 | 0.94 | 18359.33 | 4754.07 | 667.41 | 14745.75 | 33117.57 | 2.25 |
| 1 | 55.56 | | 5/20 | 25% | 39.31 | 0.47 | 10716.30 | 2085.13 | 711.69 | 14185.52 | 24927.23 | 1.76 |
| 100 | 5555.56 | RED677 | 20/20 | 100% | 28.17 | 0.15 | 6954.52 | 561.58 | 355.54 | 2065.13 | 9019.64 | 4.37 |
| 10 | 555.56 | | 20/20 | 100% | 28.14 | 0.19 | 7267.89 | 963.41 | 332.23 | 2204.70 | 9472.59 | 4.30 |
| 1 | 55.56 | | 20/20 | 100% | 23.11 | 0.15 | 7053.87 | 633.05 | 345.30 | 2031.31 | 9035.18 | 4.47 |
| Negative Control | | | | | | | | | | | | |
| N/A | N/A | FAM | 0/3 | 0% | N/A | N/A | N/A | N/A | N/A | 13194.121 | N/A | N/A |
| N/A | N/A | RED677 | 3/3 | 100% | 28.11 | 0.11 | 6867.43 | 589.21 | 373.85 | 1920.53 | 8787.96 | 4.58 |

Note:
Specimen refers to plasmid, unlysed

Example 3: CMV Preliminary Viral Limit of Detection in Serum and Plasma

Limits of Detection were determined for CMV virus (TCID50/ml) in serum and plasma in 1 log increments, as described in example 2 and a 1:0.2 STM ratio CMV PPR was made to determine LoD of virus in serum and plasma. The following PPR mix was:

TABLE 3-1

| PPR mix | | | | | | |
|---|---|---|---|---|---|---|
| Name | SEQ ID NO. | Units | Stock Conc | Final Conc | ×1.25 | µL |
| primer | 11 | µM | 199.10 | 1.00 | 1.25 | 13.6 |
| primer | 23 | µM | 186.10 | 1.00 | 1.25 | 14.5 |
| probe | 53 | µM | 146.30 | 0.30 | 1.00 | 14.8 |
| primer | 83 | µM | 187.50 | 0.60 | 0.75 | 8.6 |
| primer | 84 | µM | 214.90 | 0.60 | 0.75 | 7.5 |
| probe | 85 | µM | 147.40 | 0.40 | 0.50 | 7.3 |
| $MgCl_2$ | | mM | 1000.00 | 5.00 | 6.25 | 13.5 |
| KCl | | mM | 2000.00 | 65.00 | 31.25 | 87.8 |
| | | | | | Water: | 1992.4 |
| | | | | | Total: | 2160.0 |

Two tubes were prepared. One with 1100 µL of PPR mix in recon tube and 400 µL of oil added to the top. The other with 1000 µL of PPR mix added to a recon tube and 400 µL of oil added to the top. All tubes were spun down again, before loading onto the instrument. CMV virus was diluted to five concentrations in serum and plasma and tested with the PPR mix in Section 1. CMV was diluted to 10000, 1000, 100, 10, and 1 TCID50/ml in pooled serum and pooled plasma by doing the following:

TABLE 3-2

| CMV dilution | | | | |
|---|---|---|---|---|
| Stock conc (TCID50/ml) | Final conc (TCID50/ml | Stock vol (µL) | µL of water (µL) | final vol needed (µL) |
| 2.19E+06 | 2.19E+05 | 18 | 162 | 180 |

TABLE 3-3

| CMV in Plasma and Serum Concentration Needed (Calculation) | | | | | | |
|---|---|---|---|---|---|---|
| start cone (TCID50/ml) | testing amount (TCID50/ml) per 5 µL rxn | TCID50/ml in "specimen" tube | Final TCID50/ml in lysed sample tube | start vol (µL) | µL of Serum or Plasma | final vol (µL) |
| 2.19E+05 | 233 | 10000.00 | 8130.08 | 82.2 | 1717.8 | 1800.00 |
| 1.00E+04 | 29 | 1000.00 | 813.01 | 1E0.0 | 1440.0 | 1800.00 |
| 1.00E+03 | 3 | 100.00 | 81.30 | 140.0 | 1250.0 | 1400.00 |
| 1.00E+02 | 0.29 | 10.00 | 8.13 | 125.0 | 1125.0 | 1250.00 |
| 1.00E+01 | 0.03 | 1.00 | 0.81 | 110.0 | 990.0 | 1100.00 |

Pooled serum samples consisted of serum of 3 ml each and pooled plasma consisted of plasma of 3 ml each. Concentrations were based on BioFire LoD of 100 TCID50/ml. An STM with 2.6 mg/ml proteinase K was prepared by doing the following:

TABLE 3-4

| stock ProK conc (mg/ml) | final cone (mg/ml) | start vol (µL) | vol STM (µL) | final vol (µL) |
|---|---|---|---|---|
| 20 | 26 | 416 | 2784 | 3200 |

To ensure ProK was not sitting in the STM for an extended amount of time, this mixture was made right before the samples were ready to be lysed. 800 µL of each concentration of CMV plasmid in both serum and plasma was added to 1 tube containing 185 µL of the STM:ProK mixture. Each tube was processed with 2 extractions and 3 PCR. A negative control was made consisting of 115 µL of the STM:ProK mixture and 500 µL of the serum pool and the plasma pool separately. One extraction was processed with three PCR reps per extraction. All samples were processed on a Panther Fusion system (Hologic, Inc. San Diego). Data was analyzed using a DevTool (4.9.8.0) having the following parameters:

TABLE 3-5

| Channel | CrossTalk Correction | Convergence Cycle | End Cycle Cutoff | Positivity/CT Threshold |
|---|---|---|---|---|
| FAM | N/A | 10 | 150 | 1000 |
| HEX | N/A | N/A | N/A | N/A |
| ROX | N/A | N/A | N/A | N/A |
| RED647 | N/A | N/A | N/A | N/A |
| RED677 | N/A | 10 | 25 | 500 |

TABLE 3-6

| Oligo info - description | | | | |
|---|---|---|---|---|
| Target/ Oligo name | SEQ ID NO. | Sequence 5' → 3' | Modifications | MW without Modifications |
| CMV | | | | |
| primer | 11 | CAGATACACTATAGCCGCCG | None | 6070.95 |
| primer | 23 | CCATGGAGCGGAGTGTCTAAAG | None | 7128.63 |
| probe | 53 | CGTGGACTCCGCCAGTAACACGT | 5' Fluorescein, 8 mdCs, 3'BHQ1 | 7313.72 |
| IC | | | | |
| primer | 83 | ATGGTCAATTAGAGACAAAG | None | 6198.08 |
| primer | 84 | CGTTCACTATTGGTCTCTGC | None | 6049.88 |
| probe | 85 | CGGAATCACAAGTCAATCATCGCGCA | 5' Q705 and 3' BHQ2 | 7933.16 |

TABLE 3-7

| Results—description | | | | | | | | | | | |
|---|---|---|---|---|---|---|---|---|---|---|---|
| Matrix | Concentration of Initial "Specimen" (TCID50/ml) | Concentration of Initial "Specimen" (cp/ml) per BioFire | Channel | Reactivity | Reactivity (%) | Average of Ct | StdDev of Ct | Average of RFU | StdDev of RFU | Avg T-Slope | Avg Background |
| Plasma | 10000 | 430000 | FAM | 6/6 | 100% | 23.99 | 0.29 | 48528.62 | 1168.36 | 650.22 | 14484.28 |
| | 1000 | 43000 | | 6/6 | 100% | 27.59 | 0.62 | 48201.30 | 1025.86 | 667.27 | 14931.30 |
| | 100 | 4300 | | 6/6 | 100% | 31.26 | 0.88 | 42836.78 | 4879.56 | 651.46 | 14738.72 |
| | 10 | 430 | | 6/6 | 100% | 34.99 | 0.15 | 31976.03 | 3793.56 | 673.69 | 15498.45 |
| | 1 | 43 | | 6/6 | 100% | 39.02 | 0.75 | 12065.00 | 3157.83 | 583.79 | 13998.46 |
| Serum | 10000 | 430000 | | 6/6 | 100% | 20.17 | 0.57 | 49693.75 | 4001.43 | 361.79 | 13803.65 |
| | 1000 | 43000 | | 6/6 | 100% | 25.53 | 0.27 | 49023.22 | 1380.64 | 629.81 | 13793.67 |
| | 100 | 4300 | | 6/6 | 100% | 30.21 | 0.49 | 42028.75 | 5604.09 | 621.44 | 12661.11 |
| | 10 | 430 | | 6/6 | 100% | 31.86 | 1.93 | 42066.58 | 7077.17 | 678.69 | 14375.13 |
| | 1 | 43 | | 6/6 | 100% | 38.04 | 0.62 | 16400.45 | 4211.80 | 590.59 | 15234.27 |
| Plasma | 10000 | 430000 | RED677 | 6/6 | 100% | 29.02 | 0.26 | 6964.98 | 1017.48 | 306.33 | 2182.79 |
| | 1000 | 43000 | | 6/6 | 100% | 28.87 | 0.25 | 7127.95 | 806.13 | 320.52 | 2212.48 |
| | 100 | 4300 | | 6/6 | 100% | 28.84 | 0.32 | 7168.95 | 1125.91 | 297.75 | 2198.40 |
| | 10 | 430 | | 6/6 | 100% | 28.75 | 0.16 | 7645.00 | 567.46 | 266.59 | 2312.67 |
| | 1 | 43 | | 6/6 | 100% | 28.89 | 0.28 | 6982.38 | 975.37 | 289.23 | 2022.86 |
| Serum | 10000 | 430000 | | 6/6 | 100% | 28.50 | 0.28 | 6408.67 | 872.70 | 291.26 | 1871.66 |
| | 1000 | 43000 | | 6/6 | 100% | 28.57 | 0.13 | 6759.84 | 670.75 | 284.04 | 1948.20 |
| | 100 | 4300 | | 6/6 | 100% | 28.56 | 0.21 | 6524.65 | 582.50 | 292.73 | 1924.81 |
| | 10 | 430 | | 6/6 | 100% | 26.54 | 0.09 | 6981.45 | 382.35 | 293.78 | 2014.34 |
| | 1 | 43 | | 6/6 | 100% | 28.53 | 0.13 | 7029.07 | 417.28 | 295.25 | 2161.73 |

1E1 (i.e., $1\times10^1$ or 10) TCID50/ml for serum resulted in almost 1 log difference from extraction to extraction. Only 1 tube was processed, so all extractions came from the same tube. This is a unique occurrence. Plasma, at the same concentration, resulted in expected results. All other samples also resulted in similar results between ext/PCR rep.

Conclusion: Preliminary LoD shows 100% detection around 10 TCID50/ml in both serum and plasma. It appears plasma may have had some inhibition issues, or resulted in degradation of the virus itself, because there is a delay in Ct. Also, results for serum at 1E1 TCID50/ml showed a high standard deviation. Further analysis, with half log increments, will help determine the true LoD of CMV virus in serum and plasma.

Example 4. CMV Preliminary Viral Limit of Detection in Serum and Plasma

Limits of Detection were determined for CMV virus (TCID50/ml) in serum and plasma in half log increments, as described in example 2 and a 1:0.2 STM ratio. CMV PPR was made to determine LoD of virus in serum and plasma. The Following PPR mix was made:

TABLE 4-1

| PPR Mix | | | | | | |
|---|---|---|---|---|---|---|
| Name | SEQ ID NO. | Units | Stock Conc | Final Conc | ×1.25 | μL |
| primer | 11 | μM | 199.10 | 1.00 | 1.25 | 33.3 |
| primer | 23 | μM | 186.10 | 1.00 | 1.25 | 35.6 |
| probe | 53 | μM | 146.30 | 0.80 | 1.00 | 36.2 |
| primer | 83 | μM | 187.50 | 0.60 | 0.75 | 21.2 |
| primer | 84 | μM | 214.90 | 0.60 | 0.75 | 18.5 |
| probe | 85 | μM | 147.40 | 0.40 | 0.50 | 18.0 |
| MgCl2 | | mM | 1000.00 | 5.00 | 6.25 | 33.1 |
| KCl | | mM | 2000.00 | 65.00 | 81.5 | 215.3 |
| | | | | | Water: | 4888.8 |
| | | | | | Total: | 5300.0 |

Five tubes were prepared. Four with 1200 μL of PPR mix in recon tube and 400 μL of oil added to the top. The other with 400 μL of PPR mix added to a recon tube and 250 μL of oil added to the top. All tubes were spun down again, before loading onto the instrument. CMV virus was diluted to four concentrations in serum and plasma and tested with the PPR mix in Section 1. CMV was diluted to 31.6, 10, 3.16, and 1 TCID20/ml in pooled serum and pooled plasma by doing the following:

TABLE 4-2

| CMV dilution | | | | |
|---|---|---|---|---|
| Stock conc (TCID50/ml) | final conc (TCID50/ml) | Stock vol (μL) | Water (μL) | final vol needed (μL) |
| 2.19E+06 | 2.19E+04 | 5 | 495 | 500 |
| 2.19E+04 | 2.19E+03 | 15 | 135 | 150 |

TABLE 4-3

| CMV in Plasma and Serum, Concentration Needed (Calculation) | | | | | | | |
|---|---|---|---|---|---|---|---|
| start conc (TCID50/ml) | testing amount (TCID50/ml) per 5 μL rxn | TCID50/ml in "specimen" tube | cp/ml in "specimen" tube per BioFire | Final TCID50/ml in lysed sample tube | start vol (μL) | μL of Serum or Plasma | final vol (μL) |
| 2.19E+03 | 1 | 31.62 | 1359.78 | 25.71 | 65.0 | 4435.0 | 4500.00 |
| 31.62 | 0.29 | 10.00 | 430.00 | 8.13 | 1359.9 | 2940.1 | 4300.00 |
| 10.00 | 0.09 | 3.16 | 135.98 | 2.57 | 1264.9 | 2735.1 | 4000.00 |
| 3.16 | 0.03 | 1.00 | 43.00 | 0.81 | 949.4 | 2050.6 | 3000.00 |

Pooled serum samples consisted of serum of 3 ml each and pooled plasma consisted of plasma of 3 ml each. An STM with 2.6 mg/ml proteinase K was prepared by doing the following:

TABLE 4-4

| stock ProK conc (mg/ml) | final conc (mg/ml) | start vol (μL) | vol STM (μL) | final vol (μL) |
|---|---|---|---|---|
| 20 | 26 | 754 | 5046 | 5800 |

To ensure ProK was not sitting in the STM for an extended amount of time, this mixture was made right before the samples were ready to be lysed. 1400 μL of each concentration of CMV plasmid in both serum and plasma was added to 2 tube containing 325 μL of the STM:ProK mixture. Each tube was processed with 3 extractions and 3 PCR reps each, along with 1 extraction with 1 PCR rep. Since two tubes were processed, n=20 per concentration. A negative control was made consisting of 115 μL of the STM:ProK mixture and 500 μL of the serum pool and the plasma pool separately. One extraction was processed with three PCR reps per extraction. All samples were processed on a Panther Fusion system. Data was analyzed using a DevTool having the following parameters:

TABLE 4-5

| Channel | CrossTalk Correction | Convergence Cycle | End Cycle Cutoff | Positivity/ CT Threshold |
|---|---|---|---|---|
| FAM | N/A | 10 | 150 | 1000 |
| HEX | N/A | N/A | N/A | N/A |
| ROX | N/A | N/A | N/A | N/A |
| RED647 | N/A | N/A | N/A | N/A |
| RED677 | N/A | 10 | 25 | 500 |

TABLE 4-6

| Oligo info - description | | | | |
|---|---|---|---|---|
| Oligo | SEQ ID NO. | Sequence 5' → 3' | Modifications | MW without Modifications |
| CMV Target | | | | |
| primer | 11 | CAGATACACTATAGCCGCCG | None | 6070.95 |
| primer | 23 | CCATGGAGCTGGAGTGTCTAAAG | None | 7128.63 |
| probe | 53 | CGTGGACTCCGCCAGTAACACGTT | 5' Fluorescein, 8 mdCs, 3'BHQ1 | 7313.72 |

TABLE 4-6-continued

| Oligo info - description | | | | |
|---|---|---|---|---|
| Oligo | SEQ ID NO. | Sequence 5' → 3' | Modifications | MW without Modifications |
| IC Target | | | | |
| primer | 83 | ATGGTCAATTAGAGACAAAG | None | 6198.08 |
| primer | 84 | CGTTCACTATTGGTCTCTGC | None | 6049.88 |
| probe | 85 | CGGAATCACAAGTCAATCATCGCGCA | 5' Q705 and 3 BHQ2 | 7933.16 |

TABLE 4-7

| Concentration of Initial 'Specimen' (TCID50/ml) | Concentration of Initial 'Specimen' (cp/ml) per BioFire | Reactivity | Reactivity (%) | Average of Ct | StdDev of Ct | Average of RFD | StdDev of RFU | Avg T-Slope | Avg Background | Total RFU | Signal to Noise |
|---|---|---|---|---|---|---|---|---|---|---|---|
| Results—description | | | | | | | | | | | |
| Channel: FAM Plasma | | | | | | | | | | | |
| 31.62 | 1359.78 | 20/20 | 100% | 32.93 | 2.23 | 41265.37 | 5750.45 | 682.73 | 14135.56 | 55400.93 | 3.92 |
| 10.00 | 430.00 | 20/20 | 100% | 35.12 | 0.67 | 32543.74 | 4934.44 | 677.56 | 14378.94 | 46922.68 | 3.26 |
| 3.16 | 135.98 | 19/20 | 95% | 36.13 | 1.86 | 29313.06 | 9502.67 | 652.34 | 13949.19 | 41296.59 | 3.00 |
| 1.00 | 43.00 | 9/20 | 45% | 19.03 | 1.43 | 17076.74 | 6735.90 | 789.44 | 14207.75 | 21892.28 | 1.54 |
| Serum | | | | | | | | | | | |
| 31.62 | 1359.73 | 20/20 | 100% | 31.42 | 1.39 | 43348.57 | 4814.74 | 655.85 | 13931.20 | 57779.77 | 4.15 |
| 10.00 | 430.00 | 20/20 | 100% | 33.86 | 0.35 | 33273.43 | 3509.50 | 699.98 | 14538.07 | 52816.55 | 3.63 |
| 3.16 | 135.98 | 20/20 | 100% | 33.16 | 0.88 | 32405.31 | 5712.45 | 728.37 | 14247.04 | 46652.85 | 3.27 |
| 1.00 | 43.00 | 19/20 | 95% | 37.41 | 0.34 | 21216.18 | 3897.12 | 703.76 | 14551.95 | 34707.32 | 2.39 |
| Channel: RED677 Plasma | | | | | | | | | | | |
| 31.62 | 1359.73 | 20/20 | 100% | 28.92 | 0.25 | 7423.01 | 892.16 | 311.62 | 2331.53 | 9754.54 | 4.18 |
| 10.00 | 430.00 | 20/20 | 100% | 28.94 | 0.19 | 7898.31 | 769.68 | 285.96 | 2372.15 | 10270.46 | 4.33 |
| 3.16 | 135.98 | 20/20 | 100% | 29.05 | 0.16 | 7228.00 | 622.45 | 331.88 | 2205.65 | 9433.65 | 4.28 |
| 1.00 | 43.00 | 20/20 | 100% | 29.03 | 0.24 | 7553.91 | 994.95 | 314.33 | 2407.74 | 9966.65 | 4.14 |
| Serum | | | | | | | | | | | |
| 31.62 | 1359.73 | 20/20 | 100% | 28.42 | 0.17 | 8009.04 | 614.00 | 317.32 | 2523.46 | 10532.50 | 4.17 |
| 10.00 | 430.00 | 20/20 | 100% | 28.36 | 0.18 | 8381.46 | 1010.55 | 326.43 | 2751.45 | 11132.91 | 4.05 |
| 3.16 | 135.98 | 20/20 | 100% | 28.42 | 0.22 | 8642.33 | 894.40 | 327.19 | 2649.05 | 11291.37 | 4.26 |
| 1.00 | 43.00 | 20/20 | 100% | 23.37 | 0.14 | 8701.33 | 680.63 | 324.49 | 2777.29 | 11478.62 | 4.13 |

TABLE 4-8

| Concentration | Matrix | Well | Fluorophor | RFU Range | Ct_ NonNorm |
|---|---|---|---|---|---|
| CMV 1E1.5 | Plasma | TC-01-02 | FAM | 37317.37 | 34.16564 |
| CMV 1E1.5 | Plasma | TC-01-03 | FAM | 36365.78 | 35.20335 |
| CMV 1E1.5 | Plasma | TC-01-04 | FAM | 38495.92 | 34.72311 |
| CMV 1E1.5 | Plasma | TC-01-05 | FAM | 41086.35 | 34.29968 |
| CMV 1E15 | Plasma | TC-02-01 | FAM | 44371.27 | 33.81882 |
| CMV 1E1.5 | Plasma | TC-02-02 | FAM | 43054.29 | 33.93569 |
| CMV 1E1.5 | Plasma | TC-02-03 | FAM | 29808.49 | 35.27509 |
| CMV 1E1.5 | Plasma | TC-02-04 | FAM | 34872.88 | 34.92654 |
| CMV 1E1.5 | Plasma | TC-02-05 | FAM | 40565.99 | 34.24335 |
| CMV 1E1.5 | Plasma | TC-03-01 | FAM | 30032.57 | 35.79996 |
| CMV 1E1.5 | Plasma | TC-03-02 | FAM | 48443.3 | 29.02094 |
| CMV 1E1.5 | Plasma | TC-03-03 | FAM | 47580.82 | 29.29515 |
| CMV 1E1.5 | Plasma | TC-03-04 | FAM | 48437.76 | 29.0373 |
| CMV 1E1.5 | Plasma | TC-03-05 | FAM | 49014.11 | 30.4159 |
| CMV 1E1.5 | Plasma | TC-04-01 | FAM | 43398.7 | 30.98336 |
| CMV 1E1.5 | Plasma | TC-04-02 | FAM | 45347.95 | 30.28006 |
| CMV 1E1.5 | Plasma | TC-04-03 | FAM | 38813.75 | 33.19613 |
| CMV 1E1.5 | Plasma | TC-04-04 | FAM | 40581.24 | 33.25715 |

TABLE 4-8-continued

| Concentration | Matrix | Well | Fluorophor | RFU Range | Ct_ NonNorm |
|---|---|---|---|---|---|
| CMV 1E1.5 | Plasma | TC-04-05 | FAM | 41150.42 | 33.20494 |
| CMV 1E1.5 | Plasma | TC-05-01 | FAM | 43573.37 | 33.45069 |

Out of 20 PCR reps, 6 were very early in comparison to the average. All 6 came from the same tube (ext 1&2).

Conclusion: LoD of CMV in plasma and serum is somewhat variable. Plasma may have inhibitors that prevent 100% of CMV detection because there is a difference in Ct between the two matrices. Plasma has an LoD of 3.16 TCID50/ml, or 135.9 cp/ml per BioFire. Serum shows an LoD of 1 TCID50/ml, or 43 cp/ml per BioFire.

Example 5. Analyte Specific Reagent CMV Reactivity and Analysis of ZeptoMetrix CMV Control. CMV reactivity with 4 strains of CMV were evaluated using the current CMV PCR oligo set. All CMV isolates were tested at 10× LoD of original strain. Zeptometrix (Franklin, MA) CMV control was analyzed to determine assay sensitivity in cp/ml from whole virus, as well as help determine range of same strain in TCID50/ml. The following CMV PPR was prepared on:

TABLE 5-1

| PPR Mix | | | | | | |
|---|---|---|---|---|---|---|
| Name | Oligo ID | Units | Stock Conc | Final Conc | ×1.25 | μL |
| primer | 12 | μM | 226.00 | 1.00 | 1.25 | 10.8 |
| primer | 26 | μM | 212.10 | 1.00 | 1.25 | 11.6 |
| probe | 53 | μM | 165.40 | 0.80 | 1.00 | 11.9 |
| primer | 83 | μM | 193.09 | 0.60 | 0.75 | 7.6 |
| primer | 84 | μM | 266.80 | 0.60 | 0.75 | 5.5 |
| probe | 85 | μM | 94.20 | 0.40 | 0.50 | 10.4 |
| MgCl2 | | mM | 1000.00 | 5.00 | 6.25 | 12.3 |
| KCl | | mM | 2000.00 | 65.00 | 81.25 | 79.6 |
| | | | | | Water: | 1810.4 |
| | | | | | Total: | 1960.0 |

One recon tube was prepared with 1200 μL of PPR mix and 400 μL of oil and another with 700 μL of PPR mix and 300 μL of oil on top. All tubes were spun down before loading onto a Panther Fusion system. CMV Viral isolates were diluted to 1E1.5 TCID50/ml in plasma and processed on the Panther Fusion system.

TABLE 5-2

| CMV viral stocks used for this study | | | | |
|---|---|---|---|---|
| Specimen Description | ATCC# | GP# | Lot | Stock Conc. |
| CMV | VR-1590 | GP2134 | SD-RFS-000175 | 2.3E+4 TCID50/ml |
| CMV | VR-1788 | GP2137 | SD-RFS-000175 | 1.6E+2 TCID50/ml |
| CMV | VR-2356 | GP2138 | SD-RFS-000175 | 2.3E+6 TCID50/ml |
| CMV | VR-977 | GP2135 | SD-RFS-000175 | 2.5E+5 TCID50/ml |
| NATtrol CMV | N/A | NATCMV-0005 | 318997 | 100000 cp/ml |

CMV viral stocks were diluted to 1E1.5 TCID50/ml (10×LoD for strain AD-169) by doing the following (in plasma):

TABLE 5-3A

| Strain #1, Stock concentration (TCID50/ml) = 2.30E+04 | | | | | |
|---|---|---|---|---|---|
| Name | GP# | LN | ATCC | Strain | |
| CMV | GP2134 | SD-RFS-000175 | VR-1590 | Merlin | |
| start conc (TCID50/ml) | TCID50/ ml in sample tube | TCID50/ml after PBS dilution | start vol (μL) | μL of Plasma | final vol (μL) |
| 2.30E+04 | 1000.00 | 833 | 6.5 | 143.5 | 150.00 |
| 1.00E+03 | 31.60 | 26 | 34.8 | 1065.2 | 1100.00 |

TABLE 5-3B

| Strain #2, Stock concentration (TCID50/ml) = 1.60E+02 | | | | | |
|---|---|---|---|---|---|
| Name | GP# | LN | ATCC | Strain | |
| CMV | GP2137 | SD-RFS-000175 | VR-1788 | ATCC-2011-8 | |
| start conc (TCID50/ml) | TCID50/ ml in sample tube | TCID50/ml after PBS dilution | start vol (μL) | μL of Plasma | final vol (μL) |
| 1.60E+2 | 31.60 | 26 | 217.3 | 882.8 | 1100.00 |

TABLE 5-3C

| Strain #3, Stock concentration (TCID50/ml) = 2.30E+06 | | | | | |
|---|---|---|---|---|---|
| Name | GP# | LN | ATCC | Strain | |
| CMV | GP2138 | SD-RFS-000175 | VR-2356 | RC256 | |
| start conc (TCID50/ml) | TCID50/ ml in sample tube | TCID50/ml after PBS dilution | start vol (μL) | μL of Plasma | final vol (μL) |
| 2.30E+06 | 100000.00 | 83333 | 6.5 | 143.5 | 150.00 |
| 1.00E+05 | 1000.00 | 833 | 5.0 | 495.0 | 500.00 |
| 1.00E+03 | 31.60 | 26 | 34.8 | 1065.2 | 1100.00 |

TABLE 5-3D

| Strain #4, Stock concentration (TCID50/ml) = 2.30E+05 | | | | | |
|---|---|---|---|---|---|
| Name | GP# | LN | ATCC | Strain | |
| CMV | GP2135 | SD-RFS-000175 | VR-977 | Towne | |
| start conc (TCID50/ml) | TCID50/ ml in sample tube | TCID50/ml after PBS dilution | start vol (μL) | μL of Plasma | final vol (μL) |
| 2.50E+05 | 10000.00 | 83333 | 6.0 | 144.0 | 150.00 |
| 1.00E+04 | 1000.00 | 833 | 10.0 | 90.0 | 100.00 |
| 1.00E+03 | 31.60 | 26 | 34.8 | 1065.2 | 1100.00 |

ProK was added to PBS at 3 mg/ml (for a final 0.5 mg/ml in sample) by doing the following:

TABLE 5-4

| stock ProK conc (mg/ml) | final conc (mg/ml) | start vol (μL) | vol PBS (μL) | final vol (μL) |
|---|---|---|---|---|
| 20 | 3 | 135 | 765 | 900 |

800 μL of each viral sample at 31.6 TCID50/ml was added to 160 μof PBS:ProK mixture and mixed by pipetting up and down. An inactivated viral stock from Zeptometrix, in cp/ml, was also analyzed to determine assay sensitivity. Stock was diluted in PBS by doing the following:

TABLE 5-5

| Strain #5, Stock concentration (cp/ml) = 1.00E+05. | | | | | |
|---|---|---|---|---|---|
| Name | PN# | LN# | Strain | | |
| CMV | NATCMV-0005 | 318997 | AD-169 | | |
| start conc (cp/ml) | cp/ml in sample tube | testing amount (cp/rxn) | start vol (µL) | µL of Plasma | final vol (µL) |
| 1.00E+05 | 10000 | 360 | 125.0 | 1125.0 | 1250.00 |
| 10000 | 1000 | 36 | 125.0 | 1125.0 | 1250.00 |
| 1000 | 100 | 4 | 125.0 | 1125.0 | 1250.00 |
| 100 | 10 | 0.360 | 125.0 | 1125.0 | 1250.00 |
| 10 | 1 | 0.036 | 110.0 | 990.0 | 1100.00 |

A negative control was processed and consisted of 500 µL of plasma pool with 100 µL of the PBS:ProK mixture. All samples, excluding the negative control, were processed with two extractions with three PCR reps each ext. The negative control was processed with one extraction and three PCR reps. All samples were processed on a Panther Fusion system using the following sequence file.

TABLE 5-6

| Thermocycling Conditions: | | |
|---|---|---|
| 95° C. | 2:00 min | |
| 95° C. | 0:08 min | 45 cycles |
| 60° C. | 0:25 min | |

Data analysis was performed following the parameters below:

TABLE 5-7

| Channel | CrossTalk Correction | Convergence Cycle | End Cycle Cutoff | Positivity/ CT Threshold |
|---|---|---|---|---|
| FAM | N/A | 10 | 1.50 | 1000 |
| HEX | N/A | N/A | N/A | N/A |
| ROX | N/A | N/A | N/A | N/A |
| RED647 | N/A | N/A | N/A | N/A |
| RED677 | N/A | N/A | N/A | N/A |

TABLE 5-8

| Oligomer info description | | | | |
|---|---|---|---|---|
| Oligo | SEQ ID NO. | Sequence 5' → 3' | Modifications | MW without Modifications |
| Target: CMV | | | | |
| primer | 11 | CAGATACACTATAGCCGCCG | None | 6070.95 |
| primer | 23 | CCATGGAGCTGGAGTGTCTAAAG | None | 7128.63 |
| probe | 53 | CGTGGACTCCGCCAGTAACACGTT | 5' Fluorescein, 8 mdCs, 3' BHQ1 | 7313.72 |
| Target: IC | | | | |
| primer | 83 | ATGGTCAATTAGAGACAAAG | None | 6198.08 |
| primer | 84 | CGTTCACTATTGGTCTCTGC | None | 6049.88 |
| probe | 85 | CGGAATCACAAGTCAATCATCGCGCA | 5' Q705 and 3' BHQ2 | 7933.16 |

TABLE 5-9

| Results for CMV Isolates, Concentration (TCID50/ml) = 31.6 | | | | | | | | | |
|---|---|---|---|---|---|---|---|---|---|
| Isolate | Channel | Reactivity | Average of Ct | StdDev of Ct | Average of RFU | StdDev of RFU | Average of Slope at Threshold | Average of Background RFU |
| GP2134 | FAM | 6/6 | 24.61 | 0.15 | 43877.51 | 889.12 | 591.35 | 15977.88 |
| GP2135 | FAM | 6/6 | 26.97 | 0.18 | 43629.85 | 1479.88 | 674.90 | 16211.88 |
| GP2137 | FAM | 6/6 | 16.51 | 0.43 | 45277.37 | 1272.47 | 536.65 | 16215.07 |
| GP2138 | FAM | 6/6 | 29.66 | 0.28 | 43056.36 | 535.41 | 581.36 | 16340.72 |
| GP2134 | RED677 | 6/6 | 29.31 | 0.23 | 7161.65 | 655.57 | 315.64 | 2182.68 |
| GP2135 | RED677 | 6/6 | 29.10 | 0.12 | 7090.53 | 621.66 | 330.72 | 2211.17 |
| GP2137 | RED677 | 6/6 | 29.61 | 0.40 | 6683.47 | 1201.76 | 285.08 | 2149.09 |
| GP2138 | RED677 | 6/6 | 29.09 | 0.20 | 7074.76 | 489.57 | 337.75 | 2146.82 |

TABLE 5-10

Results for NATtrol Efficiency, Isolate CMV NATtrol

| Concentration (cp/ml) | Conc. per rxn | Channel | Reactivity | Average of Cr | StdDev of Ct | Average of RFU | StdDev of RFU | Average of Slope at Threshold | Average of Background RFU |
|---|---|---|---|---|---|---|---|---|---|
| 10000 | 360 | FAM | 6/6 | 28.81 | 0.27 | 46857.58 | 1150.41 | 643.71 | 16293.91 |
| 1000 | 36 | FAM | 6/6 | 32.42 | 0.19 | 43472.73 | 1449.97 | 695.60 | 15561.52 |
| 100 | 3.6 | FAM | 6/6 | 36.22 | 0.45 | 29573.77 | 2687.53 | 655.56 | 15899.90 |
| 10 | 036 | FAM | 3/6 | 33.73 | 0.72 | 18525.04 | 4380.75 | 750.90 | 16353.88 |
| 1 | 0.036 | FAM | 0/6 | N/A | N/A | N/A | N/A | N/A | N/A |
| 10000 | 360 | RED677 | 6/6 | 27.68 | 0.20 | 7101.13 | 1162.98 | 277.61 | 2107.58 |
| 1000 | 36 | RED677 | 6/6 | 27.78 | 0.13 | 6738.36 | 524.07 | 284.32 | 1931.81 |
| 100 | 3.6 | RED677 | 6/6 | 27.96 | 0.27 | 6335.28 | 865.45 | 281.24 | 1887.57 |
| 10 | 036 | RED677 | 6/6 | 27.79 | 0.14 | 7202.59 | 538.11 | 285.82 | 2137.19 |
| 1 | 0.036 | RED677 | 6/6 | 27.44 | 0.09 | 8413.34 | 231.07 | 306.70 | 2527.32 |

Conclusion: The strain that came up very early had the lowest concentration in TCID50/ml. This isolate reached only a low titer after several weeks. However, it resulted in an early Ct. For all isolates, the true LoD for each would be lower than the strain AD-169, less than 1 TCID50/ml. LoD for the inactivated virus, NATtrol, in PBS fell between 100 and 10 cp/ml, which is at our theoretical limit for PCR. Viral strain TCID50/ml, were between 3.16 TCID50/ml and 1 TCID50/ml. BioFire was 43 and 136 cp/ml. PCR efficiency onboard the instrument produces a slope of 3.4 and an R2 larger than 0.98.

Example 6 CMV Specificity

CMV specificity was evaluated based on closest concentration possible to 1E+06 cp/ml based on CMV team conversions. CMV PPR was prepared. The following CMV PPR was prepared.

TABLE 6-1

PPR Mix

| Name | SEQ ID NO. | Units | Stock Conc | Final Conc | ×1.25 | μL |
|---|---|---|---|---|---|---|
| primer | 11 | μM | 226.00 | 1.00 | 1.25 | 5.8 |
| primer | 23 | μM | 212.10 | 1.00 | 1.25 | 6.1 |
| probe | 53 | μM | 165.40 | 0.80 | 1.00 | 6.3 |
| primer | 83 | μM | 193.09 | 0.60 | 0.75 | 4.0 |
| primer | 84 | μM | 266.80 | 0.60 | 0.75 | 2.9 |
| probe | 85 | μM | 94.20 | 0.40 | 0.50 | 5.5 |
| MgC12 | | mM | 1000.00 | 5.00 | 6.25 | 6.5 |
| Kc1 | | mM | 2000.00 | 65.00 | 81.25 | 42.3 |
| Water: | | | | | | 960.6 |
| Total: | | | | | | 1040.0 |

One recon tube was prepared with 1000 μL of PPR mix and 400 μL of oil on top. All tubes were spun down before loading onto a Panther Fusion system. 8 Panels from SD-AJH-000263 were tested on the Panther Fusion system with one extraction and three PCR reps per ext. A positive control was tested and consisted of the CMV plasmid at 1000 cp/ml:

TABLE 6-2

| Step 1 | Initial Dilutions | | | | |
|---|---|---|---|---|---|
| Stock conc (cp/ml) | final conc (cp/ml) | Stock vol (μL) | μL of STM (μL) | final vol needed (μL) | |
| 1.00E+07 | 1.00E+05 | 5 | 495 | 500 | |
| 1.00E+05 | 1.00E+04 | 13 | 113 | 125 | |
| **Step 2** | **CMV Calibrator 6 in PBS Concentration Needed (Calculation)** | | | | |
| start conc (cp/ml) | testing amount (cp) per 5 ul rxn | cp/ml in 'specimen' tube | start vol (μL) | μL of STM | final vol (μL) |
| 1.00E+04 | 36 | 1000.00 | 70.0 | 630.0 | 700.00 |

A negative control was processed and consisted of 600 μL of STM. Both controls were processed with one extraction and one PCR rep to determine if PPR was made correctly. All samples were processed on a Panther Fusion system using the following sequence file.

TABLE 6-3

| Thermocycling Conditions: | | |
|---|---|---|
| 95° C. | 2:00 min | |
| 95° C. | 0:08 min | 45 cycles |
| 60° C. | 0:25 min | |

Data analysis was performed following the parameters below:

TABLE 6-4

| Channel | CrossTalk Correction | Convergence Cycle | End Cycle Cutoff | Positivity/ CT Threshold |
|---|---|---|---|---|
| FAM | NIA | 10 | 1.50 | 1000 |
| HEX | N/A | N/A | N/A | N/A |
| ROX | N/A | N/A | N/A | N/A |
| RED647 | N/A | N/A | N/A | N/A |
| RED677 | N/A | 10 | N/A | 500 |

TABLE 6-5

| Oligomer info - description. CMV oligo list | | | | |
|---|---|---|---|---|
| Oligo name | SEQ ID NO. | Sequence 5' → 3' | Modifications | MW without Modifications |
| Target: CMV | | | | |
| primer | 11 | CAGATACACTATAGCCGCCG | None | 6070.95 |
| primer | 23 | CCATGGAGCTGGAGTGTCTAAAG | None | 7128.63 |
| probe | 53 | CGTGGACTCCGCCAGTAACACGTT | 5' Fluorescein, 8 mdCs, 3' BHQ1 | 7313.72 |
| Target: IC | | | | |
| primer | 83 | ATGGTCAATTAGAGACAAAG | None | 6198.08 |
| primer | 84 | CGTTCACTATTGGTCTCTGC | None | 6049.88 |
| probe | 85 | CGGAATCACAAGTCAATCATCGCGCA | 5' Q705 and 3' BHQ2 | 7933.16 |

TABLE 6-6

| Row Labels | Re-activity | Avg Ct | SD Ct | Avg RFU | SD RFU | Δ Ct |
|---|---|---|---|---|---|---|
| FAM | 1 | 34.27 | | 13151.99 | 222212.30 | |
| Neg Ctrl | | | | | | |
| Panel 1 | | | | | | |
| Panel 2 | | | | | | |
| Panel 3 | | | | 330.11 | | |
| Panel 4 | | | | | | |
| Panel 5 | | | | | | |
| Panel 6 | | | | 325.31 | | |
| Panel 7 | | | | | | |
| Panel 8 | | | | | | |
| Pos Ctrl | 1 | 34.27 | | 38800.54 | | |
| Quasar 705 | 26 | 28.52 | 1.13 | 7384.66 | 831.24 | |
| Neg Ctrl | 1 | 27.34 | | 7415.28 | | |
| Panel 1 | 3 | 29.25 | 0.29 | 7088.86 | 1392.56 | 1.91 |
| Panel 2 | 3 | 27.62 | 0.09 | 7294.40 | 415.37 | 0.28 |
| Panel 3 | 3 | 29.51 | 0.06 | 6869.81 | 565.22 | 2.17 |
| Panel 4 | 3 | 28.84 | 0.08 | 7552.98 | 329.69 | 1.50 |
| Panel 5 | 3 | 29.06 | 0.03 | 7563.86 | 431.69 | 1.72 |
| Panel 6 | 3 | 27.39 | 0.37 | 7101.88 | 1752.35 | 0.05 |

TABLE 6-6-continued

| Row Labels | Re-activity | Avg Ct | SD Ct | Avg RFU | SD RFU | Δ Ct |
|---|---|---|---|---|---|---|
| Panel 7 | 3 | 27.14 | 0.13 | 7601.83 | 689.21 | −0.20 |
| Panel 8 | 3 | 30.32 | 0.01 | 7417.33 | 216.86 | 2.98 |
| Pos Ctrl | 1 | 26.85 | | 9112.94 | | −0.49 |

Panels with high cell/cp count showed delay in IC Ct.IC-9T

Conclusion: All panels were negative for CMV and positive for IC.

Example 7. Analysis of CMV Positive and CMV Negative Plasma Clinical Samples

50 CMV positive and 50 CMV negative plasma samples were evaluated to determine how well the CMV PCR assays perform. Specimens were tested with 1:0.2 PBS with 10×TCO and 0.5 mg/ml ProK. The following PPR mixes was prepared:

TABLE 7-1

| PPR Mixes. | | | | | | |
|---|---|---|---|---|---|---|
| Name | SEQ ID NO. | Units | Stock Conc | Final Conc | ×1.25 | μL |
| primer | 11 | μM | 183.80 | 0.60 | 0.75 | 20.00 |
| primer | 23 | μM | 158.80 | 0.60 | 0.75 | 23.1 |
| probe | 53 | μM | 100.00 | 0.40 | 0.50 | 24.5 |
| DNA IC Primers | 83, 84 | μM | 50.00 | 1.00 | 1.00 | 98.0 |
| DNA IC Probe | 85 | μM | 50.00 | 1.00 | 1.00 | 98.0 |
| MgC12 | | mM | 1000.00 | 5.00 | 6.25 | 30.6 |
| KC1 | | mM | 2000.00 | 65.00 | 81.25 | 199.1 |
| Water | | | | | | 4406.7 |
| Total: | | | | | | 4900.0 |

Four PPR had 1200 μL added to Recon tube and 400 μL of oil added to top.

TABLE 7-2

| Name | SEQ ID NO. | Units | Stock Conc | Final Conc | ×1.25 | μL |
|---|---|---|---|---|---|---|
| primer | 11 | μM | 183.80 | 0.60 | 0.75 | 20.00 |
| primer | 23 | μM | 158.80 | 0.60 | 0.75 | 23.1 |
| probe | 53 | μM | 100.00 | 0.40 | 0.50 | 24.5 |
| DNA IC Primers | 83, 84 | μM | 50.00 | 1.00 | 1.00 | 98.0 |
| DNA IC Probe | 85 | μM | 50.00 | 1.00 | 1.00 | 98.0 |

TABLE 7-2-continued

| Name | SEQ ID NO. | Units | Stock Conc | Final Conc | ×1.25 | μL |
|---|---|---|---|---|---|---|
| MgC12 | | mM | 1000.00 | 5.00 | 6.25 | 30.6 |
| KC1 | | mM | 2000.00 | 65.00 | 81.25 | 199.1 |
| Water | | | | | | 4406.7 |
| Total: | | | | | | 4900.0 |

Four PPR had 1200 μL added to a reconstitution tube and 400 μL of oil added to top. 50 CMV negative and 50 CMV positive clinical plasma was tested with each PPR mix. 10× extra TCO and 3 mg/ml ProK were added to PBS and 100 μL added to labeled tubes: 0.666 mg per 1 L, 0.000666 mg/ml, 0.0002997 mg/rxn, 360 μL sample input, 0.0003 mg in sample/reaction, 0.0030 mg 10× in sample/reaction

TABLE 7-3

Processing. 1:0.2 Processing with PBS

| TCO at 10× | |
|---|---|
| 60 μL | Volume per sample pull |
| 0.00005 mg/μL | Concentration in sample |
| 2.46 mg/μL | Concentration of TCO |
| 223.6 μL | volume of stock TCO to add |
| 9126.4 μL | Volume of diluent |
| 1650.0 μL | 20 mg/ml ProK to determine volume of TCO and diluent |
| 11000.0 μL | Total volume of diluent needed |

Negatives processed included 600 μL of PBS. Positive control consisted of CMV plasmid in PBS spiked at 50 cp/rxn:

Step 1. Initial Dilutions

Stock Concentration=$1.00\times10^7$

Final Concentration=$1.00\times10^5$

Stock Volume (μL)=10

μL of PBS=990

Final Volume (μL) 1000

Step 2. CMV Calibrator in STM, Concentration Needed (Calculation)

start conc. (cp/ml)=$1.00\times10^5$ testing amount (cp) per 5 μL rxn=50 cp/mL in 'specimen' tube=1388.89 start volume (μL)=22

μL of PBS=1578 final volume (μL)=1600

All clinical specimen had 500 μL added to a tube containing 100 μL of the PBS/ProK/TCO mixture from 2.1 and mixed by mixing up and down three times. Samples were tested by following the table below:

TABLE 7-4

Samples to be processed.

| Sample | Concentration | #Ext | #PCR reps per ext | Final n | #PPR mixes |
|---|---|---|---|---|---|
| 50 CMV Neg Plasma | N/A | 1 | 3 | 150 (3 per spec) | 1 |
| 50 CMV Pos Plasma | N/A | 1 | 3 | 150 (3 per spec) | 1 |
| CMV Positive Ctrl | 50 | 1 | 3 | 3 | 1 |
| Negative Ctrl (STM) | N/A | 1 | 3 | 3 | 1 |

25 positive and 25 negative samples were processed on one instrument each. Samples were processed on a Panther Fusion system using the following DNA thermocycling conditions.

TABLE 7-5

Thermocycling Conditions:

| | | |
|---|---|---|
| 95° C. | 2:00 min | |
| 95° C. | 0:08 min | 45 cycles |
| 60° C. | 0:25 min | |

Data analysis was performed following the parameters below:

TABLE 7-6

| Channel | CrossTalk Correction | Convergence Cycle | End Cycle Cutoff | Positivity/CT Threshold |
|---|---|---|---|---|
| FAM | N/A | 10 | 150 | 1000 |
| HEX | N/A | N/A | N/A | N/A |
| ROX | N/A | N/A | N/A | N/A |
| RED647 | N/A | N/A | N/A | N/A |
| RED677 | N/A | 10 | N/A | 500 |

Discordant samples, along with one high and one low positive, were processed for CMV TMA testing.

Oligo info- description.

| Oligo name | SEQ ID NO. | Sequence 5' → 3' | Modifications | MW without Modifications | MW with Modifications |
|---|---|---|---|---|---|
| Target CMV | | | | | |
| primer | 11 | CAGATACACTATAGCCGCCG | None | 6070.95 | 6070.95 |
| primer | 23 | CCATGGAGCTGGAGTGTCTAAAG | None | 6070.95 | 7128.63 |
| probe | 53 | CGTGGACTCCGCCAGTAACACGTT | 5' Fluorescein, 8 mdCs, 3' BHQ1 | N/A | N/A |
| Target: TCO | | | | | |
| | | 3' blocked TCO at 2.46 mg/mL | | | |

TABLE 7-8

| Results-Description Summary Table - Negatives | | | | | | | |
|---|---|---|---|---|---|---|---|
| Row labels | Reactivity | Avg Ct | SD Ct | Avg RFU | SD RFU | Avg T-Slope | Avg Background |
| FAM | 24 | 35.02 | 2.45 | 19180.63 | 11070.81 | 659.40 | 9679.28 |
| CMV_NEG01 | | | | 165.95 | | | 9505.46 |
| CMV_NEG02 | | | | | | | 9980.55 |
| CMV_NEG03 | | | | 157.18 | | | 8236.27 |
| CMV_NEG04 | | | | | | | 9716.18 |
| CMV_NEG05 | | | | 217.71 | | | 9608.25 |
| CMV_NEG06 | | | | | | | 10774.34 |
| CMV_NEG07 | | | | | | | 9770.91 |
| CMV_NEG08 | | | | | | | 9343.42 |
| CMV_NEG09 | | | | | | | 9777.72 |
| CMV_NEG010 | | | | | | | 9904.58 |
| CMV_NEG11 | | | | | | | 9031.41 |
| CMV_NEG12 | | | | | | | 9782.35 |
| CMV_NEG13 | | | | | | | 9501.53 |
| CMV_NEG14 | | | | | | | 9778.12 |
| CMV_NEG15 | | | | | | | 9151.22 |
| CMV_NEG16 | 3 | 36.59 | 0.64 | 20641.69 | 3115.71 | 624.06 | 9306.88 |
| CMV_NEG17 | | | | | | | 9716.38 |
| CMV_NEG18 | | | | | | | 9539.19 |
| CMV_NEG19 | | | | | | | 9496.45 |
| CMV_NEG20 | | | | | | | 9312.39 |
| CMV_NEG21 | | | | | | | 9876.50 |
| CMV_NEG22 | 3 | 37.06 | 0.36 | 9026.33 | 893.75 | 595.31 | 10217.59 |
| CMV_NEG23 | | | | | | | 9935.86 |
| CMV_NEG24 | | | | | | | 9587.36 |
| CMV_NEG25 | | | | | | | 9647.86 |
| CMV_NEG26 | 3 | 35.12 | 0.35 | 22196.54 | 2464.31 | 662.04 | 9576.74 |
| CMV_NEG27 | | | | | | | 9410.81 |
| CMV_NEG28 | | | | | | | 10434.32 |
| CMV_NEG29 | 3 | 38.17 | 0.81 | 10965.20 | 2227.46 | 604.45 | 7782.80 |
| CMV_NEG30 | 3 | 29.85 | 0.17 | 31816.19 | 1347.29 | 631.41 | 9196.89 |
| CMV_NEG31 | | | | | | | 9548.90 |
| CMV_NEG32 | | | | | | | 9038.69 |
| CMV_NEG33 | | | | | | | 9006.76 |
| CMV_NEG34 | | | | | | | 9607.79 |
| CMV_NEG35 | | | | | | | 10491.06 |
| CMV_NEG36 | | | | | | | 9854.39 |
| CMV_NEG37 | 3 | 33.80 | 0.27 | 24473.76 | 3059.18 | 713.56 | 9860.18 |
| CMV_NEG38 | | | | | | | 9889.25 |
| CMV_NEG39 | | | | | | | 10598.49 |
| CMV_NEG40 | | | | | | | 9175.02 |
| CMV_NEG41 | | | | 793.30 | | | 9525.73 |
| CMV_NEG42 | | | | | | | 10373.18 |
| CMV_NEG43 | | | | | | | 9432.61 |
| CMV_NEG44 | | | | | | | 9844.92 |
| CMV_NEG45 | | | | | | | 9965.28 |
| CMV_NEG46 | | | | | | | 9079.39 |
| CMV_NEG47 | | | | | | | 9139.32 |
| CMV_NEG48 | | | | | | | 9921.59 |
| CMV_NEG49 | | | | | | | 10293.14 |
| CMV_NEG50 | | | | | | | 10288.86 |
| Neg Ctrl | | | | | | | 9813.15 |
| Pos Ctrl | 6 | 34.79 | 0.44 | 29727.41 | 1837.19 | 722.17 | 10609.87 |
| Quasar 705 | 162 | 27.70 | 0.56 | 10541.46 | 2479.83 | 336.55 | 2945.69 |
| CMV_NEG01 | 3 | 28.20 | 0.19 | 8278.23 | 937.80 | 302.61 | 2462.38 |
| CMV_NEG02 | 3 | 27.50 | 0.13 | 13100.16 | 423.90 | 319.85 | 3506.63 |
| CMV_NEG03 | 3 | 27.81 | 0.21 | 8019.66 | 966.07 | 260.48 | 2223.33 |
| CMV_NEG04 | 3 | 27.12 | 0.06 | 12570.09 | 249.79 | 393.77 | 3396.74 |
| CMV_NEG05 | 3 | 27.11 | 0.02 | 12830.85 | 501.76 | 401.48 | 3458.49 |
| CMV_NEG06 | 3 | 28.23 | 0.03 | 8708.11 | 760.66 | 354.29 | 2506.10 |
| CMV_NEG07 | 3 | 27.61 | 0.14 | 12793.01 | 952.37 | 302.92 | 3618.63 |
| CMV_NEG08 | 3 | 27.96 | 0.18 | 7781.29 | 843.55 | 285.85 | 2250.49 |
| CMV_NEG09 | 3 | 27.26 | 0.20 | 12174.47 | 712.91 | 371.85 | 3298.30 |
| CMV_NEG010 | 3 | 27.69 | 0.16 | 12463.38 | 227.71 | 283.97 | 3366.58 |
| CMV_NEG11 | 3 | 27.85 | 0.31 | 7393.95 | 1458.57 | 298.39 | 2158.95 |
| CMV_NEG12 | 3 | 27.31 | 0.10 | 14090.72 | 236.42 | 340.95 | 3864.59 |
| CMV_NEG13 | 3 | 27.75 | 0.13 | 8055.38 | 405.88 | 270.20 | 2249.87 |
| CMV_NEG14 | 3 | 27.48 | 0.16 | 13217.16 | 1222.87 | 327.96 | 3681.86 |
| CMV_NEG15 | 3 | 27.84 | 0.08 | 8841.80 | 451.66 | 257.74 | 2553.35 |
| CMV_NEG16 | 3 | 27.61 | 0.08 | 8483.60 | 325.13 | 288.08 | 2310.01 |
| CMV_NEG17 | 3 | 27.15 | 0.04 | 12133.91 | 507.24 | 394.39 | 3240.29 |
| CMV_NEG18 | 3 | 27.53 | 0.05 | 9763.05 | 116.05 | 305.96 | 2725.39 |
| CMV_NEG19 | 3 | 28.06 | 0.08 | 7709.64 | 221.87 | 390.87 | 2234.99 |
| CMV_NEG20 | 3 | 27.22 | 0.06 | 12512.16 | 356.29 | 378.06 | 3510.12 |
| CMV_NEG21 | 3 | 27.05 | 0.05 | 12654.44 | 901.88 | 424.72 | 3517.62 |

TABLE 7-8-continued

Results-Description Summary Table - Negatives

| Row labels | Reactivity | Avg Ct | SD Ct | Avg RFU | SD RFU | Avg T-Slope | Avg Background |
|---|---|---|---|---|---|---|---|
| CMV_NEG22 | 3 | 27.63 | 0.10 | 9642.98 | 660.78 | 290.68 | 2800.27 |
| CMV_NEG23 | 3 | 26.96 | 0.19 | 12970.02 | 1292.15 | 299.86 | 3500.70 |
| CMV_NEG24 | 3 | 28.27 | 0.12 | 7743.01 | 548.52 | 349.40 | 2242.52 |
| CMV_NEG25 | 3 | 27.28 | 0.09 | 11809.89 | 748.40 | 369.13 | 3165.15 |
| CMV_NEG26 | 3 | 27.21 | 0.02 | 14922.82 | 535.58 | 373.51 | 4189.52 |
| CMV_NEG27 | 3 | 27.09 | 0.07 | 12659.64 | 766.25 | 409.73 | 3549.53 |
| CMV_NEG28 | 3 | 27.72 | 0.04 | 8211.68 | 88.33 | 277.18 | 2403.99 |
| CMV_NEG29 | 3 | 28.16 | 0.10 | 7504.17 | 252.72 | 368.75 | 2074.50 |
| CMV_NEG30 | 3 | 27.16 | 0.11 | 11809.10 | 806.18 | 394.91 | 3280.02 |
| CMV_NEG31 | 3 | 28.07 | 0.06 | 8208.00 | 385.40 | 400.76 | 2313.67 |
| CMV_NEG32 | 3 | 27.47 | 0.07 | 11220.89 | 322.48 | 333.07 | 3042.27 |
| CMV_NEG33 | 3 | 27.39 | 0.09 | 11611.78 | 570.99 | 340.92 | 3175.07 |
| CMV_NEG34 | 3 | 27.77 | 0.17 | 8754.57 | 919.88 | 267.80 | 2487.99 |
| CMV_NEG35 | 3 | 27.04 | 0.11 | 13438.94 | 1092.50 | 363.86 | 3792.99 |
| CMV_NEG36 | 3 | 27.66 | 0.11 | 12611.80 | 880.25 | 290.55 | 3402.69 |
| CMV_NEG37 | 3 | 27.16 | 0.17 | 11646.95 | 504.87 | 399.41 | 3244.26 |
| CMV_NEG38 | 3 | 27.66 | 0.19 | 13771.92 | 1256.87 | 292.31 | 3862.28 |
| CMV_NEG39 | 3 | 28.01 | 0.08 | 9103.86 | 136.87 | 345.99 | 2631.54 |
| CMV_NEG40 | 3 | 27.45 | 0.09 | 11950.52 | 717.75 | 326.49 | 3273.46 |
| CMV_NEG41 | 3 | 27.65 | 0.23 | 9125.29 | 1077.64 | 288.39 | 2643.28 |
| CMV_NEG42 | 3 | 27.99 | 0.08 | 8406.86 | 117.63 | 355.25 | 2435.33 |
| CMV_NEG43 | 3 | 28.16 | 0.07 | 7808.83 | 432.96 | 371.47 | 2202.22 |
| CMV_NEG44 | 3 | 30.30 | 0.15 | 7563.40 | 1110.11 | 347.40 | 2211.04 |
| CMV_NEG45 | 3 | 27.80 | 0.11 | 8679.01 | 534.57 | 265.29 | 2437.75 |
| CMV_NEG46 | 3 | 28.40 | 0.12 | 7219.49 | 559.59 | 324.58 | 2087.66 |
| CMV_NEG47 | 3 | 27.41 | 0.09 | 12323.21 | 896.76 | 332.61 | 3379.38 |
| CMV_NEG48 | 3 | 28.47 | 0.21 | 8309.92 | 604.04 | 318.33 | 2426.36 |
| CMV_NEG49 | 3 | 28.10 | 0.05 | 12618.12 | 332.70 | 409.44 | 3515.56 |
| CMV_NEG50 | 3 | 28.72 | 0.18 | 8211.11 | 752.29 | 272.75 | 2401.95 |
| Neg Ctrl | 6 | 27.61 | 0.50 | 10949.50 | 3610.17 | 385.14 | 3034.59 |
| Pos Ctrl | 6 | 27.43 | 0.39 | 11953.46 | 3830.91 | 334.55 | 3343.93 |

Note: Multicore versus Singlecore resulted in differences in RED677 background and therefore differences in overall RFU values. Note: CMV_Neg22 resulted in abnormal curve and may be indicative of base pair mismatch in probe.

TABLE 7-9

Positives Summary Table:

| Row labels | Reactivity | Avg Ct | SD Ct | Avg RFU | SD RFU | Avg T-Slope | Avg Background |
|---|---|---|---|---|---|---|---|
| FAM | 107 | 34.63 | 2.98 | 20133.76 | 8529.65 | 647.71 | 9866.41 |
| CMV103 | 3 | 34.11 | 0.28 | 22487.90 | 698.30 | | |
| CMV104 | 3 | 35.64 | 0.32 | 15640.17 | 1589.68 | | |
| CMV105 | 3 | 32.52 | 0.06 | 30176.48 | 1371.91 | | |
| CMV106 | | | | | | | |
| CMV107 | 3 | 38.04 | 1.00 | 1215.50 | 2836.14 | | |
| CMV108 | 3 | 35.02 | 0.37 | 16485.25 | 3799.91 | | |
| CMV109 | 2 | 38.41 | 1.51 | 9605.86 | 3007.82 | | |
| CMV110 | 3 | 35.13 | 0.55 | 19506.53 | 3134.66 | | |
| CMV111 | 3 | 29.06 | 0.02 | 39634.41 | 2176.35 | | |
| CMV112 | 3 | 35.54 | 0.47 | 6113.01 | 1136.67 | | |
| CMV113 | 3 | 35.23 | 0.55 | 17592.99 | 3135.22 | | |
| CMV114 | 3 | 33.97 | 0.40 | 28275.45 | 1187.84 | | |
| CMV115 | 2 | 38.21 | 1.57 | 9763.61 | 6226.22 | | |
| CMV116 | 2 | 38.97 | 0.23 | 14393.71 | 1983.19 | | |
| CMV117 | 3 | 36.17 | 0.15 | 19902.97 | 865.83 | | |
| CMV118 | 3 | 36.57 | 0.37 | 14314.70 | 2111.78 | | |
| CMV119 | 2 | 38.47 | 1.63 | 7614.08 | 5782.31 | | |
| CMV120 | 3 | 34.02 | 0.26 | 22842.92 | 2031.90 | | |
| CMV121 | 3 | 28.68 | 0.02 | 34949.99 | 2608.50 | | |
| CMV122 | 3 | 29.89 | 0.01 | 30772.27 | 2085.53 | | |
| CMV123 | 3 | 36.09 | 0.48 | 17483.59 | 597.54 | | |
| CMV124 | 3 | 32.69 | 0.21 | 27675.45 | 1510.52 | | |
| CMV125 | 3 | 34.68 | 0.52 | 26087.30 | 2118.18 | | |
| CMV126 | | | | | | | |
| CMV127 | | | | | | | |
| CMV128 | 1 | 41.82 | | 1573.44 | | | |
| CMV129 | 3 | 34.62 | 0.49 | 19823.22 | 7177.17 | | |

TABLE 7-9-continued

Positives Summary Table:

| Row labels | Reactivity | Avg Ct | SD Ct | Avg RFU | SD RFU | Avg T-Slope | Avg Background |
|---|---|---|---|---|---|---|---|
| CMV130 | | | | | | | |
| CMV131 | 3 | 31.19 | 0.18 | 26944.23 | 1382.41 | | |
| CMV132 | 3 | 29.17 | 0.02 | 27304.69 | 2860.31 | | |
| CMV133 | | | | | | | |
| CMV134 | 3 | 34.92 | 0.31 | 15915.96 | 1714.87 | | |
| CMV135 | 2 | 38.44 | 1.77 | 6961.12 | 4350.64 | | |
| CMV136 | 3 | 37.50 | 1.21 | 16231.34 | 3850.76 | | |
| CMV137 | 3 | 31.52 | 0.07 | 23181.91 | 1746.66 | | |
| CMV138 | 3 | 36.76 | 0.52 | 11502.23 | 2353.21 | | |
| CMV139 | 1 | 38.92 | | 14512.84 | | | |
| CMV140 | 3 | 30.28 | 0.08 | 32973.36 | 2745.59 | | |
| CMV141 | 3 | 35.10 | 0.30 | 23893.42 | 1949.95 | | |
| CMV142 | 3 | 32.07 | 0.18 | 24530.95 | 2204.73 | | |
| CMV143 | 1 | 37.05 | | 20537.53 | | | |
| CMV144 | 1 | 38.96 | | 10924.66 | | | |
| CMV145 | 3 | 38.24 | 0.88 | 11256.69 | 1614.80 | | |
| CMV146 | | | | | | | |
| CMV147 | | | | | | | |
| CMV148 | 3 | 34.44 | 0.19 | 21155.58 | 388.28 | | |
| CMV149 | | | | | | | |
| CMV150 | 3 | 35.69 | 0.54 | 13285.74 | 1172.38 | | |
| CMV151 | | | | | | | |
| CMV152 | | | | | | | |
| Quasar 705 | 150 | 27.65 | 0.54 | 10519.86 | 2429.34 | 335.79 | 2997.74 |
| CMV103 | 3 | 27.17 | 0.03 | 13560.20 | 604.25 | 379.97 | 3799.06 |
| CMV104 | 3 | 26.85 | 0.11 | 12947.31 | 826.22 | 322.75 | 3572.89 |
| CMV105 | 3 | 27.25 | 0.07 | 14927.60 | 1200.12 | 371.36 | 4207.77 |
| CMV106 | 3 | 27.21 | 0.09 | 13348.65 | 638.53 | 375.95 | 3729.10 |
| CMV107 | 3 | 27.18 | 0.03 | 12818.08 | 489.13 | 377.55 | 3514.32 |
| CMV108 | 3 | 27.22 | 0.14 | 12811.85 | 703.45 | 374.57 | 3520.28 |
| CMV109 | 3 | 27.17 | 0.10 | 12259.93 | 1281.05 | 387.23 | 3399.02 |
| CMV110 | 3 | 27.34 | 0.19 | 11664.95 | 911.25 | 348.49 | 3227.66 |
| CMV111 | 3 | 27.08 | 0.03 | 13616.99 | 695.34 | 409.00 | 3694.38 |
| CMV112 | 3 | 27.97 | 0.10 | 11244.60 | 391.02 | 297.23 | 3838.50 |
| CMV113 | 3 | 27.20 | 0.13 | 12811.28 | 911.09 | 380.19 | 3617.56 |
| CMV114 | 3 | 27.20 | 0.07 | 11825.66 | 260.57 | 390.43 | 3147.06 |
| CMV115 | 3 | 27.38 | 0.07 | 12704.20 | 245.20 | 346.56 | 3563.17 |
| CMV116 | 3 | 27.14 | 0.07 | 14647.53 | 653.66 | 403.05 | 4096.89 |
| CMV117 | 3 | 27.19 | 0.02 | 13552.16 | 1306.15 | 386.79 | 3899.15 |
| CMV118 | 3 | 27.51 | 0.10 | 13074.40 | 978.87 | 313.59 | 3716.47 |
| CMV119 | 3 | 27.08 | 0.08 | 12647.41 | 876.00 | 413.89 | 3574.38 |
| CMV120 | 3 | 27.08 | 0.01 | 12621.98 | 266.71 | 410.04 | 3570.06 |
| CMV121 | 3 | 27.82 | 0.22 | 12086.61 | 1194.60 | 267.27 | 3479.34 |
| CMV122 | 3 | 27.12 | 0.05 | 11805.25 | 302.89 | 405.27 | 3330.06 |
| CMV123 | 3 | 27.11 | 0.11 | 12539.09 | 731.44 | 415.83 | 3538.51 |
| CMV124 | 3 | 27.24 | 0.08 | 11660.21 | 291.58 | 375.92 | 3209.12 |
| CMV125 | 3 | 27.31 | 0.09 | 12684.72 | 333.91 | 358.41 | 3534.64 |
| CMV126 | 3 | 27.27 | 0.03 | 12688.54 | 138.67 | 370.32 | 3489.96 |
| CMV127 | 3 | 27.44 | 0.09 | 11283.25 | 627.80 | 333.75 | 3120.54 |
| CMV128 | 3 | 27.94 | 0.11 | 8540.51 | 194.45 | 302.49 | 2578.45 |
| CMV129 | 3 | 27.64 | 0.10 | 9905.37 | 574.76 | 283.42 | 2878.75 |
| CMV130 | 3 | 27.87 | 0.22 | 9232.92 | 1159.03 | 309.21 | 2609.39 |
| CMV131 | 3 | 27.64 | 0.15 | 9127.40 | 596.00 | 286.45 | 2596.99 |
| CMV132 | 3 | 27.70 | 0.04 | 8109.12 | 645.03 | 278.04 | 2400.68 |
| CMV133 | 3 | 28.15 | 0.11 | 8280.58 | 765.45 | 380.61 | 2328.72 |
| CMV134 | 3 | 27.75 | 0.18 | 8189.18 | 977.41 | 268.67 | 2350.64 |
| CMV135 | 3 | 27.52 | 0.23 | 8829.98 | 1129.23 | 309.65 | 2513.58 |
| CMV136 | 3 | 27.62 | 0.05 | 10210.75 | 371.40. | 293.36 | 2822.76 |
| CMV137 | 3 | 27.73 | 0.05 | 7938.01 | 242.53 | 271.11 | 2287.87 |
| CMV138 | 3 | 28.26 | 0.01 | 7738.64 | 81.01 | 346.61 | 2184.86 |
| CMV139 | 3 | 28.66 | 0.12 | 8737.98 | 749.69 | 279.73 | 2485.84 |
| CMV140 | 3 | 28.24 | 0.11 | 7530.15 | 759.54 | 347.86 | 2223.98 |
| CMV141 | 3 | 27.99 | 0.07 | 8830.03 | 637.02 | 347.85 | 2580.33 |
| CMV142 | 3 | 27.71 | 0.04 | 8370.79 | 198.58 | 274.86 | 2579.26 |
| CMV143 | 3 | 28.05 | 0.09 | 8828.81 | 334.70 | 338.76 | 2674.11 |
| CMV144 | 3 | 27.72 | 0.11 | 7701.00 | 469.96 | 278.53 | 2271.82 |
| CMV145 | 3 | 28.08 | 0.31 | 7538.35 | 1161.77 | 270.93 | 2221.28 |
| CMV146 | 3 | 29.82 | 0.02 | 7773.86 | 260.46 | 261.80 | 2361.77 |
| CMV147 | 3 | 28.29 | 0.34 | 6531.12 | 897.09 | 342.39 | 1917.27 |
| CMV148 | 3 | 27.96 | 0.08 | 7782.09 | 142.35 | 302.88 | 2388.56 |
| CMV149 | 3 | 28.53 | 0.14 | 8286.81 | 431.17 | 206.82 | 2381.09 |
| CMV150 | 3 | 28.01 | 0.12 | 7689.49 | 685.79 | 288.92 | 2195.03 |
| CMV151 | 3 | 28.07 | 0.14 | 8689.86 | 895.88 | 342.60 | 2470.46 |
| CMV152 | 3 | 27.83 | 0.08 | 7768.13 | 354.91 | 258.84 | 2183.93 |

TABLE 7-10

| Log10 conversion: | | |
|---|---|---|
| Roche Test Log10 (IU/ml) | Internal Log10 (IU/ml) | Difference (IU/ml) |
| 5.20 | 4.78 | −0.41 |
| 4.77 | 4.67 | −0.09 |
| 3.97 | 4.64 | 0.67 |
| 3.96 | 4.43 | 0.47 |
| 4.56 | 4.32 | −0.24 |
| 4.06 | 4.05 | −0.01 |
| 3.46 | 3.96 | 0.50 |
| 3.76 | 3.80 | 0.03 |
| 3.58 | 3.66 | 0.08 |
| 4.49 | 3.61 | −0.88 |
| 2.89 | 3.24 | 0.35 |
| 3.38 | 3.23 | −0.15 |
| 3.17 | 3.20 | 0.04 |
| 3.13 | 3.11 | −0.02 |
| 3.25 | 3.06 | −0.19 |
| 3.32 | 3.04 | −0.28 |
| 3.66 | 2.97 | −0.69 |
| 2.92 | 2.94 | 0.02 |
| 3.07 | 2.92 | −0.15 |
| 3.42 | 2.91 | −0.51 |
| 3.02 | 2.88 | −0.14 |
| 3.01 | 2.79 | −0.22 |
| 3.15 | 2.76 | −0.40 |
| 3.05 | 2.74 | −0.30 |
| 3.55 | 2.63 | −0.93 |
| 3.68 | 2.60 | −1.08 |
| 2.90 | 2.49 | −0.41 |
| 3.45 | 2.43 | −1.02 |
| 3.13 | 2.35 | −0.78. |
| 3.13 | 2.22 | −0.91 |
| 3.33 | 2.06 | −1.27 |
| 3.47 | 2.01 | −1.46 |
| 3.40 | 2.00 | −1.40 |
| 2.72 | 1.95 | −0.77 |
| 3.02 | 1.94 | −1.07 |
| 3.43 | 1.94 | −1.50 |
| 3.70 | 1.81 | −1.89 |
| 3.31 | 1.79 | −1.52 |
| 3.16 | 1.79 | −1.36 |
| 3.26 | 0.96 | −2.30 |

Note: CMV112 resulted in abnormal curve and may be indicative of base pair mismatch in probe.

TABLE 7-11

| Positive by Roche Test and Negative by CMV Assay | | | | | |
|---|---|---|---|---|---|
| Row Labels | Roche Results (IU/ml) | Roche Results (cp/ml) | CMV TMA Assay Result (50%) cp/ml | CMV TMA Assay Result Specimen cp/ml | cp/rxn from TMA results |
| CMV106 | 1090 | 1198 | 60 | 120 | 3 |
| CMV126 | 2490 | 2736 | 0 | 0 | 0 |
| CMV127 | 2610 | 2868 | 11 | 22 | 1 |
| CMV130 | 3200 | 3516 | 3 | 6 | 0 |
| CMV133 | 3100 | 3407 | 57 | 114 | 3 |
| CMV146 | 2220 | 2440 | 81 | 162 | 5 |
| CMV147 | 1510 | 1659 | 26 | 52 | 1 |
| CMV149 | 1570 | 1725 | 8 | 16 | 0 |
| CMV151 | 2410 | 2648 | 0 | 0 | 0 |
| CMV152 | 850 | 934 | 23 | 46 | 1 |

TABLE 7-12

| CMV PCR and CMV TMA Quantitation Correlation. | |
|---|---|
| PCR | TMA |
| 36.59 | 12.76178 |
| 37.06 | 13.51685 |

TABLE 7-12-continued

| CMV PCR and CMV TMA Quantitation Correlation. | |
|---|---|
| PCR | TMA |
| 35.12 | 12.6159 |
| 38.17 | 14.21081 |
| 29.85 | 10.16029 |
| 33.80 | 11.95764 |
| 23.68 | 9.117215 |
| 38.24 | 14.16563 |

Note: All samples testing negative using the COBAS TaqMan® CMV Test ("Roche" or "Roche Test") (Roche Diagnostics, North America) and positive by CMV PCR were positive by CMV TMA Quantification. Those values, along with the low and high positive returned a strong correlation between TTime and Ct of the two assays. TTime is a term used to represent the amplification time when a sample signal value exceeds a threshold signal value (typically a predetermined background signal value) during an amplification and detection reaction of the sample.

Conclusion: With initial testing of 50 Roche test negative plasma specimen, 44/50 were negative by CMV PCR (80%). 6 discordants were confirmed positive by the CMV TMA Quantitation and showed a strong correlation in value between TTime and Ct. This gives a 100% specificity if the 6 specimens are excluded from the data set 40/50 samples were positive by CMV PCR while the Roche Test tested all 50 as positive for CMV. The 10 specimens were tested by CMV TMA Quantitation and 8 were low positive, below the theoretical limit (and hence not positive with initial testing). The other 2 were also negative by the CMV TMA Quant. The 8 that were positive were well below the IU/ml given by Roche (from 1-3 logs lower). The CMV PCR assays show promising results with ability to pick up specimens in the 5-10 cp/rxn range and 100% specificity.

Example 8. CMV Oligo Screen

CMV oligomer designs in various combinations were evaluated using CMV plasmid. Designs are based on CMV TMA oligomer designs. CMV oligomers were screened in various combinations and tested. The following PPR mixes were made.

TABLE 8-1

| PPR mixes. | | | | | | |
|---|---|---|---|---|---|---|
| Name | SEQ ID NO. | Units | Stock Conc | Final Conc | ×1.25 | μL |
| Mix 1: 12, 27, 53 | | | | | | |
| primer | 11 | μM | 100.00 | 0.60 | 0.75 | 4.2 |
| primer | 27 | μM | 100.00 | 0.60 | 0.75 | 4.2 |
| probe | 53 | μM | 134.00 | 0.40 | 0.50 | 2.1 |
| primer | 83 | μM | 187.50 | 0.60 | 0.75 | 2.2 |
| primer | 84 | μM | 194.20 | 0.60 | 0.75 | 22 |
| probe | 85 | μM | 147.40 | 0.40 | 0.50 | 1.9 |
| MgCl2 | | mM | 1000.00 | 3.00 | 3.75 | 21 |
| KC1 | | mM | 2000.00 | 65.00 | 81.25 | 22.8 |
| Water | | | | | | 518.4 |
| Total: | | | | | | 560.0 |
| Mix 2: 12, 26, 53 | | | | | | |
| primer | 11 | μM | 100.00 | 0.60 | 0.75 | 4.2 |
| primer | 23 | μM | 100.00 | 0.60 | 0.75 | 4.2 |

TABLE 8-1-continued

| PPR mixes. | | | | | | |
|---|---|---|---|---|---|---|
| Name | SEQ ID NO. | Units | Stock Conc | Final Conc | ×1.25 | μL |
| probe | 53 | μM | 134.00 | 0.40 | 0.50 | 21 |
| primer | 83 | μM | 187.50 | 0.60 | 0.75 | 22 |
| primer | 84 | μM | 194.20 | 0.60 | 0.75 | 22 |
| probe | 85 | μM | 147.40 | 0.40 | 0.50 | 1.9 |
| MgCl2 | | mM | 1000.00 | 3.00 | 3.75 | 2.1 |
| KC1 | | mM | 2000.00 | 65.00 | 81.25 | 22.8 |
| Water | | | | | | 518.4 |
| Total: | | | | | | 560.0 |
| Mix 3: 12, 27, 53 | | | | | | |
| primer | 11 | μM | 100.00 | 0.60 | 0.75 | 4.2 |
| primer | 27 | μM | 100.00 | 0.60 | 0.75 | 4.2 |
| probe | 53 | μM | 146.60 | 0.40 | 0.50 | 1.9 |
| primer | 83 | μM | 187.50 | 0.60 | 0.75 | 22 |
| primer | 84 | μM | 194.20 | 0.60 | 0.75 | 2.2 |
| probe | 85 | μM | 147.40 | 0.40 | 0.50 | 1.9 |
| MgCl2 | | mM | 1000.00 | 3.00 | 3.75 | 2.1 |
| KC1 | | mM | 2000.00 | 65.00 | 81.25 | 22.8 |
| Water | | | | | | 518.5 |
| Total: | | | | | | 560.0 |
| Mix 4: 12, 26, 53 | | | | | | |
| primer | 11 | μM | 100.00 | 0.60 | 0.75 | 4.2 |
| primer | 23 | μM | 100.00 | 0.60 | 0.75 | 4.2 |
| probe | 53 | μM | 146.60 | 0.40 | 0.50 | 1.9 |
| primer | 83 | μM | 187.50 | 0.60 | 0.75 | 22 |
| primer | 84 | μM | 194.20 | 0.60 | 0.75 | 22 |
| probe | 85 | μM | 147.40 | 0.40 | 0.50 | 1.9 |
| MgCl2 | | mM | 1000.00 | 3.00 | 3.75 | 2.1 |
| KC1 | | mM | 2000.00 | 65.00 | 81.25 | 22.8 |
| Water | | | | | | 518.5 |
| Total: | | | | | | 560.0 |
| Mix 5: 13, 27, 53 | | | | | | |
| primer | 13 | μM | 100.00 | 0.60 | 0.75 | 4.2 |
| primer | 27 | μM | 100.00 | 0.60 | 0.75 | 4.2 |
| probe | 53 | μM | 134.00 | 0.40 | 0.50 | 2.1 |
| primer | 83 | μM | 187.50 | 0.60 | 0.15 | 12 |
| primer | 84 | μM | 194.20 | 0.60 | 0.75 | 12 |
| probe | 85 | μM | 147.40 | 0.40 | 0.50 | 1.9 |
| MgCl2 | | mM | 1000.00 | 3.00 | 3.75 | 21 |
| KC1 | | mM | 2000.00 | 65.00 | 81.25 | 22.8 |
| Water | | | | | | 518.4 |
| Total: | | | | | | 560.0 |
| Mix 6: 13, 26, 53 | | | | | | |
| primer | 13 | μM | 100.00 | 0.60 | 0.75 | 4.2 |
| primer | 23 | μM | 100.00 | 0.60 | 0.75 | 4.2 |
| probe | 53 | μM | 134.00 | 0.40 | 0.50 | 2.1 |
| primer | 83 | μM | 187.50 | 0.60 | 0.75 | 2.2 |
| primer | 84 | μM | 194.20 | 0.60 | 0.75 | 2.2 |
| probe | 85 | μM | 147.40 | 0.40 | 0.50 | 1.9 |
| MgCl2 | | mM | 1000.00 | 3.00 | 3.75 | 2.1 |
| KC1 | | mM | 2000.00 | 65.00 | 81.25 | 22.8 |
| Water | | | | | | 518.4 |
| Total: | | | | | | 560.0 |
| Mix 7: 13, 27, 53 | | | | | | |
| primer | 13 | μM | 100.00 | 0.60 | 0.75 | 4.2 |
| primer | 27 | μM | 100.00 | 0.60 | 0.75 | 4.2 |
| probe | 53 | μM | 146.60 | 0.40 | 0.50 | 1.9 |
| primer | 83 | μM | 117.50 | 0.60 | 0.75 | 2.2 |
| primer | 84 | μM | 194.20 | 0.60 | 0.75 | 2.2 |
| probe | 85 | μM | 147.40 | 0.40 | 0.50 | 1.9 |
| MgCl2 | | mM | 1000.00 | 3.00 | 3.75 | 2.1 |
| KC1 | | mM | 2000.00 | 65.00 | 81.25 | 22.8 |
| Water | | | | | | 518.5 |
| Total: | | | | | | 560.0 |

TABLE 8-1-continued

| PPR mixes. | | | | | | |
|---|---|---|---|---|---|---|
| Name | SEQ ID NO. | Units | Stock Conc | Final Conc | ×1.25 | μL |
| Mix 8: 13, 26, 53 | | | | | | |
| primer | 13 | μM | 100.00 | 0.60 | 0.75 | 4.2 |
| primer | 23 | μM | 100.00 | 0.60 | 0.75 | 4.2 |
| probe | 53 | μM | 146.60 | 0.40 | 0.50 | 1.9 |
| primer | 83 | μM | 117.50 | 0.60 | 0.15 | 2.2 |
| primer | 84 | μM | 194.20 | 0.60 | 0.75 | 2.2 |
| probe | 85 | μM | 147.40 | 0.40 | 0.50 | 1.9 |
| MgCl2 | | mM | 1000.00 | 3.00 | 3.75 | 2.1 |
| KC1 | | mM | 2000.00 | 65.00 | 81.25 | 22.8 |
| Water | | | | | | 518.4 |
| Total: | | | | | | 560.0 |

550 μL of PPR mix was added to 8 separate recon tubes and 250 L of oil added to the top of each. All tubes were spun down again, before loading onto the instrument.

CMV plasmid was tested at three concentrations in STM with the PPR mixes. CMV plasmid was diluted to 1000, 100, and 10 cp/rxn by doing the following:

TABLE 8-2

| CMV plasmid dilution. CMV Calibrator, Concentration Needed (Calculation) | | | | | |
|---|---|---|---|---|---|
| start conc (cp/μL) | testing amount (cp) per 5 μL rxn | cp/μL in sample tube | start vol (μL) | μL of STM | final vol (μL) |
| 10000.00 | 1000 | 27.78 | 19.2 | 6880.8 | 6900.00 |
| 27.78 | 100 | 2.78 | 620.0 | 5580.0 | 6200.00 |
| 2.78 | 10 | 0.28 | 560.0 | 5040.0 | 5600.00 |

1.34 ml was added to four tubes per each concentration. One extraction for each tube was processed with three PCR reps per extraction. A negative control was also tested and consisted of 2.9 ml of STM only. N=3 with one extraction. All samples were processed on a Panther Fusion system. Data was analyzed using a DevTool having the following parameters:

TABLE 8-3

| Channel | CrossTalk Correction | Convergence Cycle | End Cycle Cutoff | Positivity/CT Threshold |
|---|---|---|---|---|
| FAM | N/A | 10 | 75 | 1000 |
| HEX | N/A | 10 | 25 | 300 |
| ROX | N/A | 10 | 25 | 300 |
| RED647 | N/A | 10 | 25 | 300 |
| RED677 | N/A | 10 | 25 | 500 |

TABLE 8-4

| Oligo Information/Description. | | | | |
|---|---|---|---|---|
| | SEQ ID NO. | Sequence 5' → 3' | Modifications | MW without Modifications |
| **Target: CMV** | | | | |
| primer | 11 | CAGATACACTATAGCCGCCG | None | 6070.95 |
| primer | 13 | GTACAGATACACTATAGCCGCCG | None | 7017.56 |
| primer | 27 | TGTGTTCGAAATGCAACGAATACG | None | 7409.82 |
| primer | 23 | CCATGGAGCTGGAGTGTCTAAAG | None | 7128.63 |
| probe | 53 | CGTGGACTCCGCCAGTAACACGTT | 5' Fluorescein, 3' BHQ1 | 7313.72 |
| probe | 53 | CGTGGACTCCGCCAGTAACACGTT | 5' Fluorescein, 8 mdCS, 3' BHQ1 | 7313.72 |
| **Target: IC** | | | | |
| primer | 83 | ATGGTCAATTAGAGACAAAG | None | 6198.06 |
| primer | 84 | CGTTCACTATTGGTCTCTGC | None | 6049.88 |
| probe | 85 | CGGAATCACAAGTCAATCATCGCGCA | 5' Q705 and 3' BHQ2 | 7933.16 |

TABLE 8-5

Results: CMV Plasmid.

| Conc. (cp/rxn) | Channel | SEQ ID NO; combination | Reactivity | Average of Ct | StdDev of Ct | Average of RFU | StdDev of RFU | Avg T-Slope | Avg Background | Total RFU | Signal to Noise |
|---|---|---|---|---|---|---|---|---|---|---|---|
| 1000 | FAM | '11, 27, 53' | 3/3 | 30.09 | 0.21 | 25069.21 | 2256.86 | 633.01 | 9854.43 | 34923.63 | 3.54 |
| 1000 | FAM | '11, 27, 53' | 3/3 | 30.41 | 0.05 | 27973.28 | 324.94 | 627.98 | 9095.98 | 37069.27 | 4.08 |
| 1000 | FAM | '11, 23, 53' | 3/3 | 30.03 | 0.04 | 30252.97 | 1943.44 | 794.97 | 10012.41 | 40265.38 | 4.02 |
| 1000 | FAM | '11, 23, 53' | 3/3 | 29.97 | 0.17 | 39664.64 | 2622.42 | 585.72 | 11247.31 | 50911.95 | 4.53 |
| 1000 | FAM | '13, 27, 53' | 3/3 | 30.19 | 0.14 | 26713.54 | 1209.18 | 697.72 | 11103.54 | 37817.05 | 3.41 |
| 1000 | FAM | '13, 27, 53' | 3/3 | 30.31 | 0.03 | 28987.98 | 1675.63 | 685.07 | 9839.88 | 38827.85 | 3.95 |
| 1000 | FAM | '13, 23, 53' | 3/3 | 30.29 | 0.25 | 27272.45 | 3976.90 | 670.85 | 10300.46 | 37572.91 | 3.65 |
| 1000 | FAM | '13, 23, 53' | 3/3 | 30.18 | 0.11 | 33009.90 | 885.78 | 731.90 | 9857.49 | 42867.39 | 4.35 |
| 100 | FAM | '11, 27, 53' | 3/3 | 33.67 | 0.17 | 16657.24 | 2084.83 | 553.54 | 9138.22 | 25795.46 | 2.82 |
| 100 | FAM | '11, 27, 53' | 3/3 | 33.79 | 0.21 | 20694.33 | 817.48 | 653.56 | 9674.70 | 30369.53 | 3.14 |
| 100 | FAM | '11, 23, 53' | 3/3 | 33.62 | 0.21 | 26543.03 | 3749.20 | 579.83 | 10853.08 | 37396.11 | 3.45 |
| 100 | FAM | '11, 23, 53' | 3/3 | 34.20 | 0.56 | 24072.01 | 2048.45 | 589.90 | 8287.40 | 32359.41 | 3.90 |
| 100 | FAM | '13, 27, 53' | 3/3 | 34.16 | 0.29 | 19561.81 | 1104.47 | 616.86 | 11042.58 | 30604.39 | 2.77 |
| 100 | FAM | '13, 27, 53' | 3/3 | 34.00 | 0.30 | 23815.06 | 904.02 | 715.53 | 10523.13 | 34338.19 | 3.26 |
| 100 | FAM | '13, 23, 53' | 3/3 | 33.93 | 0.38 | 23276.00 | 2790.64 | 694.14 | 10085.33 | 33361.33 | 3.31 |
| 100 | FAM | '13, 23, 53' | 3/3 | 33.89 | 0.17 | 28887.54 | 913.34 | 630.49 | 10118.36 | 39005.89 | 3.85 |
| 10 | FAM | '11, 27, 53' | 3/3 | 37.80 | 0.27 | 9106.08 | 2099.18 | 582.25 | 10596.79 | 19702.87 | 1.86 |
| 10 | FAM | '11, 27, 53' | 3/3 | 37.44 | 0.36 | 10961.51 | 1985.47 | 675.63 | 9465.80 | 20427.31 | 2.16 |
| 10 | FAM | '11, 23, 53' | 3/3 | 37.37 | 1.10 | 16339.93 | 4973.83 | 670.18 | 10713.66 | 27053.59 | 2.53 |
| 10 | FAM | '11, 23, 53' | 3/3 | 37.46 | 0.18 | 16075.20 | 2246.05 | 661.92 | 9072.09 | 25147.29 | 2.77 |
| 10 | FAM | '13, 27, 53' | 3/3 | 37.23 | 0.07 | 10483.04 | 1172.91 | 681.76 | 9576.44 | 20059.49 | 2.09 |
| 10 | FAM | '13, 27, 53' | 3/3 | 37.76 | 1.00 | 9999.67 | 1920.12 | 638.08 | 9902.95 | 19902.62 | 2.01 |
| 10 | FAM | '13, 23, 53' | 3/3 | 37.85 | 104 | 14755.91 | 2546.00 | 729.71 | 11333.43 | 26089.34 | 2.30 |
| 10 | FAM | '13, 23, 53' | 3/3 | 37.90 | 0.27 | 13325.18 | 1079.75 | 627.94 | 9753.60 | 23078.78 | 2.37 |
| 1000 | RED677 | '11, 27, 53' | 3/3 | 23.21 | 0.16 | 3076.46 | 355.40 | 309.42 | 1018.65 | 4095.11 | 4.02 |
| 1000 | RED677 | '11, 27, 53' | 3/3 | 23.11 | 0.03 | 3666.06 | 120.62 | 338.99 | 1094.93 | 4760.99 | 4.35 |
| 1000 | RED677 | '11, 23, 53' | 3/3 | 23.12 | 0.09 | 3576.19 | 225.36 | 332.99 | 1141.67 | 4717.86 | 4.13 |
| 1000 | RED677 | '11, 23, 53' | 3/3 | 27.83 | 0.15 | 4563.62 | 296.47 | 298.85 | 1364.37 | 5928.49 | 4.34 |
| 1000 | RED677 | '13, 27, 53' | 3/3 | 23.05 | 0.06 | 3658.01 | 56.81 | 310.01 | 1092.85 | 4750.86 | 4.35 |
| 1000 | RED677 | '13, 27, 53' | 3/3 | 28.03 | 0.12 | 3326.36 | 237.47 | 299.58 | 1143.77 | 4470.14 | 3.91 |
| 1000 | RED677 | '13, 23, 53' | 3/3 | 28.26 | 0.26 | 2900.12 | 506.76 | 261.27 | 1014.73 | 3914.85 | 3.86 |
| 1000 | RED677 | '13, 23, 53' | 3/3 | 23.17 | 0.05 | 3221.34 | 176.36 | 322.55 | 1014.14 | 4235.49 | 4.18 |
| 100 | RED677 | '11, 27, 53' | 3/3 | 23.24 | 0.28 | 2883.30 | 635.12 | 255.71 | 959.77 | 3843.07 | 4.00 |
| 100 | RED677 | '11, 27, 53' | 3/3 | 23.16 | 0.05 | 3571.17 | 92.91 | 325.74 | 1107.05 | 4678.22 | 4.23 |
| 100 | RED677 | '11, 23, 53' | 3/3 | 23.07 | 0.23 | 3843.87 | 450.34 | 292.24 | 1254.59 | 5098.46 | 4.06 |
| 100 | RED677 | '11, 23, 53' | 3/3 | 23.13 | 0.15 | 3864.41 | 286.52 | 293.64 | 1120.43 | 4984.84 | 4.45 |
| 100 | RED677 | '13, 27, 53' | 3/3 | 28.09 | 0.09 | 3531.51 | 230.88 | 296.16 | 1054.39 | 4585.90 | 4.35 |
| 100 | RED677 | '13, 27, 53' | 3/3 | 28.08 | 0.18 | 3460.07 | 509.56 | 291.80 | 1209.52 | 4669.59 | 3.86 |
| 100 | RED677 | '13, 23, 53' | 3/3 | 23.24 | 0.24 | 2948.60 | 578.59 | 260.43 | 1037.16 | 3985.75 | 3.84 |
| 100 | RED677 | '13, 23, 53' | 3/3 | 28.20 | 0.01 | 3117.20 | 103.56 | 313.46 | 992.78 | 4109.98 | 4.14 |
| 10 | RED677 | '11, 27, 53' | 3/3 | 23.10 | 0.18 | 3356.44 | 459.90 | 283.48 | 1101.33 | 4457.78 | 4.05 |
| 10 | RED677 | '11, 27, 53' | 3/3 | 28.05 | 0.02 | 3836.75 | 75.17 | 352.99 | 1252.00 | 5088.75 | 4.06 |
| 10 | RED677 | '11, 23, 53' | 3/3 | 28.39 | 0.25 | 3499.82 | 490.32 | 293.33 | 1178.50 | 4678.31 | 3.97 |
| 10 | RED677 | '11, 23, 53' | 3/3 | 27.96 | 0.05 | 4007.96 | 152.39 | 276.78 | 1170.84 | 5178.80 | 4.42 |
| 10 | RED677 | '13, 27, 53' | 3/3 | 28.22 | 0.25 | 3208.92 | 570.21 | 266.68 | 930.47 | 4189.45 | 4.27 |
| 10 | RED677 | '13, 27, 53' | 3/3 | 28.31 | 022 | 3086.13 | 539.07 | 301.27 | 1115.99 | 4202.12 | 3.77 |

TABLE 8-5-continued

| Results: CMV Plasmid. | | | | | | | | | | | |
|---|---|---|---|---|---|---|---|---|---|---|---|
| Conc. (cp/rxn) | Channel | SEQ ID NO; combination | Reactivity | Average of Ct | StdDev of Ct | Average of RFU | StdDev of RFU | Avg T-Slope | Avg Background | Total RFU | Signal to Noise |
| 10 | RED677 | '13, 23, 53' | 3/3 | 28.25 | 0.26 | 3096.73 | 378.26 | 264.03 | 1093.52 | 4190.25 | 3.83 |
| 10 | RED677 | '13, 23, 53' | 3/3 | 28.06 | 0.16 | 3400.50 | 527.82 | 296.92 | 1141.44 | 4541.94 | 3.98 |

Conclusion: Results show 100% detection down to 10 cp/rxn for all oligo sets. The best combo includes SEQ ID NO: 11 and SEQ ID NO: 23. Either probe shows good results, with SEQ ID NO: 53 showing much higher RFU at 1000 cp/rxn and higher signal to noise, and SEQ ID NO: 53 showing higher RFU at 100 and 10 cp/rxn. SEQ ID NO: 13, SEQ ID NO: 23, and SEQ ID NO: 53 also show good results at all concentrations, but starts to fall behind at 10 cp/rxn when compared to the SEQ ID NO: 11/SEQ ID NO: 23 combos.

Example 9. CMV Quantitation

The CMV Quantitation assay is an in vitro nucleic acid amplification test for the quantitation of cytomegalovirus (CMV) DNA and/or RNA in samples, including, but not limited to biological sample such as human plasma. The CMV Quantitation assay can be combined with an automated detection system. The CMV Quantitation assay can be used to aid in the management of solid organ transplant recipients. In patients receiving anti-CMV therapy, serial DNA measurements can be used to assess viral response to treatment.

In some embodiments, the CMV Quantitation assay is a transcription mediated amplification test with real time detection. This assay is used for detection and/or quantification of CMV in samples and can be combined with a detection system. The detection system can be an instrument that provides automation for specimen processing, amplification, detection, data reduction for quantification and amplicon inactivation.

Reagents: Controls and calibrators are provided, optionally in separate boxes. The reagents, calibrators, and controls provided in each assay kit box are detailed in Table 9A below. Each kit contains three lyophilized materials, Amplification Reagent, Promoter Reagent and Enzyme Reagent. These are reconstituted by the user using reconstitution reagents which are specific for each lyophilized reagent. Each kit includes Target Capture Reagent (TCR) and Target Enhancer Reagent (TER) which are provided in liquid format while the remaining reagents are lyophilized. Calibrator and additional controls can be separately provided.

TABLE 9A

| Materials in the CMV Quantitation Assay Kit | | |
|---|---|---|
| Box | Storage Condition | Reagents and Materials |
| Assay Specific Reagents | 2-8° C. | Target Capture Reagent<br>Target Enhancer Reagent<br>Amplification Reagent (lyophilized pellet)<br>Amplification Reagent Reconstitution Solution<br>Enzyme Reagent (lyophilized pellet)<br>Enzyme Reagent Reconstitution Solution<br>Promoter Reagent (lyophilized pellet)<br>Promoter Reagent Reconstitution Solution |
| Calibrator | Store Frozen −20° C. | Positive Calibrator |
| Controls | Store Frozen −20° C. | Negative Control<br>Low Positive Control<br>High Positive control |

Exemplary reagents include the following.

"Sample Transport Medium" or "STM" is a phosphate-buffered solution (pH 6.7) that includes EDTA, EGTA, and lithium lauryl sulfate (LLS).

"Target Capture Reagent" or "TCR" is a HEPES-buffered solution (pH 6.4) that includes lithium chloride and EDTA, together with 250 μg/ml of magnetic particles (1 micron SERA-MAG™ MG-CM particles, Seradyn, Inc. Indianapolis, IN) with $(dT)_{14}$ oligonucleotides covalently bound thereto. In some embodiments, TCR contains one or more TCOs, and/or one or more T7 primers, and optionally one or more displacer oligomers.

"Target Capture Wash Solution" or "TC Wash Solution" is a HEPES-buffered solution (pH 7.5) that includes sodium chloride, EDTA, 0.3% (v/v) absolute ethanol, 0.02% (w/v) methyl paraben, 0.01% (w/v) propyl paraben, and 0.1% (w/v) sodium lauryl sulfate.

"Amplification Reagent" or "AR" is a HEPES-buffered solution (pH 7.7) that includes magnesium chloride, potassium chloride, four deoxyribonucleotide triphosphates (dATP, dCTP, dGTP, and dTTP), four ribonucleotide triphosphates (rATP, rCTP, rGTP, and rUTP). Primers and/or probes may be added to the reaction mixture in the amplification reagent, or may be added separate from the reagent (primerless amplification reagent).

"Enzyme Reagents" or "ER", as used in amplification or pre-amplification reaction mixtures, are HEPES-buffered solutions (pH 7.0) that include MMLV reverse transcriptase (RT), T7 RNA polymerase, salts and cofactors.

"Target Enhancer Reagent" (TER) solution contains 1.6 N LiOH.

Procedure: The CMV Quantitation Assay uses real-time monitoring of Transcription-Mediated Amplification (TMA) to quantitate CMV virus. The assay targets the UL 56 gene of CMV. The amount of virus in the sample is determined by comparing the signal to that generated from a known concentration of virus DNA (calibrator). In addition, controls are run every 24 hours to ensure the validity of the tests. The assay is performed using a detection system using three basic processing steps;

1) Target capture where the virus is lysed, hybridized to magnetic particles, and separated from the specimen components.
2) Amplification of the target using TMA with concurrent collection of fluorescent signal.

3) Processing of the signal to generate a quantitative result for each sample.

During target capture, viral DNA is isolated from specimens by treatment with a detergent to solubilize the viral envelope, denature proteins and release viral genomic DNA. Capture oligonucleotides hybridize to highly conserved regions of CMV DNA, if present in the test specimen. The hybridized target binds to magnetic particles that are subsequently separated from the specimen using a magnetic field.

Target amplification occurs isothermally via transcription-mediated amplification. Two enzymes, T7 RNA polymerase and a reverse transcriptase are used to generate RNA from captured DNA exponentially via cycles of forward and reverse transcription.

Detection is achieved using single-stranded nucleic acid torches that are present during target amplification and hybridize to the amplicon in real time. Each torch has a fluorophore and a quencher. When the torch is not hybridized to the amplicon the quencher is in close proximity of the fluorophore and suppresses fluorescence. Amplicon-torch binding results in the separation of the quencher from the fluorophore; which allows fluorophore excitation in response to light stimulus and signal emission at a specific wavelength.

Table 9B shows processing steps that can be used with a CMV Quantitation Assay.

TABLE 9B

| CMV Quantitation Assay Process | |
|---|---|
| | CMV Quantitation |
| Sample, TER and TCR Addition | Add 60 μL of TER to each reaction tube.<br>Add 500 μL of assay calibrator, controls and/or specimens to individual reaction tubes.<br>Add 400 μL of TCR to each reaction tube.<br>Mix TCR, TER and sample. |
| Annealing Step | Incubate at 43.7° C. for 4.1 minutes, then at 64° C. for 28.5 minutes.<br>Incubate at 43.7° C. for 5.5 minutes, then at 18° C. for 9.4 minutes. |
| Magnetic Wash Steps | Dwell for 9.8 minutes at room temperature.<br>Apply a magnetic field, and dwell for 2 minutes.<br>Aspirate liquid from each tube.<br>Remove magnetic field. Add 1 mL of Wash Solution to each tube.<br>Mix.<br>Apply magnetic field and dwell for 2 minutes.<br>Aspirate liquid from each tube.<br>Remove magnetic field. Add 1 mL of Wash Solution.<br>Add 100 μL of Oil Reagent.<br>Mix.<br>Apply magnetic field and dwell for 2 minutes.<br>Aspirate liquid from each tube. |
| Oil and Amplification Reagent Addition | Add 100 μL of Oil Reagent.<br>Warm to 45° C. Add 50 μL of reconstituted Amplification Reagent to each reaction tube.<br>Mix. |
| Primer Anneal Step | Incubate at 43.7° C. for about 25 minutes. |
| Amplification and Real-Time Detection | Transfer to 45° C., add 25 μL reconstituted Enzyme Reagent to each reaction tube. Mix.<br>Incubate at 42.7° C. for 5.4 minutes.<br>Transfer to 45° C. and add 25 μL Promoter Reagent to each reaction tube.<br>Mix.<br>Incubate at 42.7° C. for 53.4 minutes. Fluorescent signal is read in real time during amplification. |
| Deactivation Step | Deactivate with a 2000 μL mixture of Deactivation Fluid and bleach. |

Assay Processing: Real-time detection and quantitation was performed using fluorometers.

The Target Capture Reagent (TCR), optionally in combination with Target Enhancer Reagent (TER), lyses the CMV and facilitates capture of the released CMV DNA onto magnetic particles. The virus is lysed using lithium lauryl sulfate that is present in TCR. The CMV DNA released by this process is captured onto magnetic particles using CMV-specific oligonucleotides, or "capture oligos" (also termed "target capture oligos"). The TCR may also contain an internal calibrator/internal control (IC) which is a sequence of DNA unrelated to CMV. The IC is processed in conjunction with the target in the same tube and acts as both an internal control and an internal calibrator for the test.

Step 1. 60 μL of TER is added to each tube followed by 500 μL of sample. 400 μL of TCR was added to each reaction tube. The TCR buffer contains lithium lauryl sulfate at 10 g/100 mL to lyse the virus, magnetic particles for target capture, and IC- and CMV-specific oligo nucleotides for amplification. The fluid is mixed to ensure the mixture is homogeneous.

Step 2. The sample is optionally incubated in the Transition Incubator at 43.7° C. to preheat the sample prior to transfer to the High Temp Incubator which is at 64° C.

Step 3. The sample is then transferred to the High Temp Incubator set to 64° C. During the incubation at 64° C., the CMV is disrupted and genomic DNA is released. Present in the TCR are several oligo nucleotides. The first of these is the T7 promoter primer that is complementary to the target and incorporates the T7 promoter region. Due to the length of this oligonucleotide, it is less affected by mismatches in the target sequence thereby improving equal genotype detection. There is also a displacer primer that helps to open up the double stranded DNA to enable the T7 primer to bind to the target.

Step 4. The sample is moved back to the Transition Incubator to start the cool down process. Present in the TCR are capture oligonucleotides and magnetic beads conjugated with poly-T oligo nucleotides. The capture oligonucleotides have sequences complementary to the target that enables them to capture the target and 30-base polyA tails that enable them to hybridize to the poly-T oligonucleotides on the magnetic beads. During the initial cool down step and continuing in step 5, the target and IC are captured onto the magnetic particles.

Step 5. The sample is cooled in the Chiller ramp (17° C. to 19° C.) leading to a tighter binding between the CMV and IC targets with the magnetic beads.

Step 6. The sample is transferred to the Magnetic Parking Station. Here sample is subjected to magnets which pull the magnetic particles to the sides of the tube prior to entering the magnetic wash station.

Step 7. The sample is then moved to a magnetic wash station where potential interfering substances are removed from the reaction by washing the magnetic particles. A magnet temporarily moves the magnetic particles to the side of the tube containing the sample and the liquid is removed. Wash buffer is added and the process is repeated to ensure potentially interfering substance have been removed. The sample containing the purified magnetic beads is then moved to the Amp load station for reagent addition.

Amplification and Signal Detection: The amplification creates many copies of a target so it can be more easily detected. This is achieved using TMA technology (patent incorporated by reference). Amplification Reagent, Promoter Reagent and Enzyme Reagent were used to initiate and sustain amplification and to detect the product in real time. These reagents can be lyophilized reagents which are reconstituted prior to use. The reconstituted Amplification Reagent is a buffered solution and contains a non-T7 oligonucleotides specific for CMV and IC. There is also a blocked helper oligomer that helps the non-T7 oligonucleotides to bind to target. It also contains the raw materials necessary to build amplicon.

The CMV Quantitation Assay uses two phases of amplification, linear and exponential. The second, exponential, phase of amplification is achieved using the Promoter Reagent. The reconstituted Promoter Reagent is a buffered solution containing T7 oligonucleotides for the CMV and IC targets. The Promoter Reagent also contains the materials necessary to build copies of the RNA amplicon along with target-specific torches that detect amplified CMV or IC in real time. The reconstituted Enzyme Reagent is a buffered solution and contains two enzymes that initiate and sustain amplification of both the CMV and IC targets.

Amplification: Initially, promoter primer binds to the sample target DNA or RNA. A displacing primer may also be used to improve promoter primer binding. Reverse transcriptase then extends the promoter primer or the promoter primer and the displacing primer to create single strand DNA. Single strand DNA having the promoter primer is created. The forward primer then binds the ssDNA and RNA polymerase extends the strand. A single RNA strand can serve as template for multiple copies of RNA.

Step 8. Amplification reagent (50 μL/test) is added to the sample and mixed in the Amp Load station.

Step 9. The sample is moved to the Transition Incubator at 43.7° C. to increase the temperature of the sample.

Step 10. The sample is moved back to the Amp Load station where Enzyme reagent (25 μL/test) is added.

Step 11. The sample is moved to the Amplification Incubator set at 42.7° C. The sample remains in this incubator for five minutes during which the first rounds of amplification are initiated. The T7 initiation primer is complementary to the CMV target and also contains a promoter sequence for the T7 RNA polymerase. The Reverse Transcriptase present in the Enzyme reagents binds to the T7 initiation primer-target complex and initiates generation of complementary DNA from the CMV target. The Reverse Transcriptase also initiates a displacement reaction using displacer oligomer to generate single strand DNA from the CMV target. A similar reaction occurs at the same time for the IC. This single strand DNA now incorporates the T7 promoter region. The Amplification Reagent also contains non-T7 primers which bind to the complementary DNA (cDNA) and start the creation of double stranded DNA. This is then used by the RNA polymerase from the Enzyme reagent to make multiple copies of RNA. This RNA is then converted to single stranded DNA amplicon by Reverse Transcriptase using non-T7 primers. This phase is known as the Linear Amplification or enrichment phase.

Step 12. After the 5-minute Linear Amplification Phase the sample is moved back to the Amp Load Station, where the Promoter Reagent is added and mixed.

Step 13. The sample is moved back to the Amplification Incubator for further rounds of amplification. The Promoter Reagent (25 μL/test) contains additional CMV and IC T7 primers. The addition of the Promoter reagent initiates and sustains additional rounds of exponential amplification for the CMV and IC targets. The Amplification Incubator also incorporates fluorometers where the fluorescent signals generated by the amplification are measured. The addition of the second T7 promoter primer initiates generation of the complementary strand of DNA to the single stranded cDNA created in the earlier steps. This is then used by the RNA polymerase to make multiple copies of RNA. The internal control creates cDNA from the RNA target and the double stranded DNA using similar mechanisms to that for CMV.

Also present in the Promoter Reagent are torches as described above.

Signal and Results Processing: Signals for both the CMV target and the IC are processed by first performing baseline subtraction. Baseline subtraction estimates the baseline for each curve then removes that level of fluorescence from each data point. The result is that the baseline of each curve starts from the same level.

The data are then scaled (normalized) so that the maximum fluorescence for all samples is the same. The resultant curves are then analyzed by standard curve fitting algorithms.

After baseline subtraction and normalization has been completed, the TTime for each curve can be calculated. The TTime is the time (on the x axis) that the normalized fluorescent signal (y axis) emerges from the background signal. This is set by a predetermined cutoff. The TTime for each reaction is calculated for both the target and the corresponding IC curve.

To correct for individual variations, the CMV TTime is divided by the IC TTime to generate a "ratio". The CMV TTime is inversely proportional to the CMV concentration in the initial specimen. The CMV curves generated by samples varying from 100 IU/mL to 1E8 IU/mL are separated into distinct curves. The IC TTime is relatively constant as the IC target concentration in each reaction is constant. Slight competition between the CMV and IC amplification systems means the IC TTime increases slightly, but in a predictable manner. The Ratio of the CMV and IC TTimes then is used to generate a calibration curve, using calibrators of known CMV concentration and plotting TTime Ratio against target concentration. Once a calibration curve has been established, the concentration of CMV in an unknown sample can be calculated by comparing the ratio obtained to the calibration curve.

Stored Calibration Curve. The calibration curve is linear with a negative slope for the assay. This calibration curve can be generated for each reagent lot. The mathematical equation for the calibration curve is established and the point at which the line would cross the x-axis is determined by extrapolation.

Before generating results, each reagent kit is calibrated running three replicates of a calibrator. There are two positive controls, one at a low concentration and the other at a higher concentration and a negative control ae used. The calibrator contains synthetic DNA of CMV in a buffered solution at a pre-defined concentration. Due to the linear nature of the calibration curve, a reagent kit specific calibration curve is generated using a combination of the user-run calibrator and the calibration curve x-intercept.

Results Reporting: Results can be calculated using the information generated from the calibrator and controls samples.

Example 10. Multi-Phase (BiPhasic) Amplification Detection

"Sample Transport Medium" or "STM" is a phosphate-buffered solution (pH 6.7) that included EDTA, EGTA, and lithium lauryl sulfate (LLS).

"Target Capture Reagent" or "TCR" is a HEPES-buffered solution (pH 6.4) that includes lithium chloride and EDTA, together with 125 μg/ml of magnetic particles (1 micron SERA-MAG™ MG-CM particles, Seradyn, Inc. Indianapolis, IN) with (dT)14 oligonucleotides covalently bound thereto. TCR contains multiple oligos that may include one or more TCOs, one or more T7 primers and one or more displacers. IN some embodiments, the TCR contains one or more displacer oligomers.

"Target Capture Wash Solution" or "TC Wash Solution" is a HEPES-buffered solution (pH 7-8, pH 7.5±5, or pH 7.5) that included sodium chloride, EDTA, 0.3% (v/v) absolute ethanol, 0.02% (w/v) methyl paraben, 0.01% (w/v) propyl paraben, and 0.1% (w/v) sodium lauryl sulfate.

"Amplification Reagent" or "AR" is a Tris-buffered solution (pH 7-8, pH 7.5±5, or pH 7.0, pH 7.1, pH 7.2, pH 7.3, pH 7.4, pH7.5, pH 76, pH 7.7, pH 7.9, or pH 8) that included magnesium chloride, potassium chloride, four deoxyribonucleotide triphosphates (dATP, dCTP, dGTP, and dTTP), four ribonucleotide triphosphates (NTPs: ATP, CTP, GTP, and UTP). One or more primers, helper oligomers, displacer oligomers and or probe oligomers may be added to the reaction mixture through the amplification reagent. In some embodiments, the one or more primers, helper oligomers, displacer oligomers and or probe oligomers may be added to the reaction mixture separately from the reagent. In some embodiments, for a first phase amplification reaction, the Amplification Reagent may contain one or more non-promoter primers and one or more helper oligomers. In some embodiments, for a second phase amplification reaction, the Amplification Reagent may contain one or more promoter primers, one or more displacer oligomers, and one or more probe oligomers.

"Promoter Reagent" or PR is a Tris buffered solution that included magnesium chloride, potassium chloride, four deoxyribonucleotide triphosphates (dATP, dCTP, dGTP, and dTTP), four ribonucleotide triphosphates (NTPs: ATP, CTP, GTP, and UTP). Some of the primers, helpers and probes may be added to the reaction mixture through the promoter reagent.

"Enzyme Reagents" or "ENZ", as used in amplification or pre-amplification reaction mixtures, are HEPES-buffered solutions (pH 6.5-8, pH 7.0±5, or pH 6.5, pH 6.6, pH 6.7, pH 6.8, pH 6.9, pH 7.0, pH 7.1, pH 7.2, pH 7.3, pH 7.4, pH7.5, pH 76, pH 7.7, pH 7.9, or pH 8) that include MMLV reverse transcriptase (RT), T7 RNA polymerase, salts and cofactors.

"Target Enhancer Reagent" (TER) is an alkaline solution containing of 1.68M LiOH lithium hydroxide.

A T7 primer is hybridized to the target sequence during target capture, followed by removal of excess T7 primer during a wash step T7 primer prior to a first amplification reaction. In some embodiments, a TCO is hybridized to the target sequence during target capture. In some embodiments, a displacer oligomer is hybridized to the target sequence during target capture. Excess TCO and/or displacer oligomer may also be removed during a wash step prior to a first amplification reaction.

During the first amplification phase (AMP1), oligos including NT7 primers and optionally helpers are introduced along with all of the requisite amplification, and enzyme reagents, with the exception of additional T7 primer. In the presence of reverse transcriptase, the T7 primer hybridized to the captured target is extended, creating a cDNA copy. The NT7 primer subsequently hybridizes to the cDNA and is extended, filling in the promoter region of the T7 primer and creating an active, double-stranded DNA template. T7 polymerase then produces multiple RNA transcripts from the template. The NT7 primer subsequently hybridized to the RNA transcripts and is extended, producing promoter-less cDNA copies of the target RNA template. The RNA strands are degraded by RNase activity of the reverse transcriptase. Because no free T7 primer is available in the phase 1 amplification mixture, the reaction does not proceed further. The second phase is started with the addition of extra oligos which may include T7 primers, non T7 primers, and optionally helpers and detection oligonucleotides, thus initiating exponential amplification and detection of the cDNA pool produced in phase 1.

For multiplex amplification and detection, one or more of each of the TCO, T7 primer, NT7 primer, Torch oligonucleotides and optionally displacers and helpers are used. The oligonucleotides may amplify one or more different sequence in the same target nucleic acid, may amplify sequences in different target nucleic acids, or a combination thereof. The different target nucleic acids may be from the same or different organisms.

A Exemplary Experimental Protocol 1:

Plate Setup:

In some embodiments, four different plates are set up for use on two automated KingFisher devices.

1. Plate 1 (TCR plate) contains the sample. Target Capture Reagent (e.g., 100 μL) is added to this plate. The TCO and T7 primer, and optionally displacer oligomer hybridize to target nucleic acid (e.g., 400 μL sample). The TCO:target nucleic acid:T7 primer:(optional displacer oligomer) (pre-amplification hybrid) are captured using a magnetic bead (capture probe on solid support) using a magnet. For single phase TMA, T7 primer may be absent from the TCR mixture. In some embodiments, sample is added to TER followed by addition of TCR containing TCO and, for biphasic amplification, T7 primer. In some embodiments TER is added to the sample followed by addition of TCR containing TCO and, for biphasic amplification, T7 primer. In some embodiments TER may be added to a mixture of TCR and sample. The mixture of these reagents may be incubated at a higher temperature for a time duration so that TCO, T7 primer and optionally displacer oligomer hybridize to target nucleic acid in the sample. The TCO is also hybridized to the magnetic beads. The target nucleic acid with the hybridized TCO, T7 primer, optional displacer oligomer (pre-amplification hybrid) is captured by using a magnet to separate the magnetic beads. The mixture of sample and TCR is then removed from the tube and beads are washed twice with Aptima wash buffer.

2. Plate 2 is a deep-well plate and holds 200-500 μL/well APTIMA wash buffer. The Aptima wash buffer contains detergent and alcohol used to wash the captured target (pre-amplification hybrid).
3. Plate 3 contains 200-500 μL/well APTIMA wash buffer and is used to provide a second wash of the captured target (pre-amplification hybrid).
4. Plate 4 contains 50 μL/well AMP or AMP1 reagent. In some embodiments, the AMP or AMP1 reagents contain buffer, salt, dNTPs, NTPs and one or more NT7 primers, and optionally and/or more or more helper oligomers.

Target Capture and isolation: In some embodiments a sample is first contacted with a Target Enhancer Reagent. For BiPhasic TMA, TCO(s), T7 primer(s), and optionally displacer oligomers, are added to a sample containing or suspected of containing the target nucleic acid. For single phase TMA, TCO(s) are added to a sample containing or suspected of containing the target nucleic acid. In some embodiments, if present, T7 primer is added at a ratio of approximately 1 T7 primer to 1 target nucleic acid. TCO, T7 primer and displacer oligomers are incubated with the target nucleic acid for a period of time to allow hybridization of these oligomers to the target nucleic acid to form a pre-amplification hybrid. The pre-amplification hybrid is then captured and purified, removing excess or non-hybridized oligomers. The pre-amplification hybrid is then isolated using magnetic particles having a binding partner, such as a poly(dT), for the TCO.

1. Plate 1 (TCR plate) is placed into a heat block and heated to 62° C. for 20-30 min. followed by incubation at lower temperatures (e.g., 23° C.) for 20 min-2 h. In some embodiments, the TCR plate is covered with a 65° C. lid to prevent condensation from forming on the tops of the wells. The captured pre-amplification hybrid is then transferred to Plate 2.
2. After the first wash (about 10 min), a deep well comb/magnet cover is added to the Plate 2 to capture the pre-amplification hybrid. The captured pre-amplification hybrid is transferred to Plate 3.
3. After the second wash, a small comb (magnet cover) is added to Plate 3 to capture the pre-amplification hybrid. The washed pre-amplification hybrid is captured and transferred to Plate 4. The 4th plate is transferred to a thermal cycler for real-time isothermal amplification and detection.

Biphasic Transcription Mediated Amplification and Real Time Detection.

First Phase Amplification: AMP reagent containing NT7 primer(s), enzymes, dNTPs, NTPs, and optionally one or more helper oligomer(s) (AMP1 mixture) to the purified target nucleic acid containing the pre-amplification hybrid. The mixture is incubated for a period of time to allow formation of a first amplification product.

1. Incubate AMP1 plate, containing NT7 primer, optionally helper oligomers and purified target nucleic acid with hybridized T7 primer, at about 42-44° C. for 5-15 minutes.
2. Add 25 μL of ENZ mix, containing Reverse transcriptase, T7 RNA polymerase, seal and mix; incubate 5 minutes at about 42-44° C.

Second Phase Amplification: Promoter reagent (AMP2) containing T7 primer, and optionally a probe oligomer, such as a Torch, is added to the first amplification product and incubate for a period of time to allow formation of a second amplification product. In some embodiments, one or more helper oligomer(s) and more non T7 primers are added during the second phase amplification.

3. Add 25 μL AMP2 (also termed PR) mixture to each well, seal, and mix. In some embodiments, the AMP2 mixture contains buffer, salt, surfactant, dNTPs, NTPs, one or more T7 primers, Torch probe(s) and optionally more non T7 primers and/or helper oligomer(s).
4. Run reaction program: 120 cycles of 30 seconds at 42-43° C. with label detection (collection) at the end of each cycle.

Detection: Amplification of the target nucleic acid sequence is detected in real time by recording fluorescent signal from the detection oligonucleotide at regular intervals.

B. Exemplary Experimental Protocol 2:

Target Capture and isolation: In some embodiments a sample is first contacted with a Target Enhancer Reagent. For BiPhasic TMA, TCO(s), T7 primer(s) and optionally displacer oligomers are added to a sample containing or suspected of containing the target nucleic acid. For single phase TMA, TCO(s) are added to a sample containing or suspected of containing the target nucleic acid. TCO, T7 primer. and displacer oligomers are incubated with the target nucleic acid for a period of time to allow hybridization of these oligos to the target nucleic acid to form a pre-amplification hybrid. The pre-amplification hybrid is then captured and purified, removing excess or non-hybridized oligos. The pre-amplification hybrid is then isolated using magnetic particles having a binding partner, such as a poly(dT), for the TCO.

The mixture of sample, TCR and optionally TER is heated to 60-65° C. for 20-30 minutes, followed by incubation at lower temperature for 20 min-2 h. The preamplification hybrid is captured using magnets to separate the magnetic beads to which they are hybridized. The mixture of sample and reagents are removed from the tube. The magnetic beads are washed 1-2 times by adding wash buffer to the tube, mixing and then incubating it with magnets to separate the magnetic beads. After the beads are captured, wash buffer is removed from each tube.

Biphasic Transcription Mediated Amplification and Real Time Detection.

First Phase Amplification: Add Amp reagent containing NT7 primer(s), enzymes, dNTPs, NTPs, and optionally one or more helper oligomer(s) (AMP1 mixture) to the purified target nucleic acid containing the pre-amplification hybrid. The mixture is incubated for a period of time to allow formation of a first amplification product.

a. Incubate AMP1 mixture, containing NT7 primer, optionally helper oligomers and purified target nucleic acid (pre-amplification hybrid), at about 42-44° C. for 5-15 minutes.

b. Add 25 μL of ENZ mix, containing Reverse transcriptase, T7 RNA polymerase, mix, and incubate 5 minutes at about 42-44° C.

Second Phase Amplification: Add promoter reagent containing T7 primer, and probe oligomer, such as a Torch, to the first amplification product and incubate it for a period of time to allow formation of a second amplification product. In some embodiments, one or more helper oligomer(s) and more non T7 primers are added during the second phase amplification.

a. Add 25 μL AMP2 (alter termed PR) mixture to each tube, and mixed. In some embodiments, the AMP2 mixture contains buffer, salt, surfactant, dNTPs, NTPs, one or more T7 primers, Torch probe(s) and optionally more non T7 primers and/or helper oligomer(s).

Run reaction program: Incubate at 42-43° C. for 30-60 minutes with label detection (collection) at intervals of approximately 30 seconds.

Detection: Amplification of the target nucleic acid sequence is detected in real time by recording fluorescent signal from the detection oligonucleotide at regular intervals.

Example 11. Real Time BiPhasic TMA CMV Assay from Plasma Samples

Target capture was accomplished using TCOs to either the UL56 gene of CMV (SEQ ID NOs: 42 and 44). Two TCRs (Target Capture Mixtures) formulations, A (containing 679 mM LiOH) and B (453 mM LiOH), were added to plasmid and plasma samples. For some reactions, 100 μL or 200 μL Target Enhancer Reagent (TER) was added to the samples during the target capture phase. In some embodiments, the amount of TER used is 25-200 pIL. In some embodiments, the amount of TER used is 30, 35, 40, 45, 50, 55, 60, 65, 70, 75, 80, 85, 90, 95, 100, 125, 150, 175, or 200 μL. In some embodiments, the amount of LiOH in the target capture stage is 50-350 mM. In some embodiments, the amount of LiOH in the target capture stage is about 50 mM, about 75 mM, about 100 mM, about 125 mM, about 150 mM, about 175 mM, about 200 mM, about 225 mM, about 250 mM, about 275 mM, about 300 mM, about 325 mM, or about 350 mM.

TCO(s) were added to 1×TCR buffer (400 μL/reaction). In some samples, internal control target nucleic acid was also added. For BiPhasic TMA reactions, the indicated amount of T7 primers were added.

For single phase TMA, T7 primer, NT7 primer, and torch oligo were added to the AMP buffer to form the AMP reagent and 75 μL AMP reagent was added to each sample.

For BiPhasic TMA, NT7 oligo was added to AMP buffer to form an AMP1 reagent (AR) and T7 oligo and torch oligo were added to AMP buffer to from an AMP2 (PR) reagent. Following target capture, 50 μL AMP1 reagent was added to each sample.

For single phase TMA, 25 μL ENZ was added for each test and the samples mixed at 1400 RPMs for 1 minute. The reaction was incubated at 43° C. for 10 minutes.

For BiPhasic TMA, 25 μL ENZ was added to each test and the samples mixed at 1400 RPMs for 1 minute. The AMP1 reaction was incubated at 43° C. for 5 minutes. 25 μL of AMP2 was then added to each sample and the plate was mixed at 1400 RPMs for 1 minute. The samples were then incubated at 43° C., with fluorescence measured in real time.

Each of the experiments included control reactions containing the internal control oligomers listed in Table 11-3.

TABLE 11-1

| CMV TMA oligonucleotides | | |
|---|---|---|
| Type | SEQ ID NO. | Sequence (5' → 3') |
| TCO | 42 | GTGGTGGCGCAGAATCGTACGCAGAGTTCGTTTAAAAAAAAAA AAAAAAAAAAAAAAAAAAAA |
| TCO | 44 | GTCAGTCGGCATAGCGAGCGGCCTTTAAAAAAAAAAAAAAAAA AAAAAAAAAAAAA |
| T7 | 46 | AATTTAATACGACTCACTATAGGGAGAGCAACGAATACGCCATG GAGCTGGAGTGTCTAAAG |
| nT7 | 19 | GGTACAGATACACTATAGCCGCCGCGTTT |
| Torch | 22 | GAACGGCGUGGACUCCGCCAGUAACACGUUCGCGUUC |
| Torch | 20 | GGACUCCGCCAGUAACACGUUCGGAUCGCAGUACAGUCC |

TABLE 11-2

| CMV TMA oligonucleotides: target hybridizing sequences | | |
|---|---|---|
| Type | SEQ ID NO. | Sequence (5' → 3') |
| TCO | 43 | GTGGTGGCGCAGAATCGTACGCAGAGTTCG |
| TCO | 45 | GTCAGTCGGCATAGCGAGCGGCC |
| T7 | 47 | GCAACGAATACGCCATGGAGCTGGAGTGTCTAAAG |
| Torch | 26 | GAACGGCGUGGACUCCGCCAGUAACACGUUCG |
| Torch | 21 | GGACUCCGCCAGUAACACGUUCGGAUCGCAGUAC |

TABLE 11-3

| Internal Control oligonucleotides | | |
|---|---|---|
| Type | SEQ ID NO. | Sequence (5' → 3') |
| TCO | 48 | CGUUCACUAUUGGUCUCUGCAUUCTTTAAAAAAAAAAAAA AAAAAAAAAAAAAAAAA |
| TCO | 49 | AAAAAAAAAAAAAAAAAAAAAAAAAAAAAATTTACCGTCGT TAAAGTGGTCACG |
| T7 | 50 | aatttaatacgactcactatagggagaGATGATTGACTTGTGATTCCG C |
| nT7 | 63 | GATTATATAGGACGACAAG |
| Torch | 72 | GCAUGGUGCGAAUUGGGACAUGC |

TABLE 11-4

| Oligo preparation | | | |
|---|---|---|---|
| SEQ ID NO. | Stock Conc. (pmol/μL) | Rxn Conc. (pmol/μL) | Volume (μL) |
| 44 | 76.7 | 0.03 | 9.39 |
| 42 | 72 | 0.03 | 10.00 |
| 46 | 61.2 | 0.03 | 11.76 |
| | | Total TCR Vol. | 24000 |
| | 100,000 cp/μL | 300 cp/μL | 72.00 |
| 19 | 141 | 0.1 | 3.97 |
| | | Total AMP Vol. | 5600 |
| 46 | 61.2 | 0.12 | 5.49 |
| 20 | 77.5 | 0.1 | 3.61 |
| | | Total AMP Vol. | 2800 |

TABLE 11-4-continued

| Oligo preparation | | | |
|---|---|---|---|
| SEQ ID NO. | Stock Conc. (pmol/μL) | Rxn Conc. (pmol/μL) | Volume (μL) |
| 48 | 100 | 0.03 | 7.2 |
| 49 | 63 | 0.03 | 11.43 |
| 50 | 100 | 0.03 | 7.2 |
| | | Total TCR Vol. | 24000 |
| 63 | 100 | 0.08 | 4.48 |
| | | Total AMP Vol. | 5600 |
| 50 | 100 | 0.05 | 1.4 |
| 72 | 122.6 | 0.08 | 1.83 |
| | | Total AMP Vol. | 2800 |

TABLE 11-5

| Results. | | | | | | | |
|---|---|---|---|---|---|---|---|
| Condition | Sample Type | CMV UL56 Target Amount | Internal Control target amount | Percent of Pos | R avg CMV UL56 LogCopy | CMV UL56 Avg. TTime | Internal Control Avg TTime (adjusted) |
| A-100 | CAL02 | 2 | 5.08 | 100.0% | 1.79 | 59.51 | 22.85 |
| A-100 | CAL04 | 4 | 5.08 | 100.0% | 4.43 | 36.99 | 23.37 |
| A-100 | CAL06 | 6 | 5.08 | 100.0% | 5.79 | 24.96 | 25.58 |
| A-100 | CNT001P | 0 | 5.08 | 0.0% | | | 21.90 |
| A-100 | CNT01P | 1 | 5.08 | 100.0% | 0.94 | 63.91 | 21.79 |
| A-100 | CNT03P | 3 | 5.08 | 100.0% | 3.38 | 43.27 | 21.78 |
| A-100 | NEG | 0 | 5.08 | 0.0% | | | 22.47 |
| A-100 | NEG-P | 0 | 5.08 | 0.0% | | | 22.02 |
| A-200 | CAL02 | 2 | 5.08 | 100.0% | 1.87 | 52.05 | 21.85 |
| A-200 | CAL04 | 4 | 5.08 | 100.0% | 4.26 | 34.83 | 21.83 |
| A-200 | CAL06 | 6 | 5.08 | 100.0% | 5.87 | 23.55 | 22.14 |
| A-200 | CNT001P | 0 | 5.08 | 0.0% | | | |
| A-200 | CNT01P | 1 | 5.08 | 0.0% | | | 38.77 |
| A-200 | CNT03P | 3 | 5.08 | 0.0% | | | |
| A-200 | NEG | 0 | 5.08 | 0.0% | | | 21.6 |
| A-200 | NEG-P | 0 | 5.08 | 0.0% | | | 39.2 |
| B-100 | CAL02 | 2 | 5.08 | 100.0% | 1.83 | 57.66 | 23.2 |
| B-100 | CAL04 | 4 | 5.08 | 100.0% | 4.34 | 38.19 | 24.04 |
| B-100 | CAL06 | 6 | 5.08 | 100.0% | 5.83 | 25.01 | 23.69 |
| B-100 | CNT001P | 0 | 5.08 | 0.0% | | | 22.38 |
| B-100 | CNT01P | 1 | 5.08 | 33.3% | 1.33 | 58.63 | 22.18 |
| B-100 | CNT03P | 3 | 5.08 | 100.0% | 3.20 | 44.29 | 22.18 |
| B-100 | NEG | 0 | 5.08 | 0.0% | | | 22.56 |
| B-100 | NEG-P | 0 | 5.08 | 0.0% | | | 22.18 |
| B-200 | CAL02 | 2 | 5.08 | 100.0% | 1.86 | 52.00 | 21.71 |
| B-200 | CAL04 | 4 | 5.08 | 100.0% | 4.28 | 35.19 | 22.20 |
| B-200 | CAL06 | 6 | 5.08 | 100.0% | 5.86 | 23.30 | 22.08 |
| B-200 | CNT001P | 0 | 5.08 | 0.0% | | | 24.46 |
| B-200 | CNT01P | 1 | 5.08 | 33.3% | 1.53 | 62.30 | 24.80 |
| B-200 | CNT03P | 3 | 5.08 | 100.0% | 3.12 | 45.20 | 22.89 |

TABLE 11-5-continued

| Results. | | | | | | | |
|---|---|---|---|---|---|---|---|
| Condition | Sample Type | CMV UL56 Target Amount | Internal Control target amount | Percent of Pos | R avg CMV UL56 LogCopy | CMV UL56 Avg. TTime | Internal Control Avg TTime (adjusted) |
| B-200 | NEG | 0 | 5.08 | 0.0% | | | 21.14 |
| B-200 | NEG-P | 0 | 5.08 | 0.0% | | | 24.16 |

Summary: Using the indicated oligonucleotides, CMV UL56 was readily detected in both plasmid samples and plasma samples when using the formulation B TCR with 200 μL of TER. The Formulation A TCR, with 200 μL TER, performed less well in detecting CMV UL56 in plasma samples.

Example 12. CMV Limit of Detection

The experiments above indicated a limit of detection (LOD) of CMV of 109 IU/mL to 250 IU/mL. Various parameters, including incorporating viral load buffers and enzymes, and salt, oligo, and dNTP/NTP concentrations, were varied to improve detection of CMV in a sample. Adjusting various parameters improved the LOD to 37 IU/mL and the limit of quantitation (LOQ) to 40 IU/mL. In addition, faster CVM TTimes were observed with the improved conditions.

For these studies, $1\times10^2$-$1\times10^7$ copies/mL plasmid encoding CMV UL56 were used as calibrators. In some studies, amplification of 30 copies/mL CMV UL56 plasmid panels was analyzed. In other studies, amplification of cultured virus diluted in processed plasma (Part number B10052) to approximately 70, 30, 10, and 3 copies/mL was analyzed. Exact values were not definitively determined. Nevertheless, these low concentration virus panels were able to be used to compare the sensitivity of the various conditions tested.

TABLE 12-1

| Sensitivity Comparison Between Sequence Files | | | | |
|---|---|---|---|---|
| Panel | N | N Positive | New Sequence File % Positive | Control Sequence File % Positive |
| 70 copies/ mL CMV virus | 10 | 10 | 100% | 100% |
| 30 copies/ mL CMV virus | 15 | 15 | 100% | 80-90% |
| 30 copies/ mL plasmid | 10 | 9 | 90% | 60-80% |
| 10 copies/ mL CMV virus | 30 | 25 | 83% | 45-55% |

TABLE 12-2

| Effect of LiOH concentration in TER. | | | | | |
|---|---|---|---|---|---|
| | | % Positivity | | | |
| Formulation | LiOH | 30 copies/mL plasmid (N = 15) | WHO† 500 IU*/mL (N = 10) | WHO 100 IU*/mL (N = 20) | WHO 60 IU*/mL (N = 20) |
| B TER | 1× (~0.1M) | 60.0 | 20.0 | 2.0 | 5.0 |
| YK Build | 1× (~0.1M) | 80.0 | 70.0 | 10.0 | 10.0 |
| YK Build | 2× (~0.2M) | 93.3 | 100.0 | 5.0 | 5.0 |
| YK Build | 2.5× (~0.25M) | 93.3 | 0.0 | 0.0 | 0.0 |

†World Health Organization CMV standard

*Approximately 0.3 to 0.7 IU per copy.

The addition of 7.5% DMSO in AMP reagent yielded improvement in sensitivity. The addition of DMSO showed higher sensitivity, faster CMV TTimes, and less variability (Table 12-5 and 12-6).

pH titration studies were conducted with HEPES/Trehalose buffer formulation. Results showed that higher AMP1 pH improved sensitivity. High pH in AMP1 and AMP2 decreased sensitivity compared to increasing pH of AMP1 alone. A pH of 8.5 (Tris base increased from 11.4 to 22 mM) was selected for further evaluations.

In some reactions, an increase in $MgCL_2$ in the AMP reagent also improved sensitivity.

Based on the initial studies, additional optimization was carried out as described below. To further improve detection of CMV, additional TCOs were tested as was the addition of displacer oligos, and helper NT7 oligos in AMP buffer. Two displacer oligos (SEQ ID NO: 12 and SEQ ID NO: 41) and three helper NT7 oligos (SEQ ID NO: 14, SEQ ID NO: 17, and SEQ ID NO: 18 were identified that improved detection and precision (i.e., reduce the standard deviation) of CMV.

TABLE 12-3

Combination Testing Studies: Each sample contained modified TCR buffer having 330 mM LiOH.

| Sample | AMP Buffer | TCR Displacer SEQ ID NO. | Helper NT7 SEQ ID NO. |
|---|---|---|---|
| 1 | +DMSO | 12 | 17 |
| 2 | | | 18 |
| 3 | | | 14 |
| 4 | | | 17 + 14 |
| 5 | | 41 | 17 |
| 6 | | | 18 |
| 7 | | | 14 |
| 8 | | | 17 + 14 |
| 9 | −DMSO | 12 | 17 |
| 10 | | | 18 |
| 11 | | | 14 |
| 12 | | | 17 + 14 |
| 13 | | 41 | 17 |
| 14 | | | 18 |
| 15 | | | 14 |
| 16 | | | 17 + 14 |

TABLE 12-4

Combination Test Results by DMSO Addition.

| Sample Type | DMSO in AMP | N tested | N Pos | Avg Log Copy | Std Dev Log Copy | Avg CMV10_ TTime | Avg of CMV10_ TSlope | % Pos |
|---|---|---|---|---|---|---|---|---|
| CAL 1 | + | 40 | 40 | 2.03 | 0.18 | 15.68 | 0.21 | 100.00% |
| | − | 40 | 40 | 2.05 | 0.14 | 16.46 | 0.18 | 100.00% |
| CAL 3 | + | 40 | 40 | 3.94 | 0.06 | 12.13 | 0.22 | 100.00% |
| | − | 40 | 40 | 3.90 | 0.05 | 12.78 | 0.21 | 100.00% |
| CAL 5 | + | 40 | 40 | 6.03 | 0.04 | 8.68 | 0.20 | 100.00% |
| | − | 40 | 40 | 3.05 | 0.07 | 9.35 | 0.21 | 100.00% |
| CTRL A | + | 40 | 0 | | | | 0.03 | 0.00% |
| | − | 40 | 0 | | | | | 0.00% |
| CTRL 30 | + | 120 | 114 | 1.41 | 0.50 | 16.93 | 0.19 | 95.00% |
| | − | 120 | 109 | 1.31 | 0.67 | 18.51 | 0.13 | 90.83% |
| VIRUS 3 | + | 320 | 169 | 0.72 | 0.44 | 17.66 | 0.16 | 52.81% |
| | − | 320 | 191 | 0.64 | 0.46 | 19.21 | 0.12 | 59.69% |
| VIRSU 10 | + | 120 | 120 | 1.42 | 0.36 | 15.89 | 0.21 | 100.00% |
| | − | 120 | 120 | 1.32 | 0.40 | 17.21 | 0.16 | 100.00% |
| VIRUS 30 | + | 80 | 80 | 1.76 | 0.32 | 15.25 | 0.22 | 100.00% |
| | − | 80 | 80 | 1.64 | 0.31 | 16.42 | 0.18 | 100.00% |

TABLE 12-5

Combination Test Results by Displacer Addition.

| Sample Type | Displacer SEQ ID NO. | Count of SampleType | Sum of IsPositive | Avg Log Copy | Std Dev Log Copy | Avg CMV10_TTime | Avg of CMV10_TSlope | % Pos |
|---|---|---|---|---|---|---|---|---|
| CAL 1 | 12 | 40 | 40 | 2.02 | 0.18 | 16.81 | 0.18 | 100.00 |
| | 41 | 40 | 40 | 2.06 | 0.14 | 15.83 | 0.21 | 100.00 |
| CAL 3 | 12 | 40 | 40 | 3.95 | 0.05 | 12.51 | 0.21 | 100.00 |
| | 41 | 40 | 40 | 3.89 | 0.05 | 12.41 | 0.22 | 100.00 |
| CAL 5 | 12 | 40 | 40 | 6.02 | 0.07 | 9.11 | 0.21 | 100.00 |
| | 41 | 40 | 40 | 6.06 | 0.03 | 8.91 | 0.21 | 100.00 |
| CTRL A | 12 | 40 | 0 | | | | 0.02 | 0.00 |
| | 41 | 40 | 0 | | | | 0.03 | 0.00 |
| CTRL 30 | 12 | 120 | 112 | 1.33 | 0.63 | 18.07 | 0.14 | 93.33 |
| | 41 | 120 | 111 | 1.39 | 0.54 | 17.33 | 0.18 | 92.50 |
| VIRUS 3 | 12 | 320 | 169 | 0.67 | 0.49 | 18.84 | 0.13 | 52.81 |
| | 41 | 320 | 191 | 0.68 | 0.42 | 18.16 | 0.14 | 59.69 |
| VIRSU 10 | 12 | 120 | 120 | 1.39 | 0.44 | 16.76 | 0.17 | 100.00 |
| | 41 | 120 | 120 | 1.35 | 0.32 | 16.34 | 0.20 | 100.00 |
| VIRUS 30 | 12 | 80 | 80 | 1.73 | 0.29 | 15.98 | 0.19 | 100.00 |
| | 41 | 80 | 80 | 1.67 | 0.35 | 15.69 | 0.21 | 100.00 |

TABLE 12-6

Combination Test Results by Helper Addition.

| Sample Type | Helper NT7 SEQ ID NO. | Count of SampleType | Sum of IsPositive | Avg Log Copy | StdDev Log Copy | Avg CMV10_TTime | Avg of CMV10_TSlope | % Pos |
|---|---|---|---|---|---|---|---|---|
| CAL 1 | 17 | 20 | 20 | 20.4 | 0.16 | 15.99 | 0.20 | 100.00 |
| | 18 | 20 | 20 | | 0.19 | 16.09 | 0.19 | 100.00 |
| | 14 | 20 | 20 | | 0.15 | 15.18 | 0.20 | 100.00 |
| | 17 + 14 | 20 | 20 | | 0.16 | 15.03 | 0.20 | 100.00 |
| CAL 3 | 17 | 20 | 20 | 3.92 | 0.05 | 12.45 | 0.22 | 100.00 |
| | 18 | 20 | 20 | | 0.05 | 12.40 | 0.22 | 100.00 |
| | 14 | 20 | 20 | | 0.04 | 12.55 | 0.22 | 100.00 |
| | 17 + 14 | 20 | 20 | | 0.09 | 12.43 | 0.22 | 100.00 |
| CAL 5 | 17 | 20 | 20 | 6.05 | 0.03 | 9.07 | 0.21 | 100.00 |
| | 18 | 20 | 20 | | 0.04 | 8.95 | 0.20 | 100.00 |
| | 14 | 20 | 20 | | 0.06 | 9.12 | 0.21 | 100.00 |
| | 17 + 14 | 20 | 20 | | 0.09 | 8.91 | 0.21 | 100.00 |
| CTRL 30 | 17 | 60 | 56 | 1.21 | 0.59 | 18.00 | 0.15 | 90.07 |
| | 18 | 60 | 57 | 1.42 | 0.60 | 17.76 | 0.17 | 95.00 |
| | 14 | 60 | 55 | 1.42 | 0.54 | 17.45 | 0.17 | 91.67 |
| | 17 + 14 | 60 | 53 | 1.40 | 0.60 | 17.57 | 0.15 | 88.33 |
| VIRUS 3 | 17 | 100 | 89 | 0.55 | 0.37 | 18.97 | 0.13 | 55.60 |
| | 18 | 100 | 88 | 0.71 | 0.37 | 18.49 | 0.14 | 55.00 |
| | 14 | 100 | 90 | 0.69 | 0.41 | 18.47 | 0.14 | 56.25 |
| | 17 + 14 | 100 | 93 | 0.75 | 0.38 | 18.01 | 0.14 | 58.13 |
| VIRSU 10 | 17 | 60 | 60 | 1.35 | 0.23 | 16.06 | 0.19 | 100.00 |
| | 18 | 60 | 60 | 1.40 | 0.37 | 16.53 | 0.18 | 100.00 |
| | 14 | 60 | 60 | 1.36 | 0.37 | 16.58 | 0.19 | 100.00 |
| | 17 + 14 | 60 | 60 | 1.38 | 0.32 | 16.42 | 0.19 | 100.00 |
| VIRUS 30 | 17 | 40 | 40 | 1.70 | | 15.67 | 0.20 | 100.00 |
| | 18 | 40 | 40 | 1.67 | | 15.94 | 0.20 | 100.00 |
| | 14 | 40 | 40 | 1.68 | | 16.06 | 0.20 | 100.00 |
| | 17 + 14 | 40 | 40 | 1.75 | | 15.06 | 0.20 | 100.00 |

TABLE 12-7

Confirmation Run of Improved Formulation Compared Against Original Formulation.

| Sample Type | Sam-pleType | N tested | N Pos | % Pos | Avg Recovery (Log c/mL) | SD Recovery (Log c/mL) | Avg of CMV10 TTime | Avg of GIC TTime |
|---|---|---|---|---|---|---|---|---|
| Original assay conditions | CTRL 30 | 15 | 12 | 80.00 | 1.32 | 0.40 | 28.61 | 17.41 |
| | VIRUS 150 | 20 | 20 | 100.00 | 2.14 | 0.42 | 25.09 | 16.74 |
| | VIRUS 70 | 20 | 17 | 85.00 | 1.85 | 0.80 | 26.62 | 16.67 |
| | VIRUS 30 | 20 | 13 | 65.00 | 20.7 | 1.09 | 26.80 | 16.81 |
| | VIRUS 10 | 20 | 8 | 40.00 | 1.27 | 0.86 | 28.72 | 16.8 |
| | VIRUS 3 | 20 | 2 | 10.00 | 2.18 | 0.33 | 24.98 | 16.79 |
| Improved formulation | CTRL 30 | 15 | 14 | 93.33 | 1.25 | 0.63 | 18.21 | 16.48 |
| | VIRUS 30 | 10 | 10 | 100.00 | 1.45 | 0.25 | 16.51 | 15.46 |
| | VIRUS 10 | 15 | 15 | 100.00 | 1.40 | 0.20 | 16.66 | 15.51 |
| | VIRUS 3 | 40 | 24 | 60.00 | 0.64 | 0.44 | 18.48 | 15.43 |

While both displacers improved sensitivity, displacer SEQ ID NO: 41 provided a greater increase in sensitivity than did displacer SEQ ID NO: 12. Results are shown in Table 12-5.

Addition of helper NT7 oligos improved CMV precision by reducing the standard deviation log copies for CMV quantification. Helper NT7 oligo SEQ ID NO: 14 exhibited the lowest standard deviation. Results are shown in Table 12-6.

CMV detection was further tested combining the improvements identified above, including lower amount of TER/LiOH, and addition of displacer and NT7 helper oligonucleotides. These conditions were then run in parallel with the original assay conditions (Aptima assay reagents). Results are shown in Table 12-7.

As shown in Table 12-8, sensitivity was further increases using newly synthesized oligonucleotides having increased purity.

TABLE 12-8

| Oligomers having increase purity showed faster TTime and improved sensitivity. | | | | | |
|---|---|---|---|---|---|
| | | previous Oligomers | | New Oligomers | |
| Panel | N | N Pos | % Pos | N Pos | % Pos |
| CTRL 30 | 10 | 5 | 50 | 8 | 80 |
| VIRUS 10 | 30 | 14 | 47 | 16 | 53 |
| VIRUS 30 | 15 | 12 | 80 | 14 | 93 |
| VIRUS 70 | 10 | 10 | 100 | 10 | 100 |

Significant improvements in sensitivity were observed adding TER to the sample prior to adding TCR. The TER was added first to the sample tubes or wells, followed by sample. After mixing, the TCR was added to the TER-treated sample. Results are shown in Table 12-9.

TABLE 12-9

Sensitivity Results Comparing Sequence Files with WHO Panels (World Health Organization CMV standards).

| Panel Type | Panel # | Dilutions from Panel 1 | Control | All improvements without sequence file change in the order of TER addition | All improvements including sequence file change in order of TER addition |
|---|---|---|---|---|---|
| Cultured Virus in | 1 | Neat | 50% | 65% | 100% |
| B10052 | 2 | $3.33 \times 10^{0}$ | 10% | 23% | 47% |
| WHO material in | 1 | Neat | 100% | 100% | 100% |
| plasma | 2 | $1.00 \times 10^{1}$ | 80% | 100% | 100% |
| | 3 | $1.00 \times 10^{2}$ | 60% | 100% | 100% |
| | 4 | $2.00 \times 10^{2}$ | 30% | 90% | 100% |
| | 5 | $5.00 \times 10^{2}$ | 30% | 80% | 100% |
| | 6 | $6.67 \times 10^{2}$ | 5% | 70% | 80% |
| | 7 | $8.33 \times 10^{2}$ | 10% | 65% | 95% |
| | 8 | $1.00 \times 10^{3}$ | 5% | 60% | 70% |
| | 9 | $1.25 \times 10^{3}$ | 10% | 40% | 75% |
| | 10 | $1.67 \times 10^{3}$ | 0% | 35% | 65% |

TABLE 12-10

Oligos Used in LOD Optimization Studies.

| Reagent | Oligo Type | Target | SEQ ID NO. | Sequence (5'→3') |
|---|---|---|---|---|
| TCR (control) | TCO | CMV UL56 | 42 | GTGGTGGCGCAGAATCGTACGCAGAGTTCGTTTAAAA AAAAAAAAAAAAAAAAAAAAAAAAA |
| | TCO | CMV UL56 | 44 | GTCAGTCGGCATAGCGAGCGGCCTTTAAAAAAAAAAA AAAAAAAAAAAAAAAA |
| | T7 primer | CMV UL56 | 46 | AATTTAATACGACTCACTATAGGGAGAGCAACGAATAC GCCATGGAGCTGGAGTGTCTAAAG |
| | TCO | Internal control | 48 | CGUUCACUAUUGGUCUCUGCAUUCTTTAAAAAAAAA AAAAAAAAAAAAAAAAAAAA |
| | TCO | Internal control | 49 | GCACTGGTGAAATTGCTGCCATTTAAAAAAAAAAAAA AAAAAAAAAAAAAAAAA |
| | T7 Primer | Internal control | 50 | AATTTAATACGACTCACTATAGGGAGAGATGATTGACT TGTGATTCCGC |
| AMP (AMP1) (control) | NT7 Primer | CMV UL56 | 19 | GGTACAGATACACTATAGCCGCCGCGTTT |
| | NT7 Primer | Internal control | 63 | GATTATATAGGACGACAAG |
| PRO (AMP1) (control) | T7 primer | CMV UL56 | 46 | AATTTAATACGACTCACTATAGGGAGAGCAACGAATAC GCCATGGAGCTGGAGTGTCTAAAG |
| | Torch | CMV UL56 | 20 | GGACUCCGCCAGUAACACGUUCGGAUCGCAGUACAG UCC |
| | T7 primer | Control | 50 | AATTTAATACGACTCACTATAGGGAGAGATGATTGACT TGTGATTCCGC |
| | Torch | Control | 72 | GCAUGGUGCGAAUUGGGACAUGC |

TABLE 12-10-continued

| Oligos Used in LOD Optimization Studies. | | | | |
|---|---|---|---|---|
| Reagent | Oligo Type | Target | SEQ ID NO. | Sequence (5'→3') |
| TCR | Displacer | | 12 | GTTACAGAAACTATGCGTA |
| | Displacer | CMV UL56 | 41 | CAGAAACTATGCGTACTGTGT |
| AMP | NT7 Helper | CMV UL56 | 14 | CACCTCCGGGTAGATCTT CC |
| | NT7 Helper | CMV UL56 | 15 | GTACGATTCTGCGCCACCACCT |
| | NT7 Helper | CMV UL56 | 17 | GAACTCTGCGTACGATTCTGCGCCA |
| | NT7 Helper | CMV UL56 | 18 | GAACTCTGCGTACGATTCTGCGCCACCACCT |

Conclusion: Sensitivity and TTimes were improved using the above described conditions. With this new formulation and sequence of TER addition, an LOD of 37 IU/mL and an LOQ of 40 IU/mL were achieved. In some embodiments, the compositions contain the CMV detection oligonucleotides (TCO, T7 primer, NT7 primer, displacer oligonucleotides, helper oligonucleotides, and Torch oligonucleotides) and internal control oligonucleotides TCO, T7 primer, NT7 primer, and Torch oligonucleotides).

Example 13. Torch Identification

Eleven Torches were designed and tested to eliminate ramping and optimize accuracy and positivity.

TABLE 13-1

| CMV UL56 Torches. | | |
|---|---|---|
| Description | SEQ ID NO. | Sequence (5'→3') |
| Torch #1 | 20 | GGACUCCGCCAGUAACACGUUCGGAUCGCAGUACAGUCC |
| Torch #1 THS | 21 | GGACUCCGCCAGUAACACGUUCGGAUCGCAGUAC |
| Torch #2 | 22 | GAACGGCGUGGACUCCGCCAGUAACACGUUCGCGUUC |
| Torch #2 THS | 26 | GAACGGCGUGGACUCCGCCAGUAACACGUUCG |
| Torch #3 | 54 | GAACGGCGUGGACUCCGCCAGUAACGCGUUCGCGUUC |
| Torch #3 THS | 55 | GAACGGCGUGGACUCCGCCAGUAACGCGUUCG |
| Torch #4 | 56 | CCGUGGACUCCGCCAGUAACACGUUCGCACGG |
| Torch #5 | 58 | CGUGGACUCCGCCAGUAACACGUUCGCCACG |
| Torch #5 THS | 59 | CGUGGACUCCGCCAGUAACACGUUCG |
| Torch #6 | 60 | CGGACUCCGCCAGUAACACGUUCGGACCG |
| Torch #6 THS | 61 | CGGACUCCGCCAGUAACACGUUCG |
| Torch #7 | 62 | CGGACUCCGCCAGUAACACGUUCGGGUCCG |
| Torch #7 THS | 39 | CGGACUCCGCCAGUAACACGUUCGG |
| Torch #8 | 64 | CCGUGGACUCCGCCAGUAACACGUUCGGCACGG |
| Torch #8 THS | 65 | CCGUGGACUCCGCCAGUAACACGUUCGG |
| Torch #9 | 66 | CCGUGGACUCCGCCAGUAACACGUUCGGAGCACGG |
| Torch #9 THS | 67 | CCGUGGACUCCGCCAGUAACACGUUCGGAG |
| Torch #10 | 68 | CCGUGGACUCCGCCAGUAACACGUUCGGAUCGCAGCACGG |
| Torch #10 THS | 69 | CCGUGGACUCCGCCAGUAACACGUUCGGAUCGCAG |
| Torch #11 | 70 | CGGACUCCGCCAGUAACACGUUCGGAUCGCAGGACCG |
| Torch #11 THS | 71 | CGGACUCCGCCAGUAACACGUUCGGAUCGCAG |

THS = target hybridizing sequence

TABLE 13-2

| Torch properties. | | | | | | | |
|---|---|---|---|---|---|---|---|
| SEQ ID NO. | MW | Stock (OD/ml) | Stock conc. pmol/µL | Target Conc. pmol/µL | Target Conc. pmol/rxn | Total Volume | Oligo Spike Vol. (µL) |
| 20 | 11875.95 | 20.1 | 67.70 | 0.150 | 3.750 | 4600 | 10.192 |
| 22 | 12235.21 | 32.30 | 105.60 | 0.150 | 3.750 | 4600 | 6.392 |
| 54 | 11213.51 | 11.1 | 39.59 | 0.150 | 3.750 | 4600 | 17.048 |
| 56 | 10877.35 | 19.69 | 72.41 | 0.150 | 3.750 | 4600 | 9.322 |
| 58 | 13600.11 | 18.72 | 55.06 | 0.150 | 3.750 | 4600 | 12.260 |
| 60 | 12937.67 | 19.20 | 59.36 | 0.150 | 3.750 | 4600 | 11.371 |
| 62 | 14598.74 | 21.70 | 59.46 | 0.150 | 3.750 | 4600 | 11.353 |
| 64 | 11516.75 | 26.13 | 90.75 | 0.150 | 3.750 | 4600 | 7.438 |
| 66 | 14224.49 | 5.61 | 394.39 | 0.150 | 3.750 | 4600 | 1.712 |
| 68 | 13578.05 | 26.72 | 78.72 | 0.150 | 3.750 | 4600 | 8.575 |
| 70 | 11268.94 | 31.93 | 113.34 | 0.150 | 3.750 | 4600 | 5.956 |

TABLE 13-3

| Assay conditions. | | | |
|---|---|---|---|
| Sample ID | Sample Type | CMV 10_TargetAmount | Reps |
| 5500000CAL 1-040418 | Cal 1 | 2 | 5 |
| 5500000CAL 2-040418 | Cal 2 | 3 | 5 |
| 5500000CAL 3-040418 | Cal 3 | 4 | 5 |
| 5500000CAL 4-040418 | Cal 4 | 5 | 5 |
| 5500000CAL 5-040418 | Cal 5 | 6 | 5 |
| 5500000CAL 6-040418 | Cal 6 | 7 | 5 |
| CTL A | CTRLA | 0 | 10 |
| Mut3_45 | | 30 | |
| Mut3_1e3 | | 3 | 5 |
| Mut4_45 | | 30 | |
| Mut4_1e3 | | 3 | 5 |
| Mut All_45 | | 30 | |
| Mut All_1e3 | | 5 | |

TABLE 13-3-continued

| Assay conditions. | | | |
|---|---|---|---|
| Sample ID | Sample Type | CMV 10_TargetAmount | Reps |
| VR2356 1E2 c/ml | Clinical Isolate | 2 | 30 |
| VR2356 1E3 c/ml | Clinical Isolate | 3 | 5 |

Of those tested, Torches SEQ ID NO: 20, SEQ ID NO: 60, and SEQ ID NO: 70 showed ramping in negative samples. Torch SEQ ID NO: 54 had low RFU range and lower positivity for R2356 than Torch SEQ ID NO: 20. All oligos additionally tested with mutant CMV sequences to confirm that they would quantify accurately even in the presence of mutations. Torches SEQ ID NO: 62, SEQ ID NO: 64, SEQ ID NO: 66, and SEQ ID NO: 68 showed less sensitivity of detection of Mutant 4. Summary of the results can be found in Table 13-4.

TABLE 13-4

Summary of Torches. Mutant 3, Mutant4, and Mutant All were present at 30 copies. R2356 was present at $1 \times 10^2$ copies.

| Torch | | | Mutant3 | | Mutant4 | | Mutant All | | VR2356 | |
|---|---|---|---|---|---|---|---|---|---|---|
| SEQ ID NO. | RAMP | Reps | Number of Pos | Pct of Pos. | Number of Pos | Pct of Pos. | Number of Pos | Pct of Pos. | Number of Pos | Pct of Pos. |
| 20 | Yes | 30 | 28 | 96.7 | 22 | 73.3 | 27 | 90 | 12 | 40.0 |
| 22 | No | 30 | 28 | 93.3 | 29 | 96.7 | 28 | 93.3 | 19 | 63.3 |
| 54 | No | 30 | 26 | 86.7 | 25 | 83.3 | 28 | 93.3 | 9 | 30.0 |
| 56 | No | 30 | 28 | 93.3 | 29 | 96.7 | 28 | 93.3 | 11 | 36.7 |
| 58 | No | 30 | 28 | 93.3 | 26 | 86.7 | 30 | 100 | 18 | 60.0 |
| 60 | Yes | 30 | 30 | 100 | 30 | 100 | 30 | 100 | 30 | 100 |
| 62 | No | 30 | 29 | 96.7 | 25 | 83.3 | 29 | 96.7 | 17 | 56.7 |
| 64 | No | 30 | 27 | 90.0 | 27 | 90 | 27 | 90 | 13 | 43.3 |
| 66 | No | 30 | 28 | 93.3 | 26 | 86.7 | 25 | 83.3 | 12 | 40.0 |
| 68 | No | 30 | 29 | 96.7 | 26 | 86.7 | 27 | 90 | 13 | 43.3 |
| 70 | yes | 30 | 30 | 100 | 30 | 100 | 29 | 96.7 | 30 | 100 |

Torch (SEQ ID NO: 56) and (SEQ ID NO: 58) didn't produce any ramping for negative samples in FAM background subtracted Curves (CMV Target Channel). Torch SEQ ID NO: 56 and SEQ ID NO: 58 also showed improved positivity in mutant 4 panel, equivalent recovery and improved sensitivity in all panels.

What is claimed is:

1. A kit for amplifying a target region of nucleic acid derived from a human cytomegalovirus (CMV) UL56 gene sequence comprising:

(a) a forward primer comprising 20-31 contiguous nucleobases present in SEQ ID NO: 2 and comprising the nucleobase sequence of SEQ ID NO:11;

(b) a reverse primer comprising 23-40 contiguous nucleobases present in SEQ ID NO: 3 and comprising the nucleobase sequence of SEQ ID NO:23; and (c) a probe oligomer comprising one or more detectable labels, wherein the probe oligomer hybridizes to a CMV amplicon generated by the forward and reverse primers.

2. The kit of claim 1 wherein the forward primer, the reverse primer, or both the forward primer and the reverse primer comprise at least one modified nucleotide selected from the group consisting of: 2'-O-methyl modified nucleotide, a 2'-fluoro modified nucleotide, and a 5'-methyl cytosine.

3. The kit of claim 1, wherein:

(a) the forward primer comprises the nucleobase sequence of SEQ ID NO: 11, SEQ ID NO: 13, or SEQ ID NO: 19; and (b) the reverse primer comprises the nucleobase sequence of SEQ ID NO: 23, SEQ ID NO: 29, SEQ ID NO: 31, or SEQ ID NO: 47.

4. The kit of claim 3, wherein:

(a) an RNA polymerase promoter sequence is linked to the 5' end of the forward primer or the reverse primer;

(b) a T7 RNA polymerase promoter sequence is linked to the 5' end of the forward primer or the reverse primer; or (c) a T7 RNA polymerase promoter sequence having the nucleobase sequence of SEQ ID NO: 78 is linked to the 5' end of the forward rimer or the reverse rimer.

5. The kit of claim 4, wherein the reverse primer comprises the nucleobase sequence of SEQ ID NO: 28, SEQ ID NO: 30, or SEQ ID NO: 46.

6. The kit of claim 1, wherein the probe oligomer comprises:

(a) a nucleobase sequence of SEQ ID NO: 51 or SEQ ID NO: 52, or a nucleobase sequence of SEQ ID NO: 51 or SEQ ID NO: 52 wherein one or more uracil nucleotides are substituted for thymine nucleotides; or (b) a nucleotide sequence comprising 24-35 contiguous nucleobases that hybridizes to SEQ ID NO: 81.

7. The kit of claim 6, wherein the probe oligomer comprises at least one modified nucleotide selected from the group consisting of: a 2'-O-methyl modified nucleotide, a 2'-fluoro modified nucleotide, and a 5'-methyl cytosine.

8. The kit of claim 6, wherein the probe oligomer comprises a nucleobase sequence of SEQ ID NO: 21, SEQ ID NO: 26, SEQ ID NO: 39, SEQ ID NO:
53, SEQ ID NO: 55, SEQ ID NO: 57, SEQ ID NO: 59, SEQ ID NO: 61, SEQ ID NO: 65, SEQ ID NO: 67, SEQ ID NO: 69, or SEQ ID NO: 71.

9. The kit of claim 8, wherein the probe oligomer contains:

(a) a fluorescent molecule attached to the 5' or 3' end of the probe oligomer; and/or (b) 4-5 nucleobases at the 3' end of the probe oligomer that are complementary to 4-5 nucleobases at the 5' end of the probe oligomer wherein (i) a fluorescent molecule is attached to the 5' end of the probe oligomer and a quencher is attached to the 3' end of the probe oligomer; or (ii) a fluorescent molecule is attached to the 3' end of the probe oligomer and a quencher is attached to the 5' end of the probe oligomer.

10. The kit of claim 9, wherein the probe oligomer comprises the nucleobase sequence of SEQ ID NO: 20, SEQ ID NO: 22, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, or SEQ ID NO: 70.

11. The kit of claim 6, further comprising:

(a) a helper oligomer comprising 19-31 contiguous nucleobases having at least 90% identity to a 19-31 nucleotide sequence present in SEQ ID NO: 2, wherein the helper oligomer is blocked or unblocked; and/or (b) a displacer oligomer comprising 21-27 contiguous nucleobases having at least 90% identity to a 21-25 nucleotide sequence present in SEQ ID NO: 5.

12. The kit of claim 11, wherein:

(a) the helper oligomer comprises a nucleotide sequence selected from the group consisting of SEQ ID NO: 10, SEQ ID NO: 14, SEQ ID NO: 15, SEQ ID NO: 17, and SEQ ID NO: 18; and/or (b) the displacer oligomer comprises a nucleotide sequence selected from the group consisting of: SEQ ID NO: 6, SEQ ID NO: 12, SEQ ID NO: 25, SEQ ID NO: 33, SEQ ID NO: 35, SEQ ID NO: 37, SEQ ID NO: 41, SEQ ID NO: 72, SEQ ID NO: 73, SEQ ID NO: 74, SEQ ID NO: 75, SEQ ID NO: 76, SEQ ID NO: 77, SEQ ID NO: 86, SEQ ID NO: 87, and SEQ ID NO: 88.

13. The kit of claim 6, further comprising at least one target capture oligomer (TCO) comprising the nucleobase sequence of SEQ ID NO: 6, SEQ ID NO: 8, SEQ ID NO: 43, SEQ ID NO: 45, SEQ ID NO: 7, SEQ ID NO: 9, SEQ ID NO: 42, or SEQ ID NO:44.

14. The kit of claim 1, wherein:

(a) the forward primer comprises SEQ ID NO: 11 and the reverse primer comprises SEQ ID NO: 23;

(b) the forward rimer com rises SEQ ID NO: 11, the reverse rimer comprises SEQ ID NO: 23, and the kit further comprises a probe oligomer comprising SEQ ID NO: 53;

(c) the forward primer comprises SEQ ID NO:19 and the reverse primer comprises SEQ ID NO: 46;

(d) the forward rimer comprises SEQ ID NO:19, the reverse rimer comprises SEQ ID NO: 46, and the kit further comprises a probe oligomer comprising SEQ ID NO: 56;

(e) the forward primer comprises SEQ ID NO:19, the reverse primer comprises SEQ ID NO: 46, and the kit further comprises a probe oligomer comprising SEQ ID NO: 56, and at least one of a TCO comprising SEQ ID NO: 42 and a TCO comprising SEQ ID NO: 44;

(f) the forward primer comprises SEQ ID NO:19, the reverse rimer comprises SEQ ID NO: 46, and the kit further comprises a probe oligomer comprising SEQ ID NO: 56, a helper oligomer comprising SEQ ID NO: 14, and a displacer oligomer comprising SEQ ID NO: 41; or (g) the forward primer comprises SEQ ID NO:19, the reverse primer comprises SEQ ID NO: 46, and the kit further comprises a probe oligomer comprising SEQ ID NO: 56, a helper oligomer comprising SEQ ID NO: 14, a displacer oligomer comprising SEQ ID NO: 41, and at least one of a TCO comprising SEQ ID NO: 42 and a TCO comprising SEQ ID NO: 44.

15. The kit of claim 14, further comprising one or more of: a target capture reagent, a target capture wash solution, a target enhancer reagent, an amplification reagent, an enzyme reagent, a promoter reagent, a CMV positive control nucleic acid, a negative control nucleic acid, a sample transport medium, a reverse transcriptase, an RNA polymerase, dNTPs, NTPs, a buffer, positive and/or negative control samples, an internal control promoter primer comprising SEQ ID NO: 50, an internal control primer comprising SEQ ID NO: 63, an internal probe oligomer comprising SEQ ID NO: 88, and an internal control TCO comprising SEQ ID NO:49.

16. A method for amplifying and detecting a target region of nucleic acid derived from a human cytomegalovirus (CMV) UL56 gene sequence present in a sample, the method comprising:

(a) contacting the sample with a forward primer and a reverse primer configured to amplify a CMV UL56 amplicon, wherein the forward primer comprises 20-31 contiguous nucleobases present in SEQ ID NO: 2 and comprising the nucleobase sequence of SEQ ID NO:11, and the reverse primer comprises 23-40 contiguous nucleobases present in SEQ ID NO: 3, and comprising the nucleobase sequence of SEQ ID NO:23;

(b) exposing the sample to conditions sufficient to amplify the target region thereby producing an amplification product if the CMV UL56 gene sequence is present in the sample; and (c) detecting and/or quantifying the presence or absence of the amplification product.

17. The method of claim 16, wherein the amplifying comprises a thermal cycling reaction, a polymerase chain reaction (PCR), an isothermal nucleic acid amplification reaction, a transcription-mediated amplification (TMA), a biphasic TMA, a nucleic acid sequence-based amplification, a replicase-mediated amplification, a Qβ-replicase-mediated amplification, a ligase chain reaction (LCR), or a strand-displacement amplification (SDA).

* * * * *

SEQUENCE LISTING

<160> NUMBER OF SEQ ID NOS: 87

<210> SEQ ID NO 1
<211> LENGTH: 312
<212> TYPE: DNA
<213> ORGANISM: Artificial Sequence
<220> FEATURE:
<223> OTHER INFORMATION: partial sequence from human CMV UL56 gene

<400> SEQUENCE: 1
gtatcctcgt gcagcgcctt cagcagcatc tccagataga gagtcagcag cgaactctgc 60
gtacgattct gcgccaccac ctccgggtag atcttccggt acagatacac tatagccgcc 120
gcgtttctct tgaacggcgt ggactccgcc agtaacacgt tcggatcgca gtactttaga 180
cactccagct ccatggcgta ttcgttgcat ttcgaacaca ctacgcatag tttctgtaac 240
aaattcatct ccatgactcg actcgctcac gtacgagacg ctgtcgtccg gtctggcgcc 300
ggccagagac at 312

<210> SEQ ID NO 2
<211> LENGTH: 75
<212> TYPE: DNA
<213> ORGANISM: Artificial Sequence
<220> FEATURE:
<223> OTHER INFORMATION: partial sequence from human CMV UL56 gene

<400> SEQUENCE: 2
gaactctgcg tacgattctg cgccaccacc tccgggtaga tcttccggta cagatacact 60
atagccgccg cgttt 75

<210> SEQ ID NO 3
<211> LENGTH: 105
<212> TYPE: DNA
<213> ORGANISM: Artificial Sequence
<220> FEATURE:
<223> OTHER INFORMATION: partial sequence from human CMV UL56 gene

<400> SEQUENCE: 3
tcgtacgtga gcgagtcgag tcatggagat gaatttgtta cagaaactat gcgtagtgtg 60
ttcgaaatgc aacgaatacg ccatggagct ggagtgtcta aagta 105

<210> SEQ ID NO 4
<211> LENGTH: 40
<212> TYPE: DNA
<213> ORGANISM: Artificial Sequence
<220> FEATURE:
<223> OTHER INFORMATION: partial sequence from human CMV UL56 gene

<400> SEQUENCE: 4
gaacggcgtg gactccgcca gtaacacgtt cggatcgcag 40

<210> SEQ ID NO 5
<211> LENGTH: 61
<212> TYPE: DNA
<213> ORGANISM: Artificial Sequence
<220> FEATURE:
<223> OTHER INFORMATION: partial sequence from human CMV UL56 gene

<400> SEQUENCE: 5
tcgtacgtga gcgagtcgag tcatggagat gaatttgtta cagaaactat gcgtagtgtg 60
t 61

<210> SEQ ID NO 6
<211> LENGTH: 23
<212> TYPE: DNA
<213> ORGANISM: Artificial Sequence
<220> FEATURE:
<223> OTHER INFORMATION: synthetic oligo

<400> SEQUENCE: 6
gtacgtgagc gagtcgagtc atg 23

<210> SEQ ID NO 7
<211> LENGTH: 56
<212> TYPE: DNA
<213> ORGANISM: Artificial Sequence
<220> FEATURE:
<223> OTHER INFORMATION: synthetic oligo

<400> SEQUENCE: 7
gtacgtgagc gagtcgagtc atgtttaaaa aaaaaaaaaa aaaaaaaaaa aaaaaa 56

<210> SEQ ID NO 8
<211> LENGTH: 22
<212> TYPE: DNA
<213> ORGANISM: Artificial Sequence
<220> FEATURE:
<223> OTHER INFORMATION: synthetic oligo

<400> SEQUENCE: 8
tgtcacttcc ttgagtatat ag 22

<210> SEQ ID NO 9
<211> LENGTH: 55
<212> TYPE: DNA
<213> ORGANISM: Artificial Sequence
<220> FEATURE:
<223> OTHER INFORMATION: synthetic oligo

<400> SEQUENCE: 9
tgtcacttcc ttgagtatat agtttaaaaa aaaaaaaaaa aaaaaaaaaa aaaaa 55

<210> SEQ ID NO 10
<211> LENGTH: 16
<212> TYPE: DNA
<213> ORGANISM: Artificial Sequence
<220> FEATURE:
<223> OTHER INFORMATION: synthetic oligo

<400> SEQUENCE: 10
gtacgattct gcgcca 16

<210> SEQ ID NO 11
<211> LENGTH: 20
<212> TYPE: DNA
<213> ORGANISM: Artificial Sequence
<220> FEATURE:
<223> OTHER INFORMATION: Synthetic oligo

<400> SEQUENCE: 11
cagatacact atagccgccg 20

<210> SEQ ID NO 12
<211> LENGTH: 19
<212> TYPE: DNA
<213> ORGANISM: Artificial Sequence
<220> FEATURE:
<223> OTHER INFORMATION: Synthetic oligo

<400> SEQUENCE: 12
gttacagaaa ctatgcgta 19

<210> SEQ ID NO 13
<211> LENGTH: 23
<212> TYPE: DNA
<213> ORGANISM: Artificial Sequence
<220> FEATURE:
<223> OTHER INFORMATION: Synthetic oligo

<400> SEQUENCE: 13
gtacagatac actatagccg ccg 23

<210> SEQ ID NO 14
<211> LENGTH: 19
<212> TYPE: DNA
<213> ORGANISM: Artificial Sequence
<220> FEATURE:
<223> OTHER INFORMATION: Synthetic oligo

<400> SEQUENCE: 14
cacctccggg tagatcttc 19

<210> SEQ ID NO 15
<211> LENGTH: 22
<212> TYPE: DNA
<213> ORGANISM: Artificial Sequence
<220> FEATURE:
<223> OTHER INFORMATION: Synthetic oligo

<400> SEQUENCE: 15
gtacgattct gcgccaccac ct 22

<210> SEQ ID NO 16
<211> LENGTH: 23
<212> TYPE: DNA
<213> ORGANISM: Artificial Sequence
<220> FEATURE:
<223> OTHER INFORMATION: Synthetic oligo

<400> SEQUENCE: 16
actctgcgta cgattctgcg cca 23

<210> SEQ ID NO 17
<211> LENGTH: 25
<212> TYPE: DNA
<213> ORGANISM: Artificial Sequence
<220> FEATURE:
<223> OTHER INFORMATION: Synthetic oligo

<400> SEQUENCE: 17
gaactctgcg tacgattctg cgcca 25

<210> SEQ ID NO 18
<211> LENGTH: 31
<212> TYPE: DNA
<213> ORGANISM: Artificial Sequence
<220> FEATURE:
<223> OTHER INFORMATION: Synthetic oligo

<400> SEQUENCE: 18
gaactctgcg tacgattctg cgccaccacc t 31

<210> SEQ ID NO 19
<211> LENGTH: 29

<212> TYPE: DNA
<213> ORGANISM: Artificial Sequence
<220> FEATURE:
<223> OTHER INFORMATION: Synthetic oligo

<400> SEQUENCE: 19
ggtacagata cactatagcc gccgcgttt 29

<210> SEQ ID NO 20
<211> LENGTH: 39
<212> TYPE: DNA
<213> ORGANISM: Artificial Sequence
<220> FEATURE:
<223> OTHER INFORMATION: Synthetic oligo

<400> SEQUENCE: 20
ggacuccgcc aguaacacgu ucggaucgca guacagucc 39

<210> SEQ ID NO 21
<211> LENGTH: 34
<212> TYPE: DNA
<213> ORGANISM: Artificial Sequence
<220> FEATURE:
<223> OTHER INFORMATION: Synthetic oligo

<400> SEQUENCE: 21
ggacuccgcc aguaacacgu ucggaucgca guac 34

<210> SEQ ID NO 22
<211> LENGTH: 37
<212> TYPE: DNA
<213> ORGANISM: Artificial Sequence
<220> FEATURE:
<223> OTHER INFORMATION: Synthetic oligo

<400> SEQUENCE: 22
gaacggcgug gacuccgcca guaacacguu cgcguuc 37

<210> SEQ ID NO 23
<211> LENGTH: 23
<212> TYPE: DNA
<213> ORGANISM: Artificial Sequence
<220> FEATURE:
<223> OTHER INFORMATION: Synthetic oligo

<400> SEQUENCE: 23
ccatggagct ggagtgtcta aag 23

<210> SEQ ID NO 24
<211> LENGTH: 15
<212> TYPE: DNA
<213> ORGANISM: Artificial Sequence
<220> FEATURE:
<223> OTHER INFORMATION: Synthetic oligo

<400> SEQUENCE: 24
aatgcaacga atacg 15

<210> SEQ ID NO 25
<211> LENGTH: 22
<212> TYPE: DNA
<213> ORGANISM: Artificial Sequence
<220> FEATURE:
<223> OTHER INFORMATION: Synthetic oligo

<400> SEQUENCE: 25
gtacgtgagc gagtcgagtc at 22

<210> SEQ ID NO 26
<211> LENGTH: 32
<212> TYPE: DNA
<213> ORGANISM: Artificial Sequence
<220> FEATURE:
<223> OTHER INFORMATION: Synthetic oligo

<400> SEQUENCE: 26
gaacggcgug gacuccgcca guaacacguu cg 32

<210> SEQ ID NO 27
<211> LENGTH: 24
<212> TYPE: DNA
<213> ORGANISM: Artificial Sequence
<220> FEATURE:
<223> OTHER INFORMATION: Synthetic oligo

<400> SEQUENCE: 27
tgtgttcgaa atgcaacgaa tacg 24

<210> SEQ ID NO 28
<211> LENGTH: 67
<212> TYPE: DNA
<213> ORGANISM: Artificial Sequence
<220> FEATURE:
<223> OTHER INFORMATION: Synthetic oligo

<400> SEQUENCE: 28
aatttaatac gactcactat agggagaaat gcaacgaata cgccatggag ctggagtgtc 60
taaagta 67

<210> SEQ ID NO 29
<211> LENGTH: 40
<212> TYPE: DNA
<213> ORGANISM: Artificial Sequence
<220> FEATURE:
<223> OTHER INFORMATION: Synthetic oligo

<400> SEQUENCE: 29
aatgcaacga atacgccatg gagctggagt gtctaaagta 40

<210> SEQ ID NO 30
<211> LENGTH: 66
<212> TYPE: DNA
<213> ORGANISM: Artificial Sequence
<220> FEATURE:
<223> OTHER INFORMATION: Synthetic oligo

<400> SEQUENCE: 30
aatttaatac gactcactat agggagaaat gcaacgaata cgccatggag ctggagtgtc 60
taaagt 66

<210> SEQ ID NO 31
<211> LENGTH: 39
<212> TYPE: DNA
<213> ORGANISM: Artificial Sequence
<220> FEATURE:
<223> OTHER INFORMATION: Synthetic oligo

<400> SEQUENCE: 31
aatgcaacga atacgccatg gagctggagt gtctaaagt 39

<210> SEQ ID NO 32
<211> LENGTH: 52
<212> TYPE: DNA
<213> ORGANISM: Artificial Sequence
<220> FEATURE:
<223> OTHER INFORMATION: Synthetic oligo

<400> SEQUENCE: 32
aatttaatac gactcactat agggagatcg tacgtgagcg agtcgagtca tg 52

<210> SEQ ID NO 33
<211> LENGTH: 25
<212> TYPE: DNA
<213> ORGANISM: Artificial Sequence
<220> FEATURE:
<223> OTHER INFORMATION: Synthetic oligo

<400> SEQUENCE: 33
tcgtacgtga gcgagtcgag tcatg 25

<210> SEQ ID NO 34
<211> LENGTH: 51
<212> TYPE: DNA
<213> ORGANISM: Artificial Sequence
<220> FEATURE:
<223> OTHER INFORMATION: Synthetic oligo

<400> SEQUENCE: 34
aatttaatac gactcactat agggagatcg tacgtgagcg agtcgagtca t 51

<210> SEQ ID NO 35
<211> LENGTH: 24
<212> TYPE: DNA
<213> ORGANISM: Artificial Sequence
<220> FEATURE:
<223> OTHER INFORMATION: Synthetic oligo

<400> SEQUENCE: 35
tcgtacgtga gcgagtcgag tcat 24

<210> SEQ ID NO 36
<211> LENGTH: 51
<212> TYPE: DNA
<213> ORGANISM: Artificial Sequence
<220> FEATURE:
<223> OTHER INFORMATION: Synthetic oligo

<400> SEQUENCE: 36
aatttaatac gactcactat agggagacgt acgtgagcga gtcgagtcat g 51

<210> SEQ ID NO 37
<211> LENGTH: 24
<212> TYPE: DNA
<213> ORGANISM: Artificial Sequence
<220> FEATURE:
<223> OTHER INFORMATION: Synthetic oligo

<400> SEQUENCE: 37
cgtacgtgag cgagtcgagt catg 24

<210> SEQ ID NO 38
<211> LENGTH: 50
<212> TYPE: DNA
<213> ORGANISM: Artificial Sequence
<220> FEATURE:
<223> OTHER INFORMATION: Synthetic oligo

<400> SEQUENCE: 38
aatttaatac gactcactat agggagagta cgtgagcgag tcgagtcatg 50

<210> SEQ ID NO 39
<211> LENGTH: 25
<212> TYPE: DNA
<213> ORGANISM: Artificial Sequence
<220> FEATURE:
<223> OTHER INFORMATION: Synthetic oligo

<400> SEQUENCE: 39
cggacuccgc caguaacacg uucgg 25

<210> SEQ ID NO 40
<211> LENGTH: 48
<212> TYPE: DNA
<213> ORGANISM: Artificial Sequence
<220> FEATURE:
<223> OTHER INFORMATION: Synthetic oligo

<400> SEQUENCE: 40
aatttaatac gactcactat agggagacag aaactatgcg tactgtgt 48

<210> SEQ ID NO 41
<211> LENGTH: 21
<212> TYPE: DNA
<213> ORGANISM: Artificial Sequence
<220> FEATURE:
<223> OTHER INFORMATION: Synthetic oligo

<400> SEQUENCE: 41
cagaaactat gcgtactgtg t 21

<210> SEQ ID NO 42
<211> LENGTH: 63
<212> TYPE: DNA
<213> ORGANISM: Artificial Sequence
<220> FEATURE:
<223> OTHER INFORMATION: Synthetic oligo

<400> SEQUENCE: 42
gtggtggcgc agaatcgtac gcagagttcg tttaaaaaaa aaaaaaaaaa aaaaaaaaaa 60
aaa 63

<210> SEQ ID NO 43
<211> LENGTH: 30
<212> TYPE: DNA
<213> ORGANISM: Artificial Sequence
<220> FEATURE:
<223> OTHER INFORMATION: Synthetic oligo

<400> SEQUENCE: 43
gtggtggcgc agaatcgtac gcagagttcg 30

<210> SEQ ID NO 44
<211> LENGTH: 56
<212> TYPE: DNA
<213> ORGANISM: Artificial Sequence
<220> FEATURE:
<223> OTHER INFORMATION: Synthetic oligo

<400> SEQUENCE: 44
gtcagtcggc atagcgagcg gcctttaaaa aaaaaaaaaa aaaaaaaaaa aaaaaa 56

<210> SEQ ID NO 45
<211> LENGTH: 23
<212> TYPE: DNA
<213> ORGANISM: Artificial Sequence
<220> FEATURE:
<223> OTHER INFORMATION: Synthetic oligo

<400> SEQUENCE: 45
gtcagtcggc atagcgagcg gcc 23

<210> SEQ ID NO 46
<211> LENGTH: 62
<212> TYPE: DNA
<213> ORGANISM: Artificial Sequence
<220> FEATURE:
<223> OTHER INFORMATION: Synthetic oligo

<400> SEQUENCE: 46
aatttaatac gactcactat agggagagca acgaatacgc catggagctg gagtgtctaa 60
ag 62

<210> SEQ ID NO 47
<211> LENGTH: 35
<212> TYPE: DNA
<213> ORGANISM: Artificial Sequence
<220> FEATURE:
<223> OTHER INFORMATION: Synthetic oligo

<400> SEQUENCE: 47
gcaacgaata cgccatggag ctggagtgtc taaag 35

<210> SEQ ID NO 48
<211> LENGTH: 57
<212> TYPE: DNA
<213> ORGANISM: Artificial Sequence
<220> FEATURE:
<223> OTHER INFORMATION: Synthetic oligo

<400> SEQUENCE: 48
cguucacuau uggucucugc auuctttaaa aaaaaaaaaa aaaaaaaaaa aaaaaaa 57

<210> SEQ ID NO 49
<211> LENGTH: 54
<212> TYPE: DNA
<213> ORGANISM: Artificial Sequence
<220> FEATURE:
<223> OTHER INFORMATION: Synthetic oligo

<400> SEQUENCE: 49
aaaaaaaaaa aaaaaaaaaa aaaaaaaaaa tttaccgtcg ttaaagtggt cacg 54

<210> SEQ ID NO 50
<211> LENGTH: 49
<212> TYPE: DNA
<213> ORGANISM: Artificial Sequence
<220> FEATURE:
<223> OTHER INFORMATION: Synthetic oligo

<400> SEQUENCE: 50
aatttaatac gactcactat agggagagat gattgacttg tgattccgc 49

<210> SEQ ID NO 51
<211> LENGTH: 16
<212> TYPE: DNA
<213> ORGANISM: Artificial Sequence
<220> FEATURE:

<223> OTHER INFORMATION: Synthetic oligo

<400> SEQUENCE: 51
ggactccgcc agtaac 16

<210> SEQ ID NO 52
<211> LENGTH: 23
<212> TYPE: DNA
<213> ORGANISM: Artificial Sequence
<220> FEATURE:
<223> OTHER INFORMATION: Synthetic oligo

<400> SEQUENCE: 52
ggactccgcc agtaacacgt tcg 23

<210> SEQ ID NO 53
<211> LENGTH: 24
<212> TYPE: DNA
<213> ORGANISM: Artificial Sequence
<220> FEATURE:
<223> OTHER INFORMATION: Synthetic oligo

<400> SEQUENCE: 53
cgtggactcc gccagtaaca cgtt 24

<210> SEQ ID NO 54
<211> LENGTH: 37
<212> TYPE: DNA
<213> ORGANISM: Artificial Sequence
<220> FEATURE:
<223> OTHER INFORMATION: Synthetic oligo

<400> SEQUENCE: 54
gaacggcgug gacuccgcca guaacgcguu cgcguuc 37

<210> SEQ ID NO 55
<211> LENGTH: 32
<212> TYPE: DNA
<213> ORGANISM: Artificial Sequence
<220> FEATURE:
<223> OTHER INFORMATION: Synthetic oligo

<400> SEQUENCE: 55
gaacggcgug gacuccgcca guaacgcguu cg 32

<210> SEQ ID NO 56
<211> LENGTH: 32
<212> TYPE: DNA
<213> ORGANISM: Artificial Sequence
<220> FEATURE:
<223> OTHER INFORMATION: Synthetic oligo

<400> SEQUENCE: 56
ccguggacuc cgccaguaac acguucgcac gg 32

<210> SEQ ID NO 57
<211> LENGTH: 27
<212> TYPE: DNA
<213> ORGANISM: Artificial Sequence
<220> FEATURE:
<223> OTHER INFORMATION: Synthetic oligo

<400> SEQUENCE: 57
ccguggacuc cgccaguaac acguucg 27

<210> SEQ ID NO 58
<211> LENGTH: 31
<212> TYPE: DNA
<213> ORGANISM: Artificial Sequence
<220> FEATURE:
<223> OTHER INFORMATION: Synthetic oligo

<400> SEQUENCE: 58
cguggacucc gccaguaaca cguucgccac g 31

<210> SEQ ID NO 59
<211> LENGTH: 26
<212> TYPE: DNA
<213> ORGANISM: Artificial Sequence
<220> FEATURE:
<223> OTHER INFORMATION: Synthetic oligo

<400> SEQUENCE: 59
cguggacucc gccaguaaca cguucg 26

<210> SEQ ID NO 60
<211> LENGTH: 29
<212> TYPE: DNA
<213> ORGANISM: Artificial Sequence
<220> FEATURE:
<223> OTHER INFORMATION: Synthetic oligo

<400> SEQUENCE: 60
cggacuccgc caguaacacg uucggaccg 29

<210> SEQ ID NO 61
<211> LENGTH: 24
<212> TYPE: DNA
<213> ORGANISM: Artificial Sequence
<220> FEATURE:
<223> OTHER INFORMATION: Synthetic oligo

<400> SEQUENCE: 61
cggacuccgc caguaacacg uucg 24

<210> SEQ ID NO 62
<211> LENGTH: 30
<212> TYPE: DNA
<213> ORGANISM: Artificial Sequence
<220> FEATURE:
<223> OTHER INFORMATION: Synthetic oligo

<400> SEQUENCE: 62
cggacuccgc caguaacacg uucggguccg 30

<210> SEQ ID NO 63
<211> LENGTH: 19
<212> TYPE: DNA
<213> ORGANISM: Artificial Sequence
<220> FEATURE:
<223> OTHER INFORMATION: Synthetic oligo

<400> SEQUENCE: 63
gattatatag gacgacaag 19

<210> SEQ ID NO 64
<211> LENGTH: 33
<212> TYPE: DNA
<213> ORGANISM: Artificial Sequence
<220> FEATURE:
<223> OTHER INFORMATION: Synthetic oligo

<400> SEQUENCE: 64
ccguggacuc cgccaguaac acguucggca cgg 33

<210> SEQ ID NO 65
<211> LENGTH: 28
<212> TYPE: DNA
<213> ORGANISM: Artificial Sequence
<220> FEATURE:
<223> OTHER INFORMATION: Synthetic oligo

<400> SEQUENCE: 65
ccguggacuc cgccaguaac acguucgg 28

<210> SEQ ID NO 66
<211> LENGTH: 35
<212> TYPE: DNA
<213> ORGANISM: Artificial Sequence
<220> FEATURE:
<223> OTHER INFORMATION: Synthetic oligo

<400> SEQUENCE: 66
ccguggacuc cgccaguaac acguucggag cacgg 35

<210> SEQ ID NO 67
<211> LENGTH: 30
<212> TYPE: DNA
<213> ORGANISM: Artificial Sequence
<220> FEATURE:
<223> OTHER INFORMATION: Synthetic oligo

<400> SEQUENCE: 67
ccguggacuc cgccaguaac acguucggag 30

<210> SEQ ID NO 68
<211> LENGTH: 40
<212> TYPE: DNA
<213> ORGANISM: Artificial Sequence
<220> FEATURE:
<223> OTHER INFORMATION: Synthetic oligo

<400> SEQUENCE: 68
ccguggacuc cgccaguaac acguucggau cgcagcacgg 40

<210> SEQ ID NO 69
<211> LENGTH: 35
<212> TYPE: DNA
<213> ORGANISM: Artificial Sequence
<220> FEATURE:
<223> OTHER INFORMATION: Synthetic oligo

<400> SEQUENCE: 69
ccguggacuc cgccaguaac acguucggau cgcag 35

<210> SEQ ID NO 70
<211> LENGTH: 37
<212> TYPE: DNA
<213> ORGANISM: Artificial Sequence
<220> FEATURE:
<223> OTHER INFORMATION: Synthetic oligo

<400> SEQUENCE: 70
cggacuccgc caguaacacg uucggaucgc aggaccg 37

<210> SEQ ID NO 71
<211> LENGTH: 32

<212> TYPE: DNA
<213> ORGANISM: Artificial Sequence
<220> FEATURE:
<223> OTHER INFORMATION: Synthetic oligo

<400> SEQUENCE: 71
cggacuccgc caguaacacg uucggaucgc ag 32

<210> SEQ ID NO 72
<211> LENGTH: 25
<212> TYPE: DNA
<213> ORGANISM: Artificial Sequence
<220> FEATURE:
<223> OTHER INFORMATION: Synthetic oligo

<400> SEQUENCE: 72
atgaatttgt tacagaaact atgcg 25

<210> SEQ ID NO 73
<211> LENGTH: 27
<212> TYPE: DNA
<213> ORGANISM: Artificial Sequence
<220> FEATURE:
<223> OTHER INFORMATION: Synthetic oligo

<400> SEQUENCE: 73
atgaatttgt tacagaaact atgcgta 27

<210> SEQ ID NO 74
<211> LENGTH: 25
<212> TYPE: DNA
<213> ORGANISM: Artificial Sequence
<220> FEATURE:
<223> OTHER INFORMATION: Synthetic oligo

<400> SEQUENCE: 74
gaatttgtta cagaaactat gcgta 25

<210> SEQ ID NO 75
<211> LENGTH: 23
<212> TYPE: DNA
<213> ORGANISM: Artificial Sequence
<220> FEATURE:
<223> OTHER INFORMATION: Synthetic oligo

<400> SEQUENCE: 75
gaatttgtta cagaaactat gcg 23

<210> SEQ ID NO 76
<211> LENGTH: 20
<212> TYPE: DNA
<213> ORGANISM: Artificial Sequence
<220> FEATURE:
<223> OTHER INFORMATION: Synthetic oligo

<400> SEQUENCE: 76
tgttacagaa actatgcgta 20

<210> SEQ ID NO 77
<211> LENGTH: 24
<212> TYPE: DNA
<213> ORGANISM: Artificial Sequence
<220> FEATURE:
<223> OTHER INFORMATION: Synthetic oligo

<400> SEQUENCE: 77
gttacagaaa ctatgcgtac tgtg 24

<210> SEQ ID NO 78
<211> LENGTH: 27
<212> TYPE: DNA
<213> ORGANISM: Artificial Sequence
<220> FEATURE:
<223> OTHER INFORMATION: Synthetic oligo

<400> SEQUENCE: 78
aatttaatac gactcactat agggaga 27

<210> SEQ ID NO 79
<211> LENGTH: 75
<212> TYPE: DNA
<213> ORGANISM: Artificial Sequence
<220> FEATURE:
<223> OTHER INFORMATION: partial sequence from human CMV UL56 gene

<400> SEQUENCE: 79
aaacgcggcg gctatagtgt atctgtaccg gaagatctac ccggaggtgg tggcgcagaa 60
tcgtacgcag agttc 75

<210> SEQ ID NO 80
<211> LENGTH: 105
<212> TYPE: DNA
<213> ORGANISM: Artificial Sequence
<220> FEATURE:
<223> OTHER INFORMATION: partial sequence from human CMV UL56 gene

<400> SEQUENCE: 80
tactttagac actccagctc catggcgtat tcgttgcatt tcgaacacac tacgcatagt 60
ttctgtaaca aattcatctc catgactcga ctcgctcacg tacga 105

<210> SEQ ID NO 81
<211> LENGTH: 40
<212> TYPE: DNA
<213> ORGANISM: Artificial Sequence
<220> FEATURE:
<223> OTHER INFORMATION: partial sequence from human CMV UL56 gene

<400> SEQUENCE: 81
ctgcgatccg aacgtgttac tggcggagtc cacgccgttc 40

<210> SEQ ID NO 82
<211> LENGTH: 61
<212> TYPE: DNA
<213> ORGANISM: Artificial Sequence
<220> FEATURE:
<223> OTHER INFORMATION: partial sequence from human CMV UL56 gene

<400> SEQUENCE: 82
acacactacg catagtttct gtaacaaatt catctccatg actcgactcg ctcacgtacg 60
a 61

<210> SEQ ID NO 83
<211> LENGTH: 20
<212> TYPE: DNA
<213> ORGANISM: Artificial Sequence
<220> FEATURE:
<223> OTHER INFORMATION: Synthetic oligo

<400> SEQUENCE: 83
atggtcaatt agagacaaag 20

-continued

```
<210> SEQ ID NO 84
<211> LENGTH: 20
<212> TYPE: DNA
<213> ORGANISM: Artificial Sequence
<220> FEATURE:
<223> OTHER INFORMATION: Synthetic oligo

<400> SEQUENCE: 84

cgttcactat tggtctctgc                                         20


<210> SEQ ID NO 85
<211> LENGTH: 26
<212> TYPE: DNA
<213> ORGANISM: Artificial Sequence
<220> FEATURE:
<223> OTHER INFORMATION: Synthetic oligo

<400> SEQUENCE: 85

cggaatcaca agtcaatcat cgcgca                                  26


<210> SEQ ID NO 86
<211> LENGTH: 20
<212> TYPE: DNA
<213> ORGANISM: Artificial Sequence
<220> FEATURE:
<223> OTHER INFORMATION: Synthetic oligo

<400> SEQUENCE: 86

cagaaactat gcgtactgtg                                         20


<210> SEQ ID NO 87
<211> LENGTH: 22
<212> TYPE: DNA
<213> ORGANISM: Artificial Sequence
<220> FEATURE:
<223> OTHER INFORMATION: Synthetic oligo

<400> SEQUENCE: 87

agaaactatg cgtactgtgt tc                                      22
```